United States Patent
Bold et al.

(10) Patent No.: US 8,030,311 B2
(45) Date of Patent: Oct. 4, 2011

(54) PHENYLACETAMIDES SUITABLE AS PROTEIN KINASE INHIBITORS

(75) Inventors: Guido Bold, Gipf-Oberfrick (CH); Pascal Furet, Thann (FR); Vito Guagnano, Basel (CH); Clive McCarthy, Basel (CH); Andrea Vaupel, Riehen (CH)

(73) Assignee: Novartis AG, Basel (CH)

( * ) Notice: Subject to any disclaimer, the term of this patent is extended or adjusted under 35 U.S.C. 154(b) by 735 days.

(21) Appl. No.: 11/914,895

(22) PCT Filed: Apr. 12, 2006

(86) PCT No.: PCT/EP2006/003380
§ 371 (c)(1),
(2), (4) Date: Nov. 19, 2007

(87) PCT Pub. No.: WO2006/108640
PCT Pub. Date: Oct. 19, 2006

(65) Prior Publication Data
US 2008/0319005 A1    Dec. 25, 2008

(30) Foreign Application Priority Data
Apr. 14, 2005 (GB) .................................. 0507575.9

(51) Int. Cl.
A61K 31/497 (2006.01)
A61K 31/44 (2006.01)
C07D 401/12 (2006.01)
C07D 471/02 (2006.01)

(52) U.S. Cl. .................. 514/253.04; 514/303; 544/362; 546/118

(58) Field of Classification Search ............. 514/253.04, 514/303; 544/362; 546/118
See application file for complete search history.

(56) References Cited

U.S. PATENT DOCUMENTS

| 5,180,724 A | 1/1993 | Bowles et al. |
| 5,359,073 A | 10/1994 | Weier et al. |
| 2004/0019046 A1* | 1/2004 | Pevarello et al. .......... 514/227.8 |
| 2010/0075980 A1* | 3/2010 | Furet et al. ............... 514/253.04 |

FOREIGN PATENT DOCUMENTS

| WO | WO 91/17162 A1 | 11/1991 |
| WO | WO 02/48114 A1 | 6/2002 |
| WO | WO 02/48411 A | 6/2002 |
| WO | WO 03/099820 A | 12/2003 |
| WO | WO 2005/021531 A | 3/2005 |
| WO | WO 2006/108640 A1 | 10/2006 |
| WO | WO 2008/046802 A1 | 4/2008 |

OTHER PUBLICATIONS

Pevarello et al; "3-Aminopyrazole Inhibitors of CDK2/Cyclin A as Antitumor Agents. 2. Lead Optimization"; Journal of Medicinal Chemistry 48:2944-2956 (2005).

* cited by examiner

*Primary Examiner* — James O Wilson
*Assistant Examiner* — Ebenezer O Sackey

(57) ABSTRACT

The invention relates to compounds of the formula (I) wherein the moieties R1, R2, R3, R9, R10 and Q and X, Y and Z are as defined in the specification, and salts thereof, as well as their use, methods of use for them and method of their synthesis, and the like. The compounds are protein kinase inhibitors and can, inter alia, be used in the treatment of various proliferative diseases.

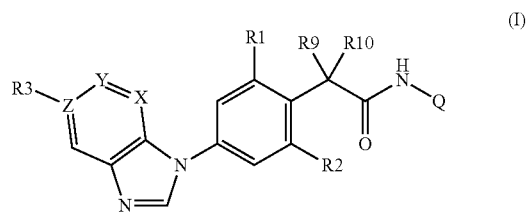

10 Claims, 1 Drawing Sheet

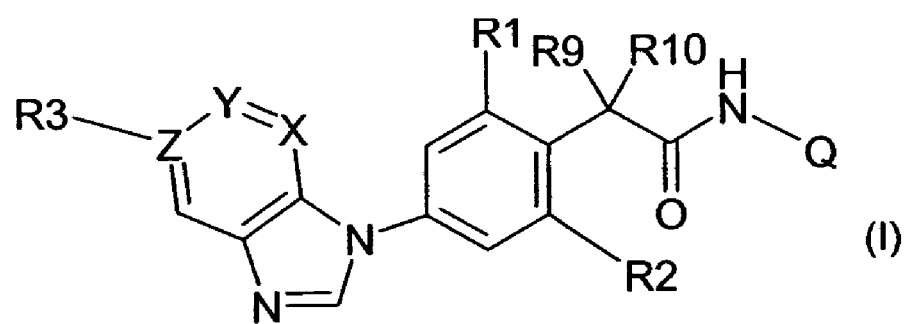

PHENYLACETAMIDES SUITABLE AS PROTEIN KINASE INHIBITORS

This application is the National Stage of Application No. PCT/EP06/03380, filed on Apr. 12, 2006, which claims benefit under 35 U.S.C. §119(e) of GB 0507575.9, filed Apr. 14, 2005. The contents of both are incorporated herein by reference in their entirety.

The invention relates to phenylacetyl amide derivatives, their use as protein kinase inhibitors, new pharmaceutical formulations comprising said compounds, said compounds for use in the diagnostic or therapeutic treatment of animals, especially humans, their use in the treatment of diseases or for the manufacture of pharmaceutical formulations useful in the treatment of diseases that respond to modulation of protein kinases, especially one or more selected from the group consisting of tie-2 and/or more especially PDGFR, VEGFR-2, c-Abl, Flt3, Ret and kit, activity, a pharmaceutical formulation e.g. useful in the treatment of diseases that respond to modulation of protein kinase comprising said compound, methods of treatment comprising administration of said compounds to a warm-blooded animal, especially a human, and/or processes for the manufacture of said compounds.

BACKGROUND OF THE INVENTION

Among the protein kinases, receptor-type kinases and non-receptor-type kinases can be distinguished, as well as tyrosine and serine/threonine kinases. Depending on their localization, nuclear, cytoplasmic and membrane-associated kinases can be distinguished. Membrane-associated tyrosine kinases often are at the same time receptors for growth factors.

Protein kinases (PKs) are enzymes which catalyze the phosphorylation of specific serine, threonine or tyrosine residues in cellular proteins. These post-translational modifications of substrate proteins act as molecular switch as a step in regulating cell proliferation, activation and/or differentiation. Aberrant or excessive or more generally inappropriate PK activity has been observed in several disease states including benign and malignant proliferative disorders. In many cases, it has been possible to treat diseases in vitro and in many cases in vivo, such as proliferative disorders, by making use of PK inhibitors.

The number of protein kinase inhibitors is high. In addition, a multitude of proliferative and other PK-related diseases exists. In some cases, the treated diseases develop resistance against therapeutics. Also, in some patients very specific treatments are required. Thus, there is a continuous need to provide new classes of compounds that are useful as PK inhibitors and consequently in the treatment of these Protein Tyrosine Kinase (PTK) related diseases in order to add to the present equipment of available drugs. What is required are new classes of pharmaceutically advantageous PK inhibiting compounds.

The Philadelphia Chromosome is a hallmark for chronic myelogenous leukaemia (CML) and carries a hybrid gene that contains N-terminal exons of the bcr gene and the major C-terminal part (exons 2-11) of the c-abl gene. The gene product is a 210 kD protein (p210 Bcr-Abl). The Abl-part of the Bcr-Abl protein contains the abl-tyrosine kinase which is tightly regulated in the wild type c-abl, but constitutively activated in the Bcr-Abl fusion protein. This deregulated tyrosine kinase interacts with multiple cellular signaling pathways leading to transformation and deregulated proliferation of the cells (Lugo et al., Science 247, 1079 [1990]). Mutant forms of the Bcr-Abl protein have also been identified. A detailed review of Bcr-Abl mutant forms has been published (Cowan-Jones et al, Mini Reviews in Medicinal Chemistry, 2004, 4 285-299). Treatment by inhibitors of c-abl and its mutations is useful against leukemias, e.g. AML and CML.

c-Kit is a tyrosine kinase receptor which belongs to the PDGF receptor family and becomes activated upon binding of its ligand SCF (stem-cell factor). The expression pattern of c-kit has been studied e.g. in a panel of different primary solid tumors. A strong expression of kit could be found inter alia in sarcoma, gastrointestinal stromal tumors (GIST), seminoma and carcinoids (Weber et al., J. Clin. Oncol. 22 (14S), 9642 (2004). GIST are non-epithelial tumors, diagnostically separate from other common forms of bowel cancer. Many occur in the stomach, less in the small intestine and still less in the esophagus. Dissemination to the liver, omentum and peritoneal cavity can be observed. GISTS probably arise from Interstitial Cajal Cells (ICC) which normally form part of the autonomic nervous system of the intestine and take part in the control of motility. Most (50 to 80%) of GISTs arise due to c-kit gene mutation. In the gut, a staining positive for c-kit/CD117 is likely to be a GIST. Mutations of c-kit can make c-kit function independent of activation by SCF, leading to a high cell division rate and possibly genomic instability. Also in mast shell tumors aberrations of c-kit could be observed, as well as in mastocytosis and associated myeloproliferative syndrome and Urticaria Pigmentosa. An expression and/or aberrations of c-kit can also be found in acute myeloic anemia (AML) and malign lymphomas. A c-kit expression can also be demonstrated in small cell bronchial carcinoma, seminomas, dysgerminomas, testicular intraepithelial neoplasias, melanomas, mamma carcinomas, neuroblastomas, Ewing sarcoma, some soft part sarcomas as well as papillary/follicular thyroid carcinoma (see Schütte et al., innovartis March 2001). Inherited mutations of the RET (rearranged during transfection) proto-oncogene are e.g. known to be tumorigenic in patients with multiple endocrine neoplasia type 2 (MEN 2) which may lead to pheochromocytoma, medullary thyroid carcinoma and parathyroid hyperplasia/adenoma (see Huang et al., Cancer Res. 60, 6223-6 (2000)). In patients with MEN 2, germ-line mutations of RET and sometimes duplication of a mutant RET allele in trisomy 10 or loss of the wild type RET allele are commonly identified and believed to be activating, i.e. causing ligand-independent dimerization of the receptor.

Platelet derived growth factor receptors such as PDGFR-alpha and -beta are also trans-membrane tyrosine kinase receptors. Upon binding of the ligand that is formed from two A, two B or in heterodimers from one A and one B chain (PDGF-A, PDGF-B or PDGF-AB), the receptor dimerizes and its tyrosine kinase is activated. This leads to downstream signaling and thus may support tumor growth. Mutations in this gene allow for receptor activation independent of ligand binding and appear to be driving forces in oncogenesis (see GIST may also be characterized by activating mutations in the platelet-derived growth factor-receptor-alpha (PDGRF) gene. An expression of PDGF, the growth factor that activates PDGFR, was observed in a number of different tumor cell lines, inter alia in mamma, colon, ovarian, prostate carcinoma, sarcoma and glioblastomas cell lines. Among the tumors, brain tumors and prostate carcinoma (including adenocarcinomas and bone metastasis) have found special interest. Interesting data also exist regarding malign gliomes (anaplastic astrocytomas/glioblastomas). Interesting pre-clinical data have also been obtained in the treatment of Dermatofibrosarcoma protuberans, a soft part tumor which is genetically characterized by a fusion of the collagen-type Iα1 (COLIA1) with the PDGF-A VEGFRs (vascular endothelial growth factor receptors) are known to be involved in the control of the onset of angiogenesis. As especially solid tumors depend on good blood supply, inhibition of VEGFRs and thus angiogenesis is under clinical investigation in the treatment of such tumors, showing promising results. VEGF is also a major player in leukemias and lymphomas and highly expressed in a variety of solid malignant tumors, correlating well with malignant disease progression. Examples of tumor diseases with VEGFR-2 (KDR) expression are lung carcinomas, breast carcinomas, Non Hodgkin's lymphomas, ovarian carcinoma, pancreatic cancer, malignant pleural mesothelioma and melanoma. In addition to its angiogenic activity, the ligand of VEGFR, VEGF, may promote tumor growth by direct pro-survival effects in tumor cells. Various other diseases are associated with deregulated angiogenesis, e.g. as mentioned below.

FLT3 is a member of the type III receptor tyrosine kinase (RTK) family. FLT3 (fms-like tyrosine kinase) is also known as FLk-2 (fetal liver kinase 2). Aberrant expression of the FLT3 gene has inter alia been documented in both adult and childhood leukemias including acute myeloid leukemia (AML), AML with trilineage myelodysplasia (AML/TMDS), acute lymphoblastic leukemia (ALL), and myelodysplastic syndrome (MDS), as well as MLL (mixed-lineage leukemia). Activating mutations of the FLT3 receptor have been found in about 35% of patients with acute myeloblastic leukemia (AML), and are associated with a poor prognosis. The most common mutation involves an in-frame duplication within the juxtamembrane domain, with an additional 5-10% of patients having a point mutation at asparagine 835. Both of these mutations are associated with constitutive activation of the tyrosine kinase activity of FLT3, and result in proliferation and viability signals in the absence of ligand. Patients expressing the mutant form of the receptor have been shown to have a decreased chance for cure. Thus, there is accumulating evidence for a role for hyperactivated (mutated) FLT3 kinase activity in human leukemias and myelodysplastic syndrome.

Angiopoietins (ligands of Tie-2) and Tie-2 are involved in vessel stabilization and vascular remodeling. It is known that Tie-2 is activated by one of its ligands, angiopoieitin-1, which is antagonized by a second ligand, angiopoietin-2 (ang2). In sites where angiogenesis takes place, the antagonist ang2 is up-regulated.

It is a problem to be solved by the present invention to provide new inhibitors of protein kinases, especially one or more of those just described, and to thus add new compounds to the few available compounds that exist so far.

GENERAL DESCRIPTION OF THE INVENTION

It has now been found that the compounds of formula I show inhibition of a number of protein kinases. The compounds of formula I, described below in more detail, especially show inhibition of one or more of the following protein kinases: tie-2, preferably c-Abl, Bcr-Abl, c-Kit, the RET proto-oncogene, Platelet-derived Growth Factor Receptors (PDGFRs), FLT3 receptor kinase and the Vascular Endothelial Growth Factor Receptors (VEGFRs) such as in particular VEGFR2. The compounds of formula I further also inhibit mutants of said kinases. In view of these activities, the compounds of formula I can be used for the treatment of diseases related to especially aberrant or excessive activity of such types of kinases, especially those mentioned.

DETAILED DESCRIPTION OF THE INVENTION

The invention especially relates to one or more compounds of the formula I,

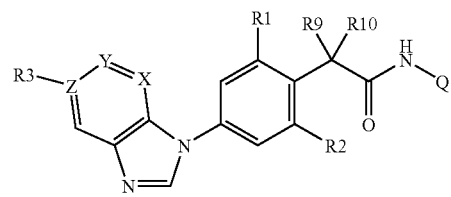

wherein
each of R1 and R2, independently of the other, is selected from the group consisting of hydrogen, halo and $C_1$-$C_7$-alkyl;
R3 is absent if Z is nitrogen or, if Z is C (carbon), is hydrogen, unsubstituted or substituted aryl or unsubstituted or substituted heterocyclyl;
X is N (nitrogen) or CH (hydrogen-substituted carbon),
Y is CH or N,
Z is C or N, and
Q is a moiety of the formula (A)

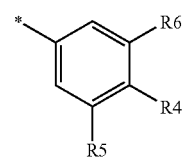

wherein
R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;
R5 is hydrogen, unsubstituted or substituted alkyl, unsubstituted or substituted amino, unsubstituted or substituted aryl or unsubstituted or substituted heterocyclyl; and
R6 is hydrogen, unsubstituted or substituted cycloalkyl or unsubstituted or (preferably) substituted alkyl;
or a moiety of the formula (B)

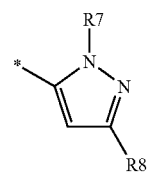

wherein
R7 is unsubstituted or substituted aryl or unsubstituted or substituted heterocyclyl and
R8 is alkyl or cycloalkyl;
where the asterisk * in formulae (A) and (B) marks the bond through which the moiety is bound to the NH of the amide group in formula I; and
(a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2- or —CH2-CH2-, R2 is selected from the group consisting of hydrogen, halo and $C_1$-$C_7$-alkyl, and R10 represents hydrogen; or a (preferably pharmaceutically acceptable) salt thereof.

The invention also relates to a compound of the formula I as defined above or below in the diagnostic or therapeutic treatment of an animal, especially a warm-blooded animal or a human, especially of a disease or disorder that responds to modulation, especially inhibition, of a protein kinase, preferably one or more protein kinases selected from the group consisting of tie-2 and/or more especially PDGFR, VEGFR-2, c-Abl, Flt3, Ret and kit, and/or one or more altered or mutated forms of any one or more of these.

Another embodiment of the invention relates to a pharmaceutical formulation comprising a compound of the formula I as defined above or below, or a pharmaceutically acceptable salt thereof, an at least one pharmaceutically acceptable carrier material.

Yet another embodiment of the invention relates to the use of a compound of the formula I, or a pharmaceutically acceptable salt thereof, in the preparation of a pharmaceutical formulation for the treatment of a disease or disorder that depends on (especially inappropriate) activity of a protein kinase, especially a protein tyrosine kinase, more especially one or more protein kinases selected from the group consisting of tie-2 and/or more especially PDGFR, VEGFR-2, c-Abl, Flt3, Ret and kit, and/or one or more altered or mutated forms of any one or more of these; or the use of said compounds in the treatment of a disease that depends on (especially inappropriate) activity of a protein kinase, especially a protein tyrosine kinase, especially as just defined.

The present invention also relates to a method of treating a kinase dependent and/or proliferative disease comprising administering a compound of the formula I, or a pharmaceutically acceptable salt thereof, to an animal, preferably a warm-blooded animal, especially a human.

Further embodiments of the invention can be found in the subsequent disclosure.

Listed below are definitions of various terms used to describe the compounds of the present invention as well as their use and synthesis, starting materials and intermediates and the like. These definitions, either by replacing one, more than one or all general expressions or symbols used in the present disclosure and thus yielding preferred embodiments of the invention, preferably apply to the terms as they are used throughout the specification unless they are otherwise limited in specific instances either individually or as part of a larger group. In other terms: Independently of each other, one or more of the more general expressions may be replaced by the more specific definitions, thus leading to preferred embodiments of the invention.

The term "lower" or "$C_1$-$C_7$-" defines a moiety with up to and including maximally 7, especially up to and including maximally 4, carbon atoms, said moiety being branched (one or more times) or straight-chained and bound via a terminal or a non-terminal carbon. Lower or $C_1$-$C_7$-alkyl, for example, is n-pentyl, n-hexyl or n-heptyl or preferably $C_1$-$C_4$-alkyl, especially as methyl, ethyl, n-propyl, sec-propyl, n-butyl, isobutyl, sec-butyl, tert-butyl.

Halo or halogen is preferably fluoro, chloro, bromo or iodo, most preferably fluoro, chloro or bromo, if not defined otherwise.

In unsubstituted or substituted aryl, aryl is preferably an unsaturated carbocyclic system of not more than 20 carbon atoms, especially not more than 16 carbon atoms, is preferably mono-, bi- or tri-cyclic, and is unsubstituted or, as substituted aryl, substituted preferably by one or more, preferably up to three, e.g. one or two substituents independently selected from the group consisting of phenyl, naphthyl, phenyl- or naphthyl-lower alkyl, such as benzyl; hydroxy-lower alkyl, such as hydroxymethyl; lower-alkoxy-lower alkyl, (lower-alkoxy)-lower alkoxy-lower alkyl, lower alkanoyl-lower alkyl, halo-lower alkyl, such as trifluoromethyl; phenoxy- or naphtyloxy-lower alkyl, phenyl- or naphthyl-lower alkoxy-lower alkyl, such as benzyloxy-lower alkyl; lower alkoxy-carbonyloxy-lower alkyl, such as tert-butoxycarbonyloxy-lower alkyl; phenyl- or naphthyl-lower alkoxycarbonyloxy-lower alkyl, such as benzyloxy-carbonyloxy-lower alkyl; cyano-lower alkyl, lower alkenyl being unsubstituted or substituted by unsubstituted or substituted amino, lower alkynyl, lower alkanoyl, such as acetyl; hydroxy, lower alkoxy, lower-alkoxy-lower alkoxy, (lower-alkoxy)-lower alkoxy-lower alkoxy, phenoxy, naphthyloxy, phenyl- or naphthyl-lower alkoxy, such as benzyloxy; amino-lower alkoxy, lower-alkanoyloxy, benzoyloxy, naphthoyloxy, nitro, halo, especially fluoro, chloro, bromo or iodo, amino, mono-di-substituted amino wherein the amino substituents are independently selected from lower alkyl, lower alkanoyl, phenyl, naphthyl, phenyl- and naphthyl-lower alkyl; cyano, carboxy, lower alkoxy carbonyl, e.g. methoxy carbonyl, n-propoxy carbonyl, isopropoxy carbonyl or tert-butoxycarbonyl; phenyl- or naphthyl-lower alkoxycarbonyl, such as benzyloxycarbonyl; lower alkanoyl, benzoyl, naphthoyl, carbamoyl, N-mono- or N,N-disubstituted carbamoyl, such as N-mono- or N,N-di-substituted carbamoyl wherein the substitutents are selected from lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, lower alkylsulfinyl, phenyl- or naphthyl-sulfinyl, phenyl- or naphthyl-lower alkylsulfinyl, lower alkylphenylsulfinyl, lower alkyl-napthylsulfinyl, sulfo, lower alkanesulfonyl, phenyl- or naphthylsulfonyl, phenyl- or naphthyl-lower alkylsulfonyl, alkylphenylsulfonyl, halogen-lower alkylsulfonyl, such as trifluoromethanesulfonyl; sulfonamido and benzosulfonamido; where each phenyl or naphthyl (also in phenoxy or naphthoxy) mentioned above as substitutent or part of a substituent of substituted aryl is itself unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl and/or naphthyl-lower alkyl)amino, nitro, carboxy, lower-alkoxycarbonyl carbamoyl, cyano and/or sulfamoyl.

In unsubstituted or substituted heterocyclyl, heterocyclyl is preferably a heterocyclic radical that is unsaturated, saturated or partially saturated and is preferably a monocyclic or in a broader aspect of the invention bicyclic or tricyclic ring; has 3 to 24, more preferably 4 to 16, most preferably 4 to 10 ring atoms; wherein one or more, preferably one to four, especially one or two carbon ring atoms are replaced by a heteroatom selected from the group consisting of nitrogen, oxygen and sulfur, the bonding ring preferably having 4 to 12, especially 5 to 7 ring atoms; where heterocyclyl is unsubstituted or substituted by one or more, especially 1 to 3, substituents independently selected from the group consisting of the substituents defined above under "substituted aryl"; and where heterocyclyl is especially a heterocyclyl radical selected from the group consisting of oxiranyl, azirinyl, aziridinyl, 1,2-oxathiolanyl, thienyl, furyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidyl, piperazinyl, pyridazinyl, morpholinyl, thiomorpholinyl, (S-oxo or S,S-dioxo)-thiomorpholinyl, indolizinyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl and chromanyl, each of these radicals being unsubstituted or substituted by one to two radicals selected from the group consisting of lower alkyl, especially methyl, ethyl, iso-propyl or tert-butyl, lower alkoxy, especially methoxy, and halo, especially bromo or chloro. In the case of R4, unsubstituted or substituted heterocyclyl is preferably not bound via a ring atom other than a ring nitrogen, but preferably via a carbon in order to avoid overlap with the definition of substituted amino.

In unsubstituted or substituted cycloalkyl, cycloalkyl is preferably a saturated mono- or bicyclic hydrocarbon group with 3 to 16, more preferably 3 to 9 ring carbon atoms, e.g. cyclopropyl, cyclobutyl, cyclopentyl, cyclohexyl, cycloheptyl or cyclooctyl, and is substituted by one or more, preferably one to three, substitutents independently selected from those described for substituted aryl or is (preferably) unsubstituted.

Unsubstituted or substituted amino is either amino (—NH$_2$) or amino in which one or two hydrogen atoms are replaced by a substituent independently selected from unsubstituted or substituted alkyl, especially as described below, unsubstituted or substituted aryl, especially as described above, unsubstituted or substituted heterocyclyl, especially as described above, unsubstituted or substituted cycloalkyl, especially as described above, and/or acyl, especially as described below (where preferably only one of the hydrogen atoms is replaced by acyl, the other is hydrogen or a moiety from those just mentioned other than acyl), or substituted amino in the form of an unsubstituted or substituted heterocyclyl as defined above with at least one nitrogen ring atom which is bound via a (preferably not charged, that is including the binding bond tertiary) ring nitrogen atom to the rest of the molecule (thus the substituted amino is one the substituents of which together with the amino nitrogen form a corresponding (unsubstituted or further substituted) heterocyclyl ring), especially selected from the group consisting of aziridinyl, pyrrolyl, pyrrolinyl, pyrrolidinyl, imidazolyl, imidazolidinyl, benzimidazolyl, pyrazolyl, pyrazinyl, pyrazolidinyl, piperidyl, piperazinyl, morpholinyl, thiomorpholinyl, (S-oxo or S,S-dioxo)thiomorpholinyl, isoindolyl, indolyl, benzimidazolyl, triazolyl, tetrazolyl, tetrahydroquinolyl, tetrahydroisoquinolyl, decahydroquinolyl, octahydroisoquinolyl, preferably a monocyclic saturated heterocyclyl with at least one nitrogen atom from those just mentioned; where heterocyclyl is unsubstituted or substituted by one or more, preferably one or to two radicals independently selected from those mentioned as substituents for aryl, preferably from the group consisting of lower alkyl, especially methyl or tert-butyl, lower alkoxy, especially methoxy, and halo, especially bromo or chloro. Especially preferred as unsubstituted or substituted amino are amino, N-mono- or N,N-di-[lower alkyl, N-mono- or N,N-di-(lower alkyl, phenyl and/or phenyl-lower alkyl)-amino-lower alkyl, (unsubstituted or lower alkyl-substituted)-piperidinyl, phenyl and/or phenyl-lower alkyl]-amino, such as N,N-dimethylamino, N,N-diethylamino, 3-[N—(N, N-dimethylamino)-propylamino, 2-[N—(N,N-dimethylamino)-ethylamino or N—(N,N-dimethylamino)-methylamino, N—[(N-mono- or N,N-di-($C_1$-$C_7$-alkyl)-amino)-$C_1$-$C_7$-alkyl]-N-(unsubstituted or $C_1$-$C_7$-alkyl)-amino, such as N-3-[N—(N,N-dimethylamino)-propyl-N-methyl-amino, N-2-[N—(N,N-dimethylamino)-ethyl-N-methyl-amino or N—(N,N-dimethylamino)-methyl-N-methyl-amino, N-piperidinylamino or N-lower alkyl-N-piperidin-ylamino wherein piperidinyl is unsubstituted or substituted by lower alkyl, e.g. N-lower alkyl-N-(1-lower alkyl-piperidin-4-yl)-amino, pyrrolidino, piperidino, piperazino, 4-lower alkyl-piperazino, such as 4-(methyl, ethyl or isopropyl)-piperazino, morpholino or thiomorpholino. Unsubstituted or substituted alkyl is preferably $C_1$- to $C_{20}$-alkyl, more preferably lower alkyl, that can be linear or branched one or more times (provided the number of carbon atoms allows this) and that is unsubstituted or substituted by one or more, preferably up to three, substitutents independently selected from the group consisting of unsubstituted or substituted heterocyclyl as described above, unsubstituted or substituted cycloalkyl as described above, unsubstituted or substituted aryl as defined above, especially phenyl or naphthyl; of lower alkenyl, lower alkynyl, lower alkanoyl, such as acetyl; hydroxy, lower alkoxy, lower-alkoxy-lower alkoxy, (lower-alkoxy)-lower alkoxy-lower alkoxy, phenoxy, naphthyloxy, phenyl- or naphthyl-lower alkoxy, such as benzyloxy; amino-lower alkoxy, lower-alkanoyloxy, benzoyloxy, naphthoyloxy, nitro, halo, cyano, carboxy, lower alkoxy carbonyl, e.g. methoxy carbonyl, n-propoxy carbonyl, iso-propoxy carbonyl or tert-butoxycarbonyl; phenyl- or naphthyl-lower alkoxycarbonyl, such as benzyloxycarbonyl; lower alkanoyl, benzoyl, naphthoyl, carbamoyl, N-mono- or N,N-disubstituted carbamoyl, such as N-mono- or N,N-di-substituted carbamoyl wherein the substitutents are selected from lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, lower alkylsulfinyl, phenyl- or naphthyl-sulfinyl, phenyl- or naphthyl-lower alkylsulfinyl, lower alkyl-phenylsulfinyl, lower alkyl-napthylsulfinyl, sulfo, lower alkane-sulfonyl, phenyl- or naphthyl-sulfonyl, phenyl- or naphthyl-lower alkylsulfonyl, alkylphenyl-sulfonyl, halogen-lower alkylsulfonyl, such as trifluoromethane-sulfonyl; sulfonamido, benzosulfonamido, amino, N-mono- or N,N-di-[lower alkyl, piperidinyl, N-lower alkylpiperidinyl wherein piperidinyl is unsubstituted or substituted by lower alkyl, N-mono- or N,N-di-(lower alkyl, phenyl and/or phenyl-lower alkyl)-amino]-lower alkyl, phenyl and/or phenyl-lower alkyl)-amino, such as N,N-dimethylamino, N,N-diethylamino, 3-[N—(N,N-dimethylamino)-propyl-amino, 2-[N—(N,N-dimethylamino)-ethylamino or N—(N,N-dimethylamino)-methylamino, pyrrolidino, piperidino, unsubstituted or N-lower alkyl substituted piperidinyl bound via a ring carbon atom, such as 1-isopropyl-piperidin-4-yl, piperazino, 4-lower alkylpiperazino, such as 4-(methyl, ethyl or isopropyl)-piperazino, morpholino or thiomorpholino; where each phenyl or naphthyl (also in phenoxy or naphthoxy) mentioned above as substituent or part of a substituent of substituted alkyl is itself unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl and/or naphthyl-lower alkyl)-amino, nitro, carboxy, lower-alkoxycarbonyl carbamoyl, cyano and/or sulfamoyl. Especially preferred are lower alkyl, halo-lower alkyl, such as trifluoromethyl, amino-lower alkyl, such as 3-aminopropyl, 2-aminoethyl or 2-aminomethyl, N-mono- or N,N-di-(lower alkyl, piperidinyl, N-lower alkylpiperidinyl, phenyl and/or phenyl-lower alkyl)-amino-lower alkyl, such as 3-(N,N-dimethylamino)-propyl, 2-(N,N-dimethylamino)-ethyl, N,N-dimethylaminomethyl, N,N-diethylaminomethyl or N-methyl-N-piperidin-4-yl-aminomethyl, pyrrolidino-lower alkyl, piperidino-lower alkyl, 1-lower alkylpiperidin-4-yl-lower alkyl, piperazino-lower alkyl, such as piperazino-methyl, 4-lower alkylpiperazino-lower alkyl, such as 4-(methyl, ethyl or isopropyl)-piperazino-methyl, or (morpholino or thiomorpholino)-lower alkyl.

Acyl is preferably an organic moiety selected from unsubstituted or substituted alkyl, unsubstituted or substituted aryl, unsubstituted or substituted heterocyclyl or unsubstituted or substituted cycloalkyl, each preferably as described above, bound via a carbonyl (—C(=O)—) or sulfonyl (—S(=O)$_2$—) group to the rest of the molecule, that is, a moiety derived from an organic carboxylic or sulfonic acid. Preferred are alkanoyl, especially lower alkanoyl, e.g. acetyl, benzoyl (=phenylcarbonyl), naphthoyl (=naphthylcarbonyl), phenyl-$C_1$-$C_7$-alkylcarbonyl, naphthyl-$C_1$-$C_7$-alkylcarbonyl, phenylsulfonyl or lower alkanesulfonyl, where each lower alkanoyl as acyl or each phenyl or naphthyl mentioned as part of acyl are unsubstituted or substituted by one or more, e.g. up to three, preferably 1 or 2, substituents independently selected from halo, especially fluoro, chloro, bromo or iodo, halo-lower alkyl, such as trifluoromethyl, hydroxy, lower alkoxy, amino, N-mono- or N,N-di-(lower alkyl, phenyl, naphthyl, phenyl-lower alkyl or naphthyl-lower alkyl)amino, nitro, carboxy, lower-alkoxycarbonyl, carbamoyl, cyano and/or sulfamoyl. Preferred are lower alkanoyl, benzoyl, phenylsulfonyl or tolylsulfonyl.

In unsubstituted or substituted alkenyl, alkenyl has one or more double bonds and preferably has 2 to 20, more preferably up to 12, carbon atoms; it is linear or can be branched one or more times (provided the number of carbon atoms allows this). Preferred is $C_2$-$C_7$-alkenyl, especially $C_3$ or $C_4$-alkenyl, such as allyl or crotyl. Alkenyl can be unsubstituted or substituted, especially by one or more, more especially up to three, of the substituents mentioned above as substituents for substituted alkyl, with the proviso that N, S or O with an active hydrogen is preferably not bound at a carbon atom from which a double bond emerges (as this would lead to tautomerism). Also other substituents that are not sufficiently stable are preferably excluded. Unsubstituted alkenyl, in particular $C_2$-$C_7$-alkenyl, is preferred. Unsubstituted or substituted alkynyl is preferably a moiety with one or more triple bonds and preferably has 2 to 20, more preferably up to 12, carbon atoms; it is linear or can be branched one or more times (provided the number of carbon atoms allows this). Preferred is $C_2$-$C_7$-alkynyl, especially $C_3$ or $C_4$-alkynyl, such as ethynyl or propyn-2-yl. Alkynyl can be unsubstituted or substituted, especially by one or more, more especially up to three, of the substituents mentioned above for substituted alkyl. Substituents such as amino or hydroxy (with free dissociable hydrogen) preferably are not bound to carbon atoms that participate at a triple bond, and also other substituents that are not sufficiently stable are preferably excluded. Unsubstituted alkynyl, in particular $C_2$-$C_7$-alkynyl, or N,N-di-(lower alkyl, phenyl and/or phenyl lower alkyl)-$C_3$-$C_7$-alkynyl, such as 3-(N,N-dimethylamino)-prop-1-ynyl, is preferred.

Salts are especially the pharmaceutically acceptable salts of compounds of formula I. They can be formed where salt forming groups, such as basic or acidic groups, are present that can exist in dissociated form at least partially, e.g. in a pH range from 4 to 10 in aqueous environment, or can be isolated especially in solid form.

Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, lactic acid, fumaric acid, succinic acid, citric acid, amino acids, such as glutamic acid or aspartic acid, maleic acid, hydroxymaleic acid, methylmaleic acid, benzoic acid, methane- or ethane-sulfonic acid, ethane-1,2-disulfonic acid, benzenesulfonic acid, 2-naphthalenesulfonic acid, 1,5-naphthalene-disulfonic acid, N-cyclohexylsulfamic acid, N-methyl-, N-ethyl- or N-propyl-sulfamic acid, or other organic protonic acids, such as ascorbic acid.

In the presence of negatively charged radicals, such as carboxy or sulfo, salts may also be formed with bases, e.g. metal or ammonium salts, such as alkali metal or alkaline earth metal salts, for example sodium, potassium, magnesium or calcium salts, or ammonium salts with ammonia or suitable organic amines, such as tertiary monoamines, for example triethylamine or tri(2-hydroxyethyl)amine, or heterocyclic bases, for example N-ethyl-piperidine or N,N'-dimethylpiperazine.

When a basic group and an acid group are present in the same molecule, a compound of formula I may also form internal salts.

For isolation or purification purposes it is also possible to use pharmaceutically unacceptable salts, for example picrates or perchlorates. For therapeutic use, only pharmaceutically acceptable salts or free compounds are employed (where applicable comprised in pharmaceutical preparations), and these are therefore preferred.

In view of the close relationship between the compounds in free form and in the form of their salts, including those salts that can be used as intermediates, for example in the purification or identification of the compounds or salts thereof, any reference to "compounds" (including also starting materials and "intermediates") hereinbefore and hereinafter, especially to the compound(s) of the formula I, is to be understood as referring also to one or more salts thereof or a mixture of a free compound and one or more salts thereof, each of which is intended to include also any solvate, metabolic precursor such as ester or amide of the compound of formula I, or salt of any one or more of these, as appropriate and expedient and if not explicitly mentioned otherwise. Different crystal forms and solvates may be obtainable and then are also included.

Where the plural form is used for compounds, salts, pharmaceutical preparations, diseases, disorders and the like, this is intended to mean also a single compound, salt, pharmaceutical preparation, disease or the like, where "a" or "an" is used, this means to refer to the indefinite article. or preferably to "one".

In some cases, a compound of the present invention may comprise one or more chiral centers in substitutents or show other asymmetry (leading to enantiomers) or may otherwise be able to exist in the form of more than one stereoisomer, e.g. due more than one chiral centers or more than one other type of asymmetry or due to rings or double bonds that allow for Z/E (or cis-trans) isomerism (diastereomers). The present inventions includes both mixtures of two or more such isomers, such as mixtures of enantiomers, especially racemates, as well as preferably purified isomers, especially purified enantiomers or enantiomerically enriched mixtures.

The compounds of formula I have valuable pharmacological properties and are useful in the treatment of kinase, especially tie-2 and/or more especially PDGFR, VEGFR-2, c-Abl, Flt3, Ret and/or kit, dependent diseases, e.g., as drugs to treat one or more proliferative diseases.

The terms "treatment" or "therapy" (especially of tyrosine protein kinase dependent diseases or disorders) refer to the prophylactic (including preventative, e.g. in patients where mutations or changes have been found that indicate that they are or may be prone to the development of a disease) or preferably therapeutic (including but not limited to palliative, curative, symptom-alleviating, symptom-reducing, disease- or symptom-suppressing, progression-delaying, kinase-regulating and/or kinase-inhibiting) treatment of said diseases, especially of any one or more of the diseases mentioned below.

The term "curative" as used herein means efficacy in treating ongoing episodes involving (specially deregulated) receptor tyrosine kinase activity.

The term "prophylactic" means the prevention of the onset or recurrence of diseases involving deregulated receptor tyrosine kinase activity.

The term "delay of progression" as used herein especially means administration of the active compound to patients being in a pre-stage or in an early phase of the disease to be treated, in which patients for example a pre-form of the corresponding disease is diagnosed or which patients are in a condition, e.g. during a medical treatment or a condition resulting from an accident, under which it is likely that a corresponding disease will develop, or where e.g. metastasation can be expected without treatment.

An animal is preferably a warm-blooded animal (or patient), more preferably a mammal, especially a human.

Where subsequently or above the term "use" is mentioned (as verb or noun) (relating to the use of a compound of the formula I or a pharmaceutically acceptable salt thereof), this (if not indicated differently or suggested differently by the context) includes any one or more of the following embodiments of the invention, respectively (if not stated otherwise): the use in the treatment of a protein (especially tyrosine) kinase dependent disease, the use for the manufacture of pharmaceutical compositions for use in the treatment of a protein kinase dependent disease, methods of use of one or more compounds of the formula I in the treatment of a protein kinase dependent and/or proliferative disease, pharmaceutical preparations comprising one or more compounds of the formula I for the treatment of said protein kinase dependent disease, and one or more compounds of the formula I in the treatment of said protein kinase dependent disease, as appropriate and expedient, if not stated otherwise. In particular, diseases to be treated and are thus preferred for "use" of a compound of formula I are selected from (especially tyrosine) protein kinase dependent ("dependent" meaning also "supported", not only "solely dependent", including also situations where a disease is responding to modulation, especially inhibition, of a protein kinase) diseases mentioned below, especially proliferative diseases mentioned below.

Where a protein kinase is mentioned, this relates to any type of protein kinase, especially serine/threonine and/or preferably protein tyrosine kinases, most preferably one or more tyrosine kinases selected from the group consisting of tie-2 and/or more especially PDGFR, VEGFR-2, c-Abl, Flt3, Ret and kit, including one or more altered or mutated or allelic forms of any one or more of these (e.g. those that result in conversion of the respective proto-oncogene into an onco-gene, such as constitutively activated mutants, e.g. Bcr-Abl). Especially an abnormally highly-expressed, constitutively activated or normal but in the given context of other regulatory mechanism in a patient relatively overactive, and/or mutated form is encompassed.

The usefulness of the compounds of the present invention in the modulation, especially as inhibitors, of protein kinases can especially and paradigmatically be demonstrated by the following test systems for the protein kinases mentioned as preferred above:

c-Abl, Bcr-Abl

The efficacy of the compounds of formula I as inhibitors of c-Abl protein tyrosine kinase activity can be demonstrated as follows:

An in vitro enzyme assay is performed in 96-well plates as a filter binding assay as described by Geissler et al. in Cancer Res. 1992; 52:4492-4498, with the following modifications. The His-tagged kinase domain of c-Abl is cloned and expressed in the baculovirus/Sf9 system as described by Bhat et al. in J. Biol. Chem. 1997; 272:16170-16175. A protein of 37 kD (c-Abl kinase) is purified by a two-step procedure over a Cobalt metal chelate column followed by an anion exchange column with a yield of 1-2 mg/L of Sf9 cells (Bhat et al., reference cited). The purity of the c-Abl kinase is >90% as judged by SDS-PAGE after Coomassie blue staining. The assay contains (total volume of 30 µL): c-Abl kinase (50 ng), 20 mM Tris-HCl, pH 7.5, 10 mM $MgCl_2$, 10 µM $Na_3VO_4$, 1 mM DTT and 0.06 µCi/assay [$\gamma^{33}P$]-ATP (5 µM ATP) using 30 µg/mL poly-Ala,Glu,Lys,Tyr-6:2:5:1 (Poly-AEKY, Sigma P1152) in the presence of 1% DMSO. Reactions are terminated by adding 10 µL of 250 mM EDTA and 30 µL of the reaction mixture is transferred onto Immobilon-PVDF membrane (Millipore, Bedford, Mass., USA) previously soaked for 5 min with methanol, rinsed with water, then soaked for 5 min with 0.5% $H_3PO_4$ and mounted on vacuum manifold with disconnected vacuum source. After spotting all samples, vacuum is connected and each well rinsed with 200 µL 0.5% $H_3PO_4$. Membranes are removed and washed on a shaker with 0.5% $H_3PO_4$ (4 times) and once with ethanol. Membranes are counted after drying at ambient temperature, mounting in Packard TopCount 96-well frame, and addition of 10 µL/well of Microscint™ (Packard). Using this test system, the compounds of formula I show $IC_{50}$ values of inhibition in the range of 0.002 to 100 µM, usually between 0.01 and 5 µM.

Bcr-Abl inhibition can be determined by a capture ELISA as follows: The murine myeloid progenitor cell line 32Dd3 transfected with the p210 Bcr-Abl expression vector pGDp210Bcr/Abl (32D-bcr/abl) is obtained from J Griffin (Bazzoni et al., J. Clin Invest. 98, 521-8 (1996); Zhao et al., Blood 90, 4687-9 (1997)). The cells express the fusion bcr-abl protein with a constitutively active abl kinase and proliferate growth factor-independent. The cells are expanded in RPMI 1640 (AMIMED; cat #1-41F01), 10% fetal calf serum, 2 mM glutamine (Gibco) ("complete medium"), and a working stock is prepared by freezing aliquots of $2 \times 10^6$ cells per vial in freezing medium (95% fetal calf serum, 5% dimethylsulfoxide (SIGMA, D-2650). After thawing, the cells are used during maximally 10-12 passages for the experiments. The antibody anti-abl SH3 domain cat. # 06-466 from Upstate Biotechnology is used for the ELISA. For detection of bcr-abl phosphorylation, the anti-phosphotyrosine antibody Ab PY20, labelled with alkaline phosphatase (PY10(AP)) from ZYMED (cat. # 03-7722) is used. As comparison and reference compound, (N-{5-[4-(4-methyl-piperazino-methyl)-benzoylamido]-2-methylphenyl}-4-(3-pyridyl)-2-pyrimidine-amine, in the form of the methane sulfonate (monomesylate) salt (ST1571) (marketed as Gleevec) or Glivec), Novartis), is used. A stock solution of 10 mM is prepared in DMSO and stored at −20° C. For the cellular assays, the stock solution is diluted in complete medium in two steps (1:100 and 1:10) to yield a starting concentration of 10 μM followed by preparation of serial threefold dilutions in complete medium. No solubility problems are encountered using this procedure. The test compounds of formula I are treated analogously. For the assay, 200,000 32D-bcr/abl cells in 50 μl are seeded per well in 96 well round bottom tissue culture plates. 50 μl per well of serial threefold dilutions of the test compound are added to the cells in triplicates. The final concentration of the test compound range e.g. from 5 μM down to 0.01 μM. Untreated cells are used as control. The compound is incubated together with the cells for 90 min at 37° C., 5% $CO_2$, followed by centrifugation of the tissue culture plates at 1300 rpm (Beckman GPR centrifuge) and removal of the supernatants by careful aspiration taking care not to remove any of the pelleted cells. The cell pellets are lysed by addition of 150 III lysis buffer (50 mM Tris/HCl, pH 7.4, 150 mM sodium chloride, 5 mM EDTA, 1 mM EGTA, 1% NP-40 (non-ionic detergent, Roche Diagnostics GmbH, Mannheim, Germany), 2 mM sodium ortho-vanadate, 1 mM phenylmethyl sulfonylfluoride, 50 μg/ml aprotinin and 80 μg/ml leupeptin) and either used immediately for the ELISA or stored frozen at −20° C. until usage. The anti-abl SH3 domain antibody is coated at 200 ng in 50 μl PBS per well to black ELISA plates (Packard HTRF-96 black plates; 6005207) overnight at 4° C. After washing 3× with 200 μl/well PBS containing 0.05% Tween 20 (PBST) and 0.5% TopBlock (Juro, Cat. # TB 232010), residual protein binding sites are blocked with 200 μl/well PBST, 3% TopBlock for 4 h at room temperature, followed by incubation with 50 μl lysates of untreated or test compound-treated cells (20 μg total protein per well) for 3-4 h at 4° C. After 3× washing, 50 μl/well PY20(AP) (Zymed) diluted to 0.5 μg/ml in blocking buffer is added and incubated overnight (4° C.). For all incubation steps, the plates are covered with plate sealers (Costar, cat. # 3095). Finally, the plates are washed another three times with washing buffer and once with deionized water before addition of 90 μl/well of the AP substrate CPDStar RTU with Emerald II. The plates now sealed with Packard Top Seal™-A plate sealers (cat. # 6005185) are incubated for 45 min at room temperature in the dark and luminescence is quantified by measuring counts per second (CPS) with a Packard Top Count Microplate Scintillation Counter (Top Count). For the final optimized version of the ELISA, 50 μl of the lysates of the cells grown, treated and lysed in 96 well tissue culture plates, are transferred directly from these plates to the ELISA plates that are precoated with 50 ng/well of the rabbit polyclonal ant-abl-SH3 domain AB 06-466 from Upstate. The concentration of the anti-phosphotyrosine AB PY20 (AP) can be reduced to 0.2 μg/ml. Washing, blocking and incubation with the luminescent substrate are as above. The quantification is achieved as follows: The difference between the ELISA readout (CPS) obtained for with the lysates of the untreated 32D-bcr/abl cells and the readout for the assay background (all components, but without cell lysate) is calculated and taken as 100% reflecting the constitutively phosphorylated bcr-abl protein present in these cells. The activity of the compound in the bcr-abl kinase activity is expressed as percent reduction of the bcr-abl phosphorylation. The values for the $IC_{50}$ are determined from the dose response curves by graphical inter- or extrapolation.

RET

RET kinase inhibition can be determined as follows:

Cloning and expression: The baculovirus donor vector pFB-GSTX3 is used to generate a recombinant baculovirus that expresses the amino acid region 658-1072 (Swiss prot No. Q9BTB0) of the cytoplasmic kinase domain of human RET-Men2A which corresponds to the wild-type kinase domain of RET (wtRET) and RET-Men2B, which differs from the wtRET by the activating mutation in the activation loop M918T. The coding sequence for the cytoplasmic domain of wtRET is amplified by PCR from a cDNA library using specific primers. RET-Men2B is generated through site-directed mutagenesis resulting in the M918T mutation. The amplified DNA fragments and the pFB-GSTX3 vector are made compatible for ligation by digestion with SalI and KpnI. Ligation of these DNA fragments results in the baculovirus donor plasmids pFB-GX3-RET-Men2A and pFB-GX3-RET-Men2B, respectively.

Production of virus: The baculovirus donor plasmids containing the kinase domains are transfected into the DH10Bac cell line (GIBCO) and the transfected cells are plated on selective agar plates. Colonies without insertion of the fusion sequence into the viral genome (carried by the bacteria) are blue. Single, white colonies are picked and viral DNA (bacmid) is isolated from the bacteria by standard plasmid purification procedures. Sf9 cells or Sf21 cells (American Type Culture Collection) are then transfected in 25 $cm^2$ flasks with the viral DNA using Cellfectin reagent.

Protein expression in Sf9 cells: Virus-containing media is collected from the transfected cell culture and used for infection to increase its titer. Virus-containing media obtained after two rounds of infection is used for large-scale protein expression. For large-scale protein expression 100 $cm^2$ round tissue culture plates are seeded with $5 \times 10^7$ cells/plate and infected with 1 mL of virus-containing media (approximately 5 MOIs). After 3 days, the cells are scraped off the plate and centrifuged at 500 rpm for 5 minutes. Cell pellets from 10-20, 100 $cm^2$ plates are re-suspended in 50 mL of ice-cold lysis buffer (25 mM Tris-HCl, pH 7.5, 2 mM EDTA, 1% NP-40, 1 mM DTT, 1 mM PMSF). The cells are stirred on ice for 15 minutes and then centrifuged at 5,000 rpms for 20 minutes.

Purification of GST-tagged proteins: The centrifuged cell lysate is loaded onto a 2 mL glutathione-sepharose column (Pharmacia) and washed 3× with 10 mL of 25 mM Tris-HCl, pH 7.5, 2 mM EDTA, 1 mM DTT, 200 mM NaCl. The GST-tagged proteins are then eluted by 10 applications (1 mL each) of 25 mM Tris-HCl, pH 7.5, 10 mM reduced-glutathione, 100 mM NaCl, 1 mM DTT, 10% glycerol and stored at −70° C.

Measurement of enzyme activity: Tyrosine protein kinase assays with either purified GST-wtRET or GST-RET-Men2B protein are carried out in a final volume of 30 μL containing 15 ng of either GST-wtRET or GST-RET-Men2B protein, 20 mM Tris-HCl, pH 7.5, 1 mM $MnCl_2$, 10 mM $MgCl_2$, 1 mM DTT, 3 μg/mL poly(Glu,Tyr) 4:1, 1% DMSO, 2.0 μM ATP (γ-[$^{33}$P]-ATP 0.1 μCi). The activity is assayed in the presence or absence of inhibitors, by measuring the incorporation of $^{33}$P from [γ$^{33}$P] ATP into poly(Glu,Tyr) 4:1. The assay is carried out in 96-well plates at ambient temperature for 15 minutes under conditions described above and terminated by the addition of 20 μL of 125 mM EDTA. Subsequently, 40 μL of the reaction mixture are transferred onto Immobilon-PVDF membrane (Millipore) previously soaked for 5 minutes with methanol, rinsed with water, then soaked for 5 minutes with 0.5% $H_3PO_4$ and mounted on vacuum manifold with disconnected vacuum source. After spotting all samples, vacuum is connected and each well rinsed with 200 μL 0.5%

H$_3$PO$_4$. Membranes are removed and washed 4× on a shaker with 1.0% H$_3$PO$_4$, once with ethanol. Membranes are counted after drying at ambient temperature, mounting in Packard TopCount 96-well frame, and addition of 10 μL/well of Microscint™ (Packard). IC$_{50}$ values are calculated by linear regression analysis of the percentage inhibition of each compound in duplicate, at 4 concentrations (usually 0.01, 0.1, 1 and 10 μM). One unit of protein kinase activity is defined as 1 nmole of $^{33}$P transferred from [γ33P] ATP to the substrate protein/minute/mg of protein at 37° C. The compounds of formula I here show IC$_{50}$ values in the range between 0.07 and 20 μM, especially between 0.1 and 5 μM.

PDGFR

The efficacy of the compounds of formula I as inhibitors of c-Kit and PDGFR tyrosine kinase activity can be demonstrated as follows:

BaF3-Tel-PDGFRbeta is a BaF3 murine proB-cell lymphoma cell derivative [the BaF3 cell line is available from the German Collection of Microorganisms and Cell Cultures (DSMZ), Braunschweig, Germany] that has been rendered IL-3-independent by stable transduction with Tel-fusion-activated PDGFR-β wild-type (Golub T. R. et al., Cell 77(2): 307-316, 1994) or D816V-mutation-activated c-kit, respectively. Cells are cultured in RPMI-1640 (Animed # 1-14F01-I) supplemented with 2% L-glutamine (Animed # 5-10K50-H) and 10% fetal calf serum (FCS, Animed # 2-01F16-I). Wild-type, untransfected BaF3 cells are maintained in above medium plus 10 U/ml IL-3 (mouse Interleukin-3, Roche 4# 1380745).

Cells are diluted in fresh medium to a final density of 3×10$^5$ cells per ml and 50 μl aliquots seeded into 96-well plates (1.5×10$^4$ cells per well). 50 μl 2× compound solutions are added. As internal control, the kinase inhibitor PKC412 is routinely used. Control cells treated with DMSO (0.1% final concentration) serve as growth reference (set as 100% growth). In addition, a plate blank value is routinely determined in a well containing only 100 μl of medium and no cells. IC50 determinations are performed based on eight 3-fold serial dilutions of the test compound, starting at 10 μM. Following incubation of the cells for 48 h at 37° C. and 5% CO$_2$, the effect of inhibitors on cell viability is assessed by the resazurin sodium salt dye reduction assay (commercially known as AlamarBlue assay) basically as previously described (O'Brien J. et al., Eur. J. Biochem. 267: 5421-5426, 2000). 10 μl of AlamarBlue is added per well and the plates incubated for 6 h at 37° C. and 5% CO$_2$. Thereafter, fluorescence is measured using a Gemini 96-well plate reader (Molecular Devices) with the following settings: Excitation 544 nm and Emission 590 nm. Acquired raw data are exported to Excel-file format. For data analysis, the plate blank value is subtracted from all data points. The anti-proliferative effect of a compound by the AlamarBlue read-out was then calculated as percentage of the value of the control cells set as 100%. IC$_{50}$ values are determined using XLfit software program. The compounds of formula I show an IC$_{50}$ for PDGFR-β, in the range of 0.001 to 20 μM, especially between 0.002 and 0.1 μM.

c-Kit can be measured analogously using BaF3-KitD816V murine proB lymphoma cell derivatives.

FLT3 Receptor Kinase

To search for FLT3-targeted compounds, two different kinds of assays can be employed:

Flt3 kinase activity is determined as follows: The baculovirus donor vector pFbacG01 (GIBCO) is used to generate a recombinant baculovirus expressing the amino acid region from amino acids 563-993 of the cytoplasmic kinase domain of human Flt3. The coding sequence for the cytoplasmic domain of Flt3 is amplified by PCR from human c-DNA libraries (Clontech). The amplified DNA fragments and the pFbacG01 vector are made compatible for ligation by digestion with BamHI and HindIII. Ligation of these DNA fragments results in the baculovirus donor plasmid Flt-3(1.1). The production of the viruses, the expression of protein in Sf9 cells and the purification of the GST-fused protein is performed as follows:

Production of virus: Transfer vector)pFbacG01-Flt-3) containing the Flt3-kinase domain is transfected into the DH10Bac cell line (GIBCO) and the transfected cells are plated on selective agar plates. Colonies without insertion of the fusion sequence into the viral genome (carried by the bacteria) are blue. Single white colonies are picked and viral DNA (bacmid) is isolated from the bacteria by standard plasmid purification procedures. Sf9 or Sf21 cells (American Type Culture Collection) are then transfected in flasks with the viral DNA using Cellfectin reagent.

Determination of small scale protein expression on Sf9 cells: Virus containing medium is collected from the transfected cell culture and used for infection to increase its titre. Virus containing medium obtained after two rounds of infection is sued for large-scale protein expression. For large-scale protein expression, 100 cm$^2$ round tissue culture plates are seeded with 5×10$^7$ cells/plate and infected with 1 ml of virus-containing medium (approximately 5 MOIs). After 3 days, the cells are scraped off the plate and centrifuged at 500 rpm for 5 min. Cell pellets from 10-20 plates with each 100 cm$^2$ are resuspended in 50 ml of ice-cold lysis buffer (25 mM Tris-HCl, pH 7.5, 2 mM EDTA, 1% NP-40, 1 mM DTT, 1 mM PMSF). The cells are stirred on ice for 15 min and then centrifuged at 5000 rpm for 20 min.

Purification of GST-tagged protein: The centrifuged cell lysate is loaded onto a 2 ml glutathione-sepharose column (Pharmacia) and washed three times with 10 ml of 25 mM Tris-HCl, pH 7.5, 2 mM EDTA, 1 mM DTT; 200 mM NaCl. The GST-tagged protein is then eluted by 10 applications (1 ml each) of 25 mM Tris-HCl, pH 7.5, 10 mM reduced glutathione, 100 mM NaCl, 1 mM DTT, 10% glycerol, and stored at −70° C.

Measurement of Enzyme activity: Tyrosine protein kinase assays with purified GST-Flt2 are carried out in a final volume of 30 μl containing 200-1800 ng of enzyme protein (depending on the specific activity), 20 mM Tris-HCl, pH 7.6, 3 mM MnCl$_2$, 3 mM MgCl$_2$, 1 mM DTT, 10 μM Na$_3$VO$_4$, 3 μg/ml poly(Glu,Tyr) 4:1, 1% DMSO, 6.0 μM ATP and 0.1 μCi [γ$^{33}$P]ATP. The activity is assayed in the presence or absence of inhibitors, by measuring the incorporation of $^{33}$P from [γ$^{33}$P]ATP into the poly(Glu,Tyr) substrate. The assay (30 μl per well) is carried out in 96-well plates at ambient temperature for 20 min under conditions described below and terminated by the addition of 20 μl of 125 mM EDTA. Subsequently, 40 μl of each reaction mixture is transferred onto Immobilon-PVDF membrane (Millipore, Bedford, Mass., USA) previously soaked for 5 min with methanol, rinsed with water, then soaked for 5 min with 0.5% H$_3$PO$_4$ and mounted on vacuum manifold with disconnected vacuum source. After spotting all samples, vacuum is connected and each well rinsed with 200 μl 0.5% H$_3$PO$_4$. Membranes are removed and washed 4× on a shaker with 1.0% H$_3$PO$_4$, once with ethanol. Membranes are then counted individually after drying at ambient temperature, mounting in Packard TopCount 96-well frame and addition of 10 fi/well Microscint™ (Pakard). IC50 values are calculated by linear regression analysis of the percentage inhibition of each compound in duplicate, at four concentrations (usually 0.01, 0.1, 1 and 10 μM). One unit of protein kinase is defined as 1 nmole of $^{33}$P ATP transferred from [γ33P]ATP to the substrate polypeptide per minute per mg of protein at 37° C. The compounds of the formula I here show $IC_{50}$ values in the range between 0.03 and 100 µM, preferably between 0.2 and 10 µM.

Alternatively or in addition, a cell based assay can be utilised to identify inhibitors of mutant FLT3 tyrosine kinase receptors. The general technique involves comparing the effects of possible inhibitors on cell lines that depended on mutant FLT3 for proliferation, versus cell lines that do not depend on mutant FLT3 for proliferation. Cell lines expressing two different forms of mutated, activated FLT3 are used:

Ba/F3-FLT3-ITD cells expressing a FLT3 mutant with an "Internal Tandem Duplication" (ITD) within the juxtamembrane domain of the receptor.

Ba/F3-FLT3-D835Y cells expressing an FLT3 receptor containing a mutation converting Asparagine at position 835 to Tyrosine.

Tested compounds of the formula I can be shown to inhibit proliferation of both Ba/F3-FLT3-ITD and Ba/F3-D835Y cells while on the other hand they usually do not inhibit growth of untransformed Ba/F3 cells at concentrations of up to 500 nM, and the growth inhibitory effects of a compound of the formula I on Ba/F3-FLT3-ITD cells can be reversed by the addition of high concentrations of IL-3 to provide an alternative viability signal. At the concentrations required to inhibit the proliferation of FLT3-dependent cell-lines, compounds of the formula I can be shown to be not cytotoxic against several human leukemia and lymphoma cell lines that do not have mutant FLT3 receptors (hyperactivated kinases), suggesting that the drug has an unexpected high degree of specificity as a cytoxic agent. Overall, these results indicate that compounds of the formula I can be potent inhibitors of mutant FLT3 receptor tyrosine kinase activity and are a promising candidate for use in the treatment in patients with mutant FLT3 receptors. In particular, tested compounds of the formula I can be shown inhibits the activity of FLT3 receptor tyrosine kinase activity in concentrations in the range of 0.00015 to 1.0 µM.

VEGF-R (KDR) Autophosphorylation

The inhibition of VEGF-induced receptor autophosphorylation can be confirmed with an in vitro experiments in cells such as transfected CHO cells, which permanently express human VEGF-R2 (KDR), are seeded in complete culture medium (with 10% fetal calf serum=FCS) in 6-well cell-culture plates and incubated at 37° C. under 5% $CO_2$ until they show about 80% confluency. The compounds to be tested are then diluted in culture medium (without FCS, with 0.1% bovine serum albumin) and added to the cells. (Controls comprise medium without test compounds). After two hours of incubation at 37° C., recombinant VEGF is added; the final VEGF concentration is 20 ng/ml. After a further five minutes incubation at 37° C., the cells are washed twice with ice-cold PBS (phosphate-buffered saline) and immediately lysed in 100 µl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the VEGF-R2 phosphorylation: a monoclonal antibody to VEGF-R2 (for example Mab 1495.12.14; prepared by H. Towbin, Novartis or comparable monoclonal antibody) is immobilized on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)sorbitane monolaurate, ICI/Uniquema) (PBST). The cell lysates (20 µg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Biosystems). The luminescence is measured in a Packard Top Count Microplate Scintillation Counter. The difference between the signal of the positive control (stimulated with VEGF) and that of the negative control (not stimulated with VEGF) corresponds to VEGF-induced VEGF-R2 phosphorylation (=100%). The activity of the tested substances is calculated as percent inhibition of VEGF-induced VEGF-R2 phosphorylation, wherein the concentration of substance that induces half the maximum inhibition is defined as the $IC_{50}$ (inhibitory dose for 50% inhibition). The compounds of formula I here show an $IC_{50}$ in the range of 0.01 to 20 µM, especially between 0.1 and 1.0 µM.

VEGF-R1

VEGF-R1 inhibition can be shown as follows: the test is conducted using Flt-1 VEGF-receptor tyrosine kinase. The detailed procedure is as follows: 30 µl kinase solution (kinase domain of Flt-1, Shibuya et al., Oncogene 5, 519-24 [1990], according to the specific activity, in order to achieve an activity of 4000-6000 counts per minute [cpm] in the sample without inhibitor) in 20 mM Tris-HCl pH 7.5, 3 mM manganese dichloride ($MnCl_2$), 3 mM magnesium chloride ($MgCl_2$) and 3 µg/ml poly(Glu,Tyr) 4:1 (Sigma, Buchs, Switzerland), 8 µM [$^{33}$P]-ATP (0.2 µCi/batch), 1% dimethyl sulfoxide, and 0 to 50 µM of the compound to be tested are incubated together for 10 minutes at room temperature. The reaction is then ended by the addition of 10 µl 0.25 M ethylenediaminetetraacetate (EDTA) pH 7. Using a multichannel dispenser (LAB SYSTEMS, USA), an aliquot of 20 µl is applied to a PVDF (=polyvinyl difluoride) Immobilon P membrane (Millipore, USA), which is incorporated into a Millipore microtitre filter manifold, and connected to a vacuum. Following complete elimination of the liquid, the membrane is washed 4 times successively in a bath containing 0.5% phosphoric acid ($H_3PO_4$), incubated for 10 minutes each time while shaking, then mounted in a Hewlett Packard TopCount Manifold and the radioactivity measured after the addition of 10 µl Microscint® (β-scintillation counter liquid; Packard USA). $IC_{50}$-values are determined by linear regression analysis of the percentages for the inhibition of each compound in three concentrations (as a rule 0.01, 0.1, and 1 µM).

The efficiency of compounds of the formula I as inhibitors of tumor growth can be demonstrated using various in vivo models, for example, as follows:

For example, in order to test whether a compound of the formula I, e.g. according to one of the Examples given below, inhibits VEGF-mediated angiogenesis in vivo, its effect on the angiogenic response induced by VEGF in a growth factor implant model in mice is tested: A porous Teflon chamber (volume 0.5 mL) is filled with 0.8% w/v agar containing heparin (20 units/ml) with or without growth factor (2 µg/ml human VEGF) is implanted subcutaneously on the dorsal flank of C57/C6 mice. The mice are treated with the test compound (e.g. 25, 50 or 100 mg/kg p.o. once daily) or vehicle starting on the day of implantation of the chamber and continuing for 4 days after. At the end of the treatment, the mice are killed, and the chambers are removed. The vascularized tissue growing around the chamber is carefully removed and weighed, and the blood content is assessed by measuring the hemoglobin content of the tissue (Drabkins method; Sigma, Deisenhofen, Germany). It has been shown previously that these growth factors induce dose-dependent increases in weight and blood content of this tissue growing (characterized histologically to contain fibroblasts and small blood vessels) around the chambers and that this response is blocked by antibodies that specifically neutralize VEGF (see Wood J M et al., Cancer Res. 60(8), 2178-2189, (2000); and Schlaeppi et al., J. Cancer Res. Clin. Oncol. 125, 336-342, (1999)).

With such types of model, it is possible to show inhibition of tumor growth with compounds of the formula I if tested.

Tie-2 Receptor Autophosphorylation

The inhibition of Tie-2 receptor autophosphorylation can be confirmed with an in vitro experiment in cells such as transfected COS cells (ATCC Number: CRL-1651), which permanently express human Tie-2 (SwissProt Acc No Q02763), are seeded in complete culture medium (with 10% fetal calf serum =FCS) in 6-well cell-culture plates and incubated at 37° C. under 5% $CO_2$ until they show about 90% confluency. The compounds to be tested are then diluted in culture medium (without FCS, with 0.1% bovine serum albumin) and added to the cells. Controls comprise medium without test compounds. After 40 min of incubation at 37° C., ortho vanadate is added to give the final concentration of 10 mM. After a further incubation for 20 minutes at 37° C., the cells are washed twice with ice-cold PBS (phosphate-buffered saline) and immediately lysed in 100 μl lysis buffer per well. The lysates are then centrifuged to remove the cell nuclei, and the protein concentrations of the supernatants are determined using a commercial protein assay (BIORAD). The lysates can then either be immediately used or, if necessary, stored at −20° C.

A sandwich ELISA is carried out to measure the Tie-2 phosphorylation: a monoclonal anti-body to Tie-2 (for example anti-Tie2 clone AB33, Upstate, Cat Nr. 05-584 or comparable monoclonal antibody) is immobilized using 0.1 ml of a 2 μg/ml solution on black ELISA plates (OptiPlate™ HTRF-96 from Packard). The plates are then washed and the remaining free protein-binding sites are saturated with 3% TopBlock® (Juro, Cat. # TB232010) in phosphate buffered saline with Tween 20® (polyoxyethylen(20)sorbitane monolaurate, ICI/Uniquema) (PBST). The cell lysates (100 μg protein per well) are then incubated in these plates overnight at 4° C. together with an antiphosphotyrosine antibody coupled with alkaline phosphatase (PY20:AP from Zymed). The (plates are washed again and the) binding of the antiphosphotyrosine antibody to the captured phosphorylated receptor is then demonstrated using a luminescent AP substrate (CDP-Star, ready to use, with Emerald II; Applied Bio-systems). The luminescence is measured in a Packard Top Count Microplate Scintillation Counter. The difference between the signal of the positive control (stimulated with vanadate) and that of the negative control (not stimulated) corresponds to maximum Tie-2 phosphorylation (=100%). The activity of the tested substances is calculated as percent inhibition of maximum Tie-2 phosphorylation, and the concentration of substance that induces half the maximum inhibition is defined as the $IC_{50}$ (inhibitory dose for 50% inhibition). For compounds of the formula I, preferably $IC_{50}$ values in the range from 0.05 to 20 μM can be found, e.g. more preferably from 0.1 to 10 μM.

In view of their protein kinase modulating (especially inhibiting) properties and/or possibly other not yet known mechanisms, the use of the present compounds in the treatment of a variety of proliferative diseases, including those mentioned below, and/or diseases that depend on (especially inappropriate) protein kinase activity is possible.

For example, compounds of the present invention can be used in the treatment of leukemias (of adult or childhood type), especially chronic myelogenous leukaemia (CML), AML (acute myeloid leukemia), AML with trilineage myelodysplasia (AML/TMDS), acute lymphoblastic leukemia (ALL), myelodysplastic syndrome (MDS), as well as MLL (mixed-lineage leukemia); different (especially primary, but also derived) solid tumors (including benign or especially malign types) such as sarcoma (e.g. Ewing sarcoma, Kaposi's sarcoma or soft part sarcomas such as Dermatofibrosarcoma protuberans), gastrointestinal stromal tumors (GIST), seminoma, carcinoids, mast cell tumors, lung carcinomas, such as small or large cell lung carcinoma, bronchial carcinomas, such as small cell bronchial carcinoma, seminomas, dysgerminomas, testicular intraepithelial neoplasias, melanomas, mamma carcinomas, neuroblastomas, papillary/follicular thyroid carcinoma, malign lymphomas, Non Hodgkin's lymphoma, multiple endocrine neoplasia type 2 (MEN 2), pheochromocytoma, thyroid carcinoma, e.g. medullary thyroid carcinoma, parathyroid hyperplasia/adenoma, mamma carcinoma, colon cancer, colorectal adenoma, ovarian cancer, prostate carcinoma, glioblastoma, brain tumors, prostate carcinoma (also including adenocarcinomas and bone metastatsis), malign gliomes (anaplastic astrocytomas/glioblastomas), pancreatic cancer, malignant pleural mesothelioma, hemangioblastoma, haemangioma, carcinoma of the kidney, liver, adrenal gland, bladder, stomach (especially gastric tumors), rectum, vagina, cervix, endometrium, multiple myeloma, tumors of the neck and head, e.g. squameous carcinoma of the head and neck, including neoplasias, especially of epithelial character, e.g. in the case of mammary carcinoma, malignant nephrosclerosis;

or of other hyperplasias or proliferative diseases, such as mastocytosis, associated myeloproliferative syndrome, Urticaria Pigmentosa, an epidermal hyperproliferation (other than cancer), especially psoriasis; prostate hyperplasia; inflammatory diseases, such as rheumatoid or rheumatic inflammatory diseases, especially arthritis, such as rheumatoid arthritis, other chronic inflammatory disorders, such as chronic asthma, arterial or post-transplantational atherosclerosis, other diseases associated with deregulated angiogenesis, e.g. fibrosis (especially pulmonary, but also other types of fibrosis, such as renal fibrosis), angiogenesis, smooth muscle proliferation in the blood vessels, such as stenosis or (e.g. stent-induced) restenosis following angioplasty; (e.g. ischemic) retinopathies, (for example, age related) macula degeneration, other eye diseases, such as diabetic retinopathy and neovascular glaucoma; renal diseases, such as glomerulonephritis; diabetic nephropathy; inflammatory bowel disease, such as Crohn's disease, thrombotic microangiopathic syndromes; (e.g. chronic) transplant rejections and glomerulopathy; fibrotic diseases, such as cirrhosis of the liver; mesangial cell-proliferative diseases and or injuries of the nerve tissue.

In addition, they can be useful as immunosuppressants, as an aid in scar-free wound healing, and for treating age spots and contact dermatitis.

In spite of the mechanism mentioned in the "Background of the Invention", surprisingly also tie-2 inhibition can be shown to be useful against proliferative diseases, especially solid tumors.

Process of Manufacture

A compound of formula I can be prepared analogously to methods that, for other compounds, are in principle known in the art, so that for the novel compounds of the formula I the process is novel as analogy process, preferably by reacting a carboxylic acid compound of the formula II,

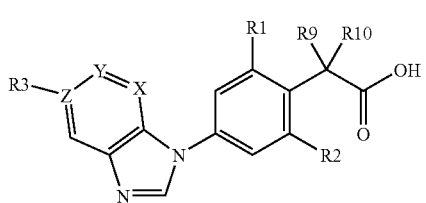

(II)

or a reactive derivative thereof, wherein R1, R2, R3, R9, R10, X, Y and Z are as defined for a compound of the formula I, with an amino compound of the formula III,

Q-NH$_2$ (III)

wherein Q is as defined for a compound of the formula I, and, if desired, transforming an obtainable compound of formula I into a different compound of formula I, transforming a salt of an obtainable compound of formula I into the free compound or a different salt, transforming an obtainable free compound of formula I into a salt thereof, and/or separating an obtainable mixture of isomers of a compound of formula I into individual isomers;

where in any one or both starting materials of the formula II and/or III functional groups that shall not take part in the reaction may be present in protected form and protecting groups are removed to obtain a compound of the formula I.

The condensation of an acid of the formula II, or a reactive derivative thereof, under () preferably takes place under customary condensation conditions, where among the possible reactive derivatives of an acid of the formula II reactive esters (such as the hydroxybenzotriazole (HOBT), pentafluorophenyl, 4-nitrophenyl or N-hydroxysuccinimide ester), acid halogenides (such as the acid chloride or bromide) or reactive anhydrides (such as mixed anhydrides with lower alkanoic acids or symmetric anhydrides) are preferred. Reactive carbonic acid derivatives can also and preferably be formed in situ. The reaction can then be carried out by dissolving the compounds of formulae II and III in a suitable solvent, for example a halogenated hydrocarbon, such as methylene chloride, N,N-dimethylformamide, N,N-dimethylacetamide, N-methyl-2-pyrrolidone, methylene chloride, or a mixture of two or more such solvents, and by the addition of a suitable base, for example triethylamine, diisopropylethylamine (DIEA) or N-methylmorpholine and, if the reactive derivative of the acid of the formula II is formed in situ, a suitable coupling agent that forms a preferred reactive derivative of the carbonic acid of formula III in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N, N',N'-tetramethyluronium tetrafluoroborate (TBTU); (benzotriazol-1-yloxy)-tripyrrolidinophosphonium-hexafluorophosphate (PyBOP), 1-(3-dimethylaminopropyl)-3-ethylcarbodiimide hydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, Synthesis 1972, 453-463. The reaction mixture is preferably stirred at a temperature of from approximately −20 to 50° C., especially from −5° C. to 30° C., e.g. at 0° C. to room temperature. The reaction may preferably carried out under an inert gas, e.g. nitrogen or argon. If required, the subsequent removal of protecting groups takes place. The subsequent removal of a protecting group, such as tert-butoxycarbonyl, methoxymethyl, benzyl, 2-(trimethylsilyl)-ethoxycarbonyl or tert-butyldimethylsilyl, if required, takes place under standard conditions, see also the literature mentioned below under General Process Conditions.

Optional Reactions and Conversions

Compounds of the formula I, or protected forms thereof directly obtained according to the preceding procedure or after introducing protecting groups anew, which are included subsequently as starting materials for conversions as well even if not mentioned specifically, can be converted into different compounds of the formula I according to known procedures, where required followed removal of protecting groups.

For example, in a compound of the formula I wherein Q is aryl that is substituted by iodo or bromo and possibly one or more other substitutents, such as trifluoro, e.g. where Q is 4-iodo-3-trifluoromethylphenyl, the bromo or iodo may be replaced with substituted or unsubstituted phenyl, such as 4-cyanophenyl, by coupling reaction with the corresponding substituted or unsubstituted phenylboronic acid of the formula IV, Phe-B(OH)$_2$ (IV)

wherein Phe is unsubstituted or substituted aryl, in the presence of a catalyst, especially PdCl$_2$(dppf) and preferably also a base, such as an alkali metal carbonate, e.g. sodium carbonate, in an appropriate solvent or solvent mixture, e.g. toluene/water, at, for example, elevated temperatures, e.g. between 30° C. and the (preferred) reflux temperature.

Salts of compounds of formula I having at least one salt-forming group may be prepared in a manner known per se. For example, salts of compounds of formula I having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of formula I are obtained in customary manner, e.g. by treating the compounds with an acid or a suitable anion exchange reagent. Internal salts of compounds of formula I containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

A salt of a compound of the formula I can be converted in customary manner into the free compound; metal and ammonium salts can be converted, for example, by treatment with suitable acids, and acid addition salts, for example, by treatment with a suitable basic agent. In both cases, suitable ion exchangers may be used.

Stereoisomeric mixtures, e.g. mixtures of diastereomers, can be separated into their corresponding isomers in a manner known per se by means of appropriate separation methods. Diastereomeric mixtures for example may be separated into their individual diastereomers by means of fractionated crystallization, chromatography, solvent distribution, and similar procedures. This separation may take place either at the level of one of the starting compounds or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

Intermediates and final products can be worked up and/or purified according to standard methods, e.g. using chromatographic methods, distribution methods, (re-) crystallization, and the like.

Starting Materials

Starting Materials, including intermediates, for compounds of the formula I, such as the compounds of the formulae II and III, can be prepared, for example, according to methods that are known in the art, according to methods described in the examples or methods analogous to those described in the examples, and/or they are known or commercially available.

In the subsequent description of starting materials and intermediates and their synthesis, R1, R2, R3, R4, R5, R6, R7, R8, X, Y, Z and Q have the meanings given above or in the Examples for the respective starting materials or intermediates, if not indicated otherwise directly or by the context. Protecting groups, if not specifically mentioned, can be introduced and removed at appropriate steps in order to prevent functional groups, the reaction of which is not desired in the corresponding reaction step or steps, employing protecting groups, methods for their introduction and their removal are as described above or below, e.g. in the references mentioned under "General Process Conditions". The person skilled in the art will readily be able to decide whether and which protecting groups are useful or required.

A starting material of the formula II may be prepared, for example, from a corresponding ester (which, if it is an active ester, may be used directly as a reactive derivative of a compound of the formula II in the process of manufacture of a compound of the formula I) of the formula V,

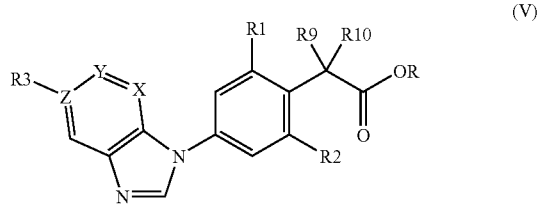

(V)

wherein R is the rest of an alcohol, e.g. alkyl or phenyl-lower alkyl, such as methyl, ethyl or benzyl, by hydrolysis, e.g. in the presence of bases, such as an alkali metal hydroxide, e.g. lithium hydroxide, in an appropriate solvent, such as an ether, e.g. tetrahydrofurane, at customary temperatures, e.g. from 20 to 50° C., or in the presence of acids, such as hydrohalic acids, e.g. hydrochloric acid, in an appropriate solvent, such as water, at customary temperatures, e.g. from 50° C. to the reflux temperature of the reaction mixture.

A compound of the formula V can, for example, be prepared from an amino compound of the formula VI,

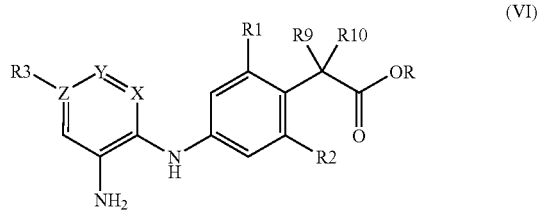

(VI)

wherein R is as defined for a compound of the formula V, by reaction with an appropriate form of formic acid, especially tri-lower alkyl orthoformate, such as triethyl orthoformate, preferably at elevated temperatures, e.g. under reflux conditions, and in the presence or preferably the absence of an appropriate solvent.

An amino compound of the formula VI may, for example, be prepared by reducing a corresponding nitro precursor compound of the formula VII,

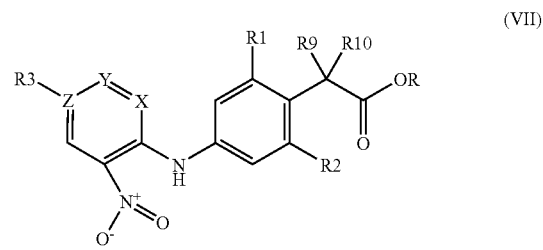

(VII)

wherein R is as defined for a compound of the formula V, preferably by catalytic hydrogenation, e.g. with hydrogen in the presence of a Raney catalyst, such as Raney nickel, in an appropriate solvent, such as an alcohol, e.g. methanol, at customary temperatures, e.g. from 0 to 50° C.

A nitro compound of the formula VII may, for example, be prepared by reacting a halo compound of the formula VIII,

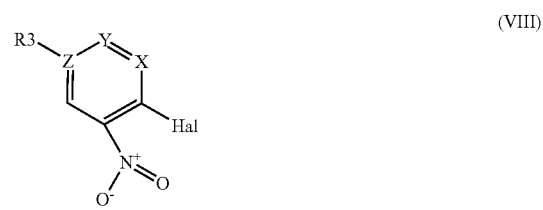

(VIII)

wherein Hal is halo, especially fluoro, chloro or bromo, under substitution conditions with an amine of the formula IX,

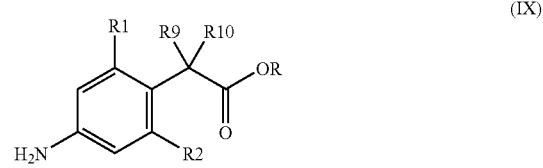

(IX)

wherein R is as defined for a compound of the formula V, under appropriate conditions—e.g., where Z is N and each of Y and X is CH and Hal is chloro or bromo in a compound of the formula VIII, at preferably elevated temperatures, e.g. from 30° C. to the reflux temperature of the reaction mixture, in an appropriate solvent, such as an alcohol and/or an ether, e.g. methanol and/or dioxane; in the case where X in a compound of the formula VIII is N, Y is CH and Z is C, in the presence or (especially if R2 is halo) absence of an acid, such as hydrochloric acid, in an appropriate solvent, such as an alcohol and/or an ether, e.g. methanol and/or dioxane, preferably at elevated temperatures, e.g. from 30° C. to the reflux temperature of the reaction mixture; or where X and Y are CH and Z is C and Hal is F in a compound of the formula VIII, in the presence or preferably absence of an appropriate solvent at elevated temperatures, e.g. in a sealed tube at 100 to 150° C.; or using appropriate variations of these reaction conditions. A compound of the formula VII may also be prepared as described in WO 97/21665 which, especially regarding this synthesis, is preferably included herein by reference.

Starting materials of the formula III can be prepared by or in analogy to methods that are described in the literature, e.g. in WO 03/099771 or WO 00/09495 which, especially regarding the manufacture of such starting materials, are preferably incorporated herein by reference.

Starting materials of the formula III wherein Q is a moiety of the formula (A) given above wherein R4 is unsubstituted or substituted aryl, unsubstituted or substituted cycloalkyl, unsubstituted or substituted heterocyclyl, unsubstituted or substituted alkyl, unsubstituted or substituted alkenyl or unsubstituted or substituted alkynyl can be prepared under common coupling conditions, e.g. under Suzuki coupling conditions. For example, a compound of the formula X,

R4-BA$_2$ (X)

wherein R4 is as just defined, especially unsubstituted or substituted aryl, and BA$_2$ is B(OD)$_2$ wherein D is hydrogen or lower alkyl, 9-borabicyclo[3.3.1]nonanyl or B(CHCH$_3$CH(CH$_3$)$_2$)$_2$, can be reacted in the presence of an appropriate catalyst, e.g. Pd(PPh$_3$)$_4$ or PdCl$_2$(dppf), in the presence of a base, e.g. an alkali metal carbonate, such as sodium carbonate, an alkali metal alcoholate, e.g. sodium ethanolate, a hydroxide, such as TlOH, a tertiary amine, such as triethylamine, or an alkali metal phosphate, such as potassium phosphate, in an appropriate solvent, such as toluene and/or water, preferably at elevated temperatures, e.g. under reflux conditions, with a compound of the formula XI,

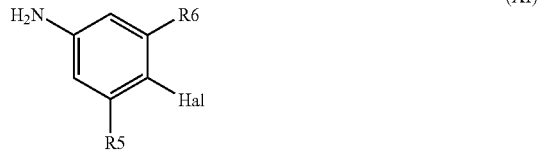

(XI)

wherein Hal is halo, especially bromo; this results in a compound of the formula XII,

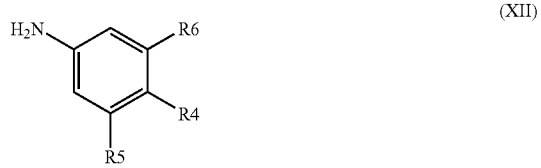

(XII)

wherein R4 is as described for a compound of the formula X, which is a compound of the formula III.

A compound of the formula III wherein Q is a moiety of the formula (A) given above wherein R5 is unsubstituted or substituted aryl or unsubstituted or substituted heterocyclyl, can be prepared under common coupling conditions, e.g. under Suzuki coupling conditions, e.g. as just described for the reaction of a compound of the formula X with a compound of the formula XI, by reaction of a compound of the formula XIII,

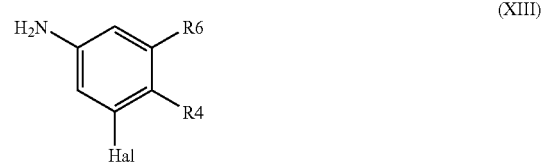

(XIII)

wherein Hal is halo, especially bromo, and R4 is as described for a compound of the formula I, preferably is hydrogen, with a compound of the formula XIV,

R5-BA$_2$ (XIV)

wherein R5 is as just described and BA$_2$ is as described for a compound of the formula X.

A compound of the formula III wherein Q is a moiety of the formula (A) wherein R4 is unsubstituted or substituted amino can e.g. be prepared from a compound of the formula XV,

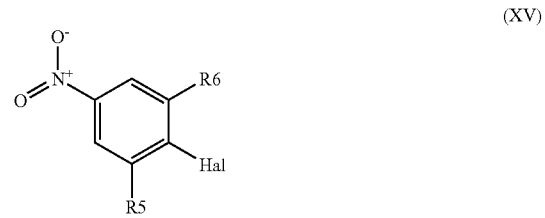

(XV)

wherein Hal is halo, especially bromo, with an amino compound of the formula XVI,

H—R$_4$* (XVI)

wherein R$_4$* is unsubstituted or (preferably) substituted amino, in the presence of preferably absence of an appropriate solvent, preferably at elevated temperatures, e.g. from 100 to 150° C., e.g. in a sealed tube, resulting in a compound of the formula XVII,

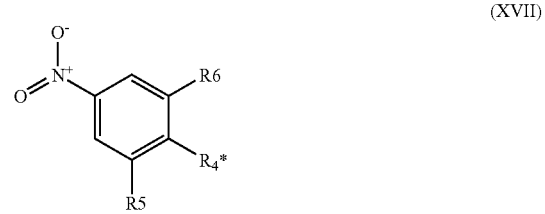

(XVII)

wherein R$_4$* is as described for a compound of the formula XVI; the nitro group in this compound can then be reduced to amino to give a corresponding amino compound of the formula III, e.g. by catalytic hydrogenation, for example in the presence of hydrogen and a hydrogenation catalyst, e.g. a Raney catalyst, such as Raney-Ni, or a noble metal catalyst, e.g. palladium, preferably on a carrier, such as charcoal, in an appropriate solvent, e.g. an alcohol, such as methanol or ethanol, at temperatures e.g. from 0 to 50° C.

A compound of the formula XI (which also falls under a compound of the formula III) wherein Hal is halo, especially iodo, may, for example, be prepared by reducing the nitro group in a nitro compound of the formula XVIII,

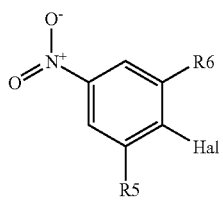

(XVIII)

wherein Hal is halo, especially iodo, to the amino group, e.g. under conditions as described for the hydrogenation of a compound of the formula XVII. A compound of the formula XVIII (e.g. wherein R5 is trifluoromethyl, Hal is iodo and R6 is hydrogen) may, for example, be obtained as or in analogy to the method described in WO 00/09495 which is, especially with regard to this synthesis, preferably incorporated herein by reference.

Other starting materials, e.g. those of the formula VIII, IX, X, XI, XIII, XIV, XVI and XVIII, are known in the art, commercially available and/or can be prepared according to known or standard procedures, e.g. in analogy to or by methods described in the Examples.

General Process Conditions

The following applies in general to all processes mentioned hereinbefore and hereinafter, while reaction conditions specifically mentioned above or below are preferred:

In any of the reactions mentioned hereinbefore and hereinafter, protecting groups may be used where appropriate or desired, even if this is not mentioned specifically, to protect functional groups that are not intended to take part in a given reaction, and they can be introduced and/or removed at appropriate or desired stages. Reactions comprising the use of protecting groups are therefore included as possible wherever reactions without specific mentioning of protection and/or deprotection are described in this specification.

Within the scope of this disclosure only a readily removable group that is not a constituent of the particular desired end product of formula I is designated a "protecting group", unless the context indicates otherwise. The protection of functional groups by such protecting groups, the protecting groups themselves, and the reactions appropriate for their removal are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (Methods of Organic Chemistry), Houben Weyl, 4th edition, Volume 15/I, Georg Thieme Verlag, Stuttgart 1974, in H.-D. Jakubke and H. Jeschkeit, "Aminosauren, Peptide, Proteine" (Amino acids, Peptides, Proteins), Verlag Chemie, Weinheim, Deerfield Beach, and Basel 1982, and in Jochen Lehmann, "Chemie der Kohlenhydrate: Monosaccharide und Derivate" (Chemistry of Carbohydrates: Monosaccharides and Derivatives), Georg Thieme Verlag, Stuttgart 1974. A characteristic of protecting groups is that they can be removed readily (i.e. without the occurrence of undesired secondary reactions) for example by solvolysis, reduction, photolysis or alternatively under physiological conditions (e.g. by enzymatic cleavage).

All the above-mentioned process steps can be carried out under reaction conditions that are known per se, preferably those mentioned specifically, in the absence or, customarily, in the presence of solvents or diluents, preferably solvents or diluents that are inert towards the reagents used and dissolve them, in the absence or presence of catalysts, condensation or neutralizing agents, for example ion exchangers, such as cation exchangers, e.g. in the $H^+$ form, depending on the nature of the reaction and/or of the reactants at reduced, normal or elevated temperature, for example in a temperature range of from about −100° C. to about 190° C., preferably from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofurane or dioxane, liquid aromatic hydrocarbons, such as benzene or toluene, alcohols, such as methanol, ethanol or 1- or 2-propanol, nitriles, such as acetonitrile, halogenated hydrocarbons, e.g. as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, or mixtures of these, for example aqueous solutions, unless otherwise indicated in the description of the processes. Such solvent mixtures may also be used in working up, for example by chromatography or partitioning.

Intermediates and final products can be worked up and/or purified according to standard methods, e.g. using chromatographic methods, distribution methods, (re-) crystallization, distillation (under normal or reduced pressure), steam distillation and the like.

The invention relates also to those forms of the process in which a compound obtainable as intermediate at any stage of the process is used as starting material and the remaining process steps are carried out, or in which a starting material is formed under the reaction conditions or is used in the form of a derivative, for example in protected form or in the form of a salt, or a compound obtainable by the process according to the invention is produced under the process conditions and processed further in situ. In the process of the present invention those starting materials are preferably used which result in compounds of formula I described as being preferred. Special preference is given to reaction conditions that are identical or analogous to those mentioned in the Examples. The invention also relates to novel intermediates as well as salts thereof where salt-forming groups are present, as well as their synthesis.

PREFERRED EMBODIMENTS ACCORDING TO THE INVENTION

In the following preferred embodiments as well as in preceding and following embodiments of more general scope, any one or more or all general expressions can be replaced by the corresponding more specific definitions provided above and below, thus yielding stronger preferred embodiments of the invention.

The invention relates in particular to a compound of the formula I wherein each of R1 and R2, independently of the other, is selected from the group consisting of hydrogen, halo and $C_1$-$C_7$-alkyl;

R3 is absent if Z is nitrogen or, if Z is C (carbon), is hydrogen, unsubstituted or substituted aryl or unsubstituted or substituted heterocyclyl;

R9 and R10 both represent hydrogen; and

X is N (nitrogen) or CH (hydrogen-substituted carbon),

Y is CH or N,

Z is C or N, and

Q is a moiety of the formula (A) wherein
  R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;
  R5 is hydrogen, unsubstituted or substituted aryl or unsubstituted or substituted heterocyclyl; and
  R6 is unsubstituted or substituted cycloalkyl or unsubstituted or (preferably) substituted alkyl;
or a moiety of the formula (B) wherein
  R7 is unsubstituted or substituted aryl or substituted heterocyclyl and
  R8 is alkyl or cycloalkyl;
where the asterisk * in formulae (A) and (B) marks the bond through which the moiety is bound to the NH of the amide group in formula I.

The invention relates especially to a compound of the formula I wherein each of R1 and R2, independently of the other, is selected from the group consisting of hydrogen, halo and $C_1$-$C_7$-alkyl;

R3 is absent if Z is nitrogen or, if Z is C (carbon), is hydrogen or unsubstituted or substituted aryl;

R9 and R10 both represent hydrogen,

X is N or CH,

Y is CH,

Z is C or N, and

Q is a moiety of the formula (A)
  wherein R4 is hydrogen, halo, unsubstituted or substituted amino, unsubstituted or substituted aryl, unsubstituted or substituted alkyl or unsubstituted or substituted alkynyl;
  R5 is hydrogen or unsubstituted or substituted aryl; and
  R6 is unsubstituted or preferably substituted alkyl;
or a moiety of the formula (B)
  wherein
  R7 is unsubstituted or substituted aryl and
  R8 is alkyl;
or a (preferably pharmaceutically acceptable) salt thereof.

The invention highly preferably relates to a compound of the formula I, wherein

R1 is hydrogen, halo, especially chloro, or $C_1$-$C_7$-alkyl,

R2 is hydrogen, halo, especially chloro, or $C_1$-$C_7$-alkyl,

R3 is absent if Z is nitrogen or, if Z is C (carbon), is hydrogen, phenyl that is unsubstituted or substituted by one or more, e.g. up to three, moieties independently selected from $C_1$-$C_7$-alkyl, e.g. methyl, halo, e.g. chloro or bromo, hydroxy, $C_1$-$C_7$-alkoxy, e.g. methoxy, and cyano, preferably by up to three $C_1$-$C_7$-alkoxy moieties, R9 and R10 both represent hydrogen, X is N or CH, Y is CH, Z is C or N, Q is a moiety of the formula (A) wherein R4 is hydrogen, halogen, especially iodo, phenyl that is unsubstituted or substituted by one or more, e.g. up to three, moieties independently selected from $C_1$-$C_7$-alkyl, e.g. methyl, halo, e.g. chloro or bromo, hydroxy, $C_1$-$C_7$-alkoxy, e.g. methoxy, and cyano; N,N-di-($C_1$-$C_7$ alkyl)-amino-$C_1$-$C_7$-alkyl, especially N,N-dimethylaminomethyl or N,N-diethylaminomethyl, N—[(N-mono- or N,N-di-($C_1$-$C_7$-alkyl)-amino)-$C_1$-$C_7$-alkyl]-N—$C_1$-$C_7$-alkylamino, such as N-3-[N—(N,N-dimethylamino)-propyl-N-methyl-amino, N-2-[N—(N,N-dimethylamino)-ethyl-N-methyl-amino or N—(N,N-dimethylamino)-methyl-N-methyl-amino, pyrrolidino, piperidino, piperazino, 4-$C_1$-$C_7$-alkylpiperazino, 1-$C_1$-$C_7$-alkylpiperidin-4-yl, morpholino, thiomorpholino, pyrrolidino-$C_1$-$C_7$-alkyl, such as pyrrolidinomethyl, piperidino-$C_1$-$C_7$-alkyl, such as piperidinomethyl, piperazino-$C_1$-$C_7$-alkyl, 4-$C_1$-$C_7$-alkylpiperazino-$C_1$-$C_7$-alkyl, such as 4-methyl-, 4-ethyl- or 4-isopropyl-piperazino-$C_1$-$C_7$-alkyl, morpholino-$C_1$-$C_7$-alkyl, thiomorpholino-$C_1$-$C_7$-alkyl, N-piperidin-(2, 3 or preferably 4)-yl-amino, N—$C_1$-$C_7$-alkyl-N-piperidinylamino wherein piperidinyl is bound via a ring carbon and is unsubstituted or substituted by lower alkyl, e.g. e.g. N-lower alkyl-N-(1-lower alkylpiperidin-(2, 3 or preferably 4)-yl)-amino, or N,N-di-(lower alkyl, phenyl and/or phenyl lower alkyl)-$C_3$-$C_7$-alkynyl, such as 3-(N,N-dimethylamino)-prop-1-ynyl;

R5 is hydrogen or phenyl that is unsubstituted or substituted by one or more, e.g. up to three, moieties independently selected from $C_1$-$C_7$-alkyl, e.g. methyl, halo, e.g. chloro or bromo, hydroxy, $C_1$-$C_7$-alkoxy, e.g. methoxy, and cyano; and R6 is $C_1$-$C_7$-alkyl, $C_3$-$C_8$-cycloalkyl or especially halo-$C_1$-$C_7$-alkyl, preferably trifluoromethyl, or a moiety of the formula (B) wherein R7 is phenyl that is unsubstituted or substituted by one or more, e.g. up to three, moieties independently selected from $C_1$-$C_7$-alkyl, e.g. methyl, halo, e.g. chloro or bromo, hydroxy, $C_1$-$C_7$-alkoxy, e.g. methoxy, and cyano; and R8 is $C_3$-$C_8$-cycloalkyl or especially $C_1$-$C_7$-alkyl, preferably isobutyl;

or a (preferably pharmaceutically acceptable) salt thereof.

Very especially, the invention relates to a compound of the formula I wherein

The invention highly preferably relates to a compound of the formula I, wherein

R1 is hydrogen,

R2 is hydrogen or halo, especially chloro,

R3 is absent if Z is nitrogen or, if Z is C, is hydrogen, phenyl that is unsubstituted or substituted by $C_1$-$C_7$-alkoxy, e.g. methoxy, R9 and R10 both represent hydrogen, X is N or CH, Y is CH, Z is C or N, Q is a moiety of the formula (A) wherein R4 is hydrogen, halogen, especially iodo, phenyl that is unsubstituted or substituted by halo, e.g. chloro or bromo, or cyano; N—[(N-mono- or N,N-di-($C_1$-$C_7$-alkyl)-amino)-$C_1$-$C_7$-alkyl]-N—$C_1$-$C_7$-alkylamino, such as N-3-[N—(N,N-dimethylamino)-propyl-N-methyl-amino, N-2-[N—(N,N-dimethylamino)-ethyl-N-methyl-amino or N—(N,N-dimethylamino)-methyl-N-methyl-amino, pyrrolidino-$C_1$-$C_7$-alkyl, such as pyrrolidinomethyl, piperidino-$C_1$-$C_7$-alkyl, such as piperidinomethyl, piperazino-$C_1$-$C_7$-alkyl, 4-$C_1$-$C_7$-alkylpiperazino-$C_1$-$C_7$-alkyl, such as 4-methyl-, 4-ethyl- or 4-isopropyl-piperazino-$C_1$-$C_7$- alkyl, N—$C_1$-$C_7$-alkyl-N-piperidin-ylamino wherein piperidinyl is bound via a ring carbon and is unsubstituted or substituted by lower alkyl, e.g. N-lower alkyl-N-(1-lower alkylpiperidin-(2, 3 or preferably 4)-yl)-amino, or N,N-di-(lower alkyl, phenyl and/or phenyl lower alkyl)-$C_3$-$C_7$-alkynyl, such as 3-(N,N-dimethylamino)-prop-1-ynyl;

R5 is hydrogen, and

R6 is halo-$C_1$-$C_7$-alkyl, preferably trifluoromethyl, or a moiety of the formula (B) wherein R7 is phenyl that is unsubstituted or substituted by $C_1$-$C_7$-alkyl, e.g. methyl; and R8 is $C_1$-$C_7$-alkyl, preferably isobutyl;

or a (preferably pharmaceutically acceptable) salt thereof.

A further embodiment of the present invention preferably pertains to a compound of the formula I wherein each of R1 and R2, independently of the other, is selected from the group consisting of hydrogen, halo and $C_1$-$C_7$-alkyl;

R3 is absent if Z is nitrogen or, if Z is C (carbon), is hydrogen or unsubstituted or substituted aryl;

X is N (nitrogen) or CH (hydrogen-substituted carbon),

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen, unsubstituted or substituted cycloalkyl or unsubstituted or (preferably) substituted alkyl;

or a moiety of the formula (B) wherein

R7 is unsubstituted or substituted aryl or unsubstituted or substituted heterocyclyl and R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2- or —CH2-CH2-, R2 is selected from the group consisting of hydrogen, halo and $C_1$-$C_7$-alkyl, and R10 represents hydrogen;

or a salt thereof.

In such embodiment, compounds of formula I are preferred, wherein each of R1 and R2, independently of the other, is selected from the group consisting of hydrogen, halo and $C_1$-$C_7$-alkyl;

R3 is absent if Z is nitrogen or, if Z is C (carbon), is hydrogen or unsubstituted or substituted aryl;

X is N (nitrogen) or CH (hydrogen-substituted carbon),

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted alkyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen or substituted alkyl;

or a moiety of the formula (B) wherein

R7 is unsubstituted or substituted aryl and

R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2- or —CH2-CH2-, R2 is selected from the group consisting of hydrogen, halo and $C_1$-$C_7$-alkyl, and R10 represents hydrogen.

In such embodiment, compounds of formula I are even more preferred, wherein each of R1 and R2, independently of the other, is selected from the group consisting of hydrogen, halo and $C_1$-$C_7$-alkyl;

R3 is absent if Z is nitrogen or, if Z is C (carbon), is hydrogen or unsubstituted or substituted aryl;

X is N (nitrogen) or CH (hydrogen-substituted carbon),

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted alkyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen or substituted alkyl;

or a moiety of the formula (B) wherein

R7 is unsubstituted or substituted aryl and

R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2- or —CH2-CH2-, R2 is selected from the group consisting of hydrogen, halo and $C_1$-$C_7$-alkyl, and R10 represents hydrogen.

In addition to the foregoing, in formula I the following significances are preferred independently, collectively or in any combination or sub-combination:

(a) Y is preferably CH;

(b) R1 is preferably hydrogen or halo, preferably chloro, or together with R9 forms a group —C(O)—CH2- or —CH2-CH2-;

(c) R2 is preferably hydrogen, halo, preferably chloro, or $C_{1-4}$-alkyl, preferably methyl;

(d) R3 is preferably absent, lower alkoxy phenyl or hydrogen, most preferably hydrogen;

(e) R4 is preferably hydrogen, halogen, especially fluoro or iodo, phenyl that is unsubstituted or substituted by halo, e.g. chloro or bromo, or cyano; N,N-di-($C_1$-$C_7$-alkyl)-amino)-$C_1$-$C_7$-alkyl; N—[(N-mono- or N,N-di-($C_1$-$C_7$- alkyl)-amino)-$C_1$-$C_7$-alkyl]-N—$C_1$-$C_7$-alkylamino, such as N-3-[N—(N,N-dimethylamino)-propyl-N-methylamino, N-2-[N—(N,N-dimethylamino)-ethyl-N-methylamino or N—(N,N-dimethylamino)-methyl-N-methylamino, pyrrolidino-$C_1$-$C_7$-alkyl, such as pyrrolidinomethyl, piperidino-$C_1$-$C_7$-alkyl, such as piperidinomethyl, piperazino-$C_1$-$C_7$-alkyl, 4-$C_1$-$C_7$-alkylpiperazino-$C_1$-$C_7$-alkyl, such as 4-methyl-, 4-ethyl- or 4-isopropyl-piperazino-$C_1$-$C_7$-alkyl, N—$C_1$-$C_7$-alkyl-N-piperidin-ylamino wherein piperidinyl is bound via a ring carbon and is unsubstituted or substituted by lower alkyl, e.g. N-lower alkyl-N-(1-lower alkylpiperidin-(2, 3 or preferably 4)-yl)-amino, 4-$C_1$-$C_7$-alkylpiperazino-, or N,N-di-(lower alkyl, phenyl and/or phenyl lower alkyl)-$C_3$-$C_7$-alkynyl, such as 3-(N,N-dimethylamino)-prop-1-ynyl;

(f) R5 is preferably hydrogen, lower alkoxy phenyl, 4-$C_1$-$C_7$-alkylpiperazino, N,N-di-($C_1$-$C_7$-alkyl)-amino)-$C_1$-$C_7$-alkyl, pyrrolidino-$C_1$-$C_7$-alkyl, such as pyrrolidinomethyl, imidazolyl, 2-$C_1$-$C_7$-alkyl imidazolyl, 2,4-di($C_1$-$C_7$-alkyl) imidazolyl, 4-$C_1$-$C_7$-alkylpiperazino-$C_1$-$C_7$-alkyl; more preferably hydrogen;

(g) R6 is preferably trifluoromethyl or hydrogen;

(h) R7 is preferably phenyl being optionally mono- or di-substituted by $C_1$-$C_4$-alkoxy, $C_1$-$C_4$-alkyl, trifluoromethyl, halo, especially fluoro or chloro, morpholinyl $C_1$-$C_4$-alkyl, di-($C_1$-$C_4$-alkyl)amino $C_1$-$C_4$-alkyl or $C_1$-$C_4$-alkyl piperazinyl $C_1$-$C_4$-alkyl;

(i) R8 is preferably $C_1$-$C_7$-alkyl, more preferably methyl or tert-butyl, or $C_3$-$C_4$-cycloalkyl;

(j) R9 is preferably hydrogen, $C_{1-4}$-alkyl, preferably methyl, hydroxyl, together with R1 forms a group —C(O)—CH2- or —CH2CH2-, or together with R10 represents oxo, and (k) R10 is preferably hydrogen or $C_{1-4}$-alkyl, preferably methyl, or together with R9 represents oxo.

Especially preferred are the compounds of the formula I, or the (especially pharmaceutically acceptable) salts thereof, novel starting materials and novel processes mentioned in the examples.

Pharmaceutical Compositions

The invention relates also to pharmaceutical compositions comprising a compound of formula I, to the use of a compound of the formula I in the therapeutic (in a broader aspect of the invention also prophylactic) treatment or a method of treatment of a disease or disorder that depends on (especially inappropriate) or protein kinase activity or responds to modulabon, especially inhibition, of such a protein kinase, especially the disorders or diseases mentioned as preferred above, to the compounds for said use and to pharmaceutical preparations and their manufacture, especially for said uses. More generally, pharmaceutical preparations are useful in case of compounds of the formula I, which may also be present in the form of their (especially pharmaceutically acceptable) salts, and are thus an embodiment of the invention.

The pharmacologically active compounds of the formula I may be present in or employed, for example, for the preparation of pharmaceutical compositions that comprise an effective amount of a compound of the formula I, or a pharmaceutically acceptable salt thereof, as active ingredient together or in admixture with one or more (e.g. inorganic or organic, solid or liquid) pharmaceutically acceptable carriers (carrier materials).

The invention relates also to a pharmaceutical composition that is suitable for administration to a warm-blooded animal, especially a human (or to cells or cell lines derived from a warm-blooded animal, especially a human, e.g. lymphocytes), for the treatment (this, in a broader aspect of the invention, also including prevention of (=prophylaxis against)) a disease that responds to inhibition of protein kinase activity, comprising a compound of formula I or a pharmaceutically acceptable salt thereof, preferably in an amount which is effective against said disease, together with at least one pharmaceutically acceptable carrier.

The pharmaceutical compositions according to the invention are those for enteral, such as nasal, rectal or oral, or parenteral, such as intraarticular, intramuscular or intravenous, administration to warm-blooded animals (especially a human), that comprise a pharmaceutically effective dose of the pharmacologically active ingredient, alone or together with a significant amount of a pharmaceutically acceptable carrier. The dose of the active ingredient depends on the species of warm-blooded animal, the body weight, the age and the individual condition, individual pharmacokinetic data, the disease to be treated and the mode of administration.

The invention relates also to method of treatment for a disease that responds to inhibition of a disease that depends on (especially inappropriate) activity of a protein kinase; which comprises administering a prophylactically or especially therapeutically effective amount of a compound of formula I, or a pharmaceutically acceptable salt thereof, to an animal, especially to a warm-blooded animal, for example a human, that, on account of one or more of the mentioned diseases, is in need of such treatment.

The dose of a compound of the formula I or a pharmaceutically acceptable salt thereof to be administered to warm-blooded animals, for example humans of approximately 70 kg body weight, preferably is from approximately 3 mg to approximately 10 g, more preferably from approximately 10 mg to approximately 1.5 g, most preferably from about 100 mg to about 1000 mg/person/day, divided preferably into 1-3 single doses which may, for example, be of the same size. Usually, children receive half of the adult dose.

The pharmaceutical compositions comprise from approximately 1% to approximately 96%, preferably from approximately 20% to approximately 95%, active ingredient. Pharmaceutical compositions according to the invention may be, for example, in unit dosage form, such as in the form of ampoules, vials, suppositories, dragees, tablets or capsules.

The pharmaceutical compositions of the present invention are prepared in a manner known per se, for example by means of conventional dissolving, lyophilizing, mixing, granulating or confectioning processes.

Solutions of the active ingredient, and also suspensions, and especially isotonic aqueous solutions or suspensions, are preferably used, it being possible, for example in the case of lyophilized compositions that comprise the active ingredient alone or together with a carrier, for example mannitol, for such solutions or suspensions to be produced prior to use. The pharmaceutical compositions may be sterilized and/or may comprise excipients, for example preservatives, stabilizers, wetting and/or emulsifying agents, solubilizers, salts for regulating the osmotic pressure and/or buffers, and are prepared in a manner known per se, for example by means of conventional dissolving or lyophilizing processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8-22, especially from 12-22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brasidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydroxy, for example a mono-, di- or tri-hydroxy, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of C8 to C12, Hüls AG, Germany), but especially vegetable oils, such as cottonseed oil, almond oil, olive oil, castor oil, sesame oil, soybean oil and groundnut oil.

The injection or infusion compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into plastics carriers that allow the active ingredients to diffuse or be released in measured amounts.

Suitable carriers are especially fillers, such as sugars, for example lactose, saccharose, mannitol or sorbitol, cellulose preparations and/or calcium phosphates, for example tri-calcium phosphate or calcium hydrogen phosphate, and binders, such as starch pastes using for example corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, and/or carboxymethyl starch, crosslinked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragee cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and soft sealed capsules made of gelatin and a plasticizer, such as glycerol or sorbitol. The dry-filled capsules may comprise the active ingredient in the form of granules, for example with fillers, such as lactose, binders, such as starches, and/or glidants, such as talc or magnesium stearate, and if desired with stabilizers. In soft capsules the active ingredient is preferably dissolved or suspended in suitable oily excipients, such as fatty oils, paraffin oil or liquid polyethylene glycols, it being possible also for stabilizers and/or antibacterial agents to be added. Dyes or pigments may be added to the tablets or dragee coatings or the capsule casings, for example for identification purposes or to indicate different doses of active ingredient.

A compound of the formula I may also be used to advantage in combination with other anti-proliferative agents. Such antiproliferative agents include, but are not limited to aromatase inhibitors; antiestrogens; topoisomerase I inhibitors; topoisomerase II inhibitors; microtubule active agents; alkylating agents; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; agents used in the treatment of hematologic malignancies; compounds which target, decrease or inhibit the activity of Flt-3; Hsp90 inhibitors; and temozolomide (TEMODAL®).

For the treatment of acute myeloid leukemia (AML), compounds of formula I can be used in combination with standard leukemia therapies, especially in combination with therapies used for the treatment of AML. In particular, compounds of formula I can be administered in combination with e.g. farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The structure of the active agents identified by code nos., generic or trade names may be taken from the actual edition of the standard compendium "The Merck Index" or from databases, e.g. Patents International (e.g. IMS World Publications).

The above-mentioned compounds, which can be used in combination with a compound of the formula I, can be prepared and administered as described in the art such as in the documents cited above.

A compound of the formula I may also be used to advantage in combination with known therapeutic processes, e.g., the administration of hormones or especially radiation.

A compound of formula I may in particular be used as a radiosensitizer, especially for the treatment of tumors which exhibit poor sensitivity to radiotherapy.

By "combination", there is meant either a fixed combination in one dosage unit form, or a kit of parts for the combined administration where a compound of the formula I and a combination partner may be administered independently at the same time or separately within time intervals that especially allow that the combination partners show a cooperative, e.g. synergistic, effect, or by making use of administration schedules representing any combination thereof. For example, combinations may also be present in the form of a kit of parts, that is, a product that allows for the simultaneous, sequential and/or independent administration of at least one compound of the formula I and one or more other combinations partners, e.g. selected from the antiproliferative agents mentioned above.

The following Examples serve to illustrate the invention without limiting the scope thereof.

Temperatures are measured in degrees Celsius. Unless otherwise indicated, the reactions take place at rt.

TLC conditions: The $R_f$ values which indicate the ratio of the distance moved by each substance to the distance moved by the eluent front are determined on silica gel thin-layer plates 5×10 cm TLC plates, silica gel $F_{254}$ (Merck, Darmstadt, Germany) by thin-layer chromatography using the solvent systems indicated below.

Analytical HPLC Conditions:
System 1
Linear gradient 20-100% CH$_3$CN in 5 min+1.5 min 100% CH$_3$CN (0.1% TFA); detection at 215 nm, flow rate 1 mL/min at 30° C. Column: Nucleosil 100-3 C18 (70×4.0 mm)
System 2
Linear gradient 5-95% CH$_3$CN in 2.20 min+0.5 min 95% CH$_3$CN (0.1% TFA); detection at 215 nm, flow rate 2 mL/min at 35° C. Column: Sun Fire (waters) 3.5 µm C18 (3.0×20 mm)
System 3
Linear gradient 5-100% CH$_3$CN in 8 min+1.8 min 100% CH$_3$CN (0.1% HCOOH); detection at 215 nm, flow rate 2 mL/min at 40° C. Column: XERRA-MS (waters) 5 µm C18 (50×4.6 mm)
System 4
Linear gradient 20-100% CH$_3$CN in 5 min+1 min 100% CH$_3$CN (0.1% TFA); detection at 215 nm, flow rate 1 mL/min at 30° C. Column: Nudeosil 100-3 C18 (70×4.0 mm)

| Abbreviations and Acronyms: | |
| --- | --- |
| ACN | acetonitrile (CH$_3$CN) |
| AcOH | acetic acid |
| brine | saturated solution of NaCl in water |
| t-Bu$_3$P | tri-tert-butylphosphine |
| conc. | Concentrated |
| CuI | copper(I) iodide |
| DCM | dichloromethane (CH$_2$Cl$_2$) |
| DIEA | Diisopropylethylamine |
| DMAP | 4-(dimethylamino)pyridine |
| DMF | dimethyl formamide |
| DMP | 1,3-dimethyl-3,4,5,6-tetrahydro-2-(1H)-pyrimidinone |
| DMSO | dimethylsulfoxide |
| equiv | equivalent(s) |
| Et$_3$N | triethylamine |
| Et$_2$NH | diethylamine |
| Et$_2$O | diethylether |
| EtOAc | ethyl acetate |
| EtOH | ethanol |
| h | hour(s) |
| HPLC | high pressure liquid chromatography |
| L | liter(s) |
| Me | methyl |
| MeOH | methanol |
| mL | milliliter(s) |
| min | minute(s) |
| MPLC | medium pressure liquid chromatography |
| MS | mass spectrum |
| NMR | Nuclear Magnetic Resonance |
| NMP | 1-methyl-2-pyrrolidone |
| PdCl$_2$(dppf)$_2$ | [1,1'-bis(diphenylphosphino)ferrocene]dichloropalladium(II) |
| Pd(PhCN)$_2$Cl$_2$ | bis(benzonitrile)palladium(II) chloride |
| Pd(PPh$_3$)$_4$ | tetrakis(triphenylphosphine)palladium(0) |
| Ph | phenyl |
| i-Pr$_2$NH | diisopropylamine |
| R$_f$ | ratio of fronts (TLC) |
| rt | room temperature |
| TBTU | O-(Benzotriazol-1-yl)-N,N,N',N'-tetramethyluronium tetrafluoroborate |
| THF | tetrahydrofuran |
| TLC | thin layer chromatography |
| t$_R$ | retention time (HPLC) |

| Trademarks | |
| --- | --- |
| Celite = | Celite ® (The Celite Corporation) = filtering aid based on diatomaceous earth |
| Nucleosil = | Nucleosil ®, trademark of Machery & Nagel, Düren, FRG for HPLC materials |

EXAMPLE 1

2-(4-Imidazo[4,5-c]pyridin-1-yl-phenyl)-N-(3-trifluoromethyl-phenyl)-acetamide

DIEA (0.15 mL, 0.87 mmol, 4.0 equiv) is added dropwise to a cold (0° C.) mixture of crude (4-imidazo[4,5-c]pyridin-1-yl-phenyl)-acetic acid (55 mg, 0.22 mmol), 3-aminobenzotrifluoride (39 mg, 0.24 mmol, 1.1 equiv), and TBTU (77 mg, 0.24 mmol, 1.1 equiv) in DMF (0.5 mL). The reaction mixture is allowed to warm to rt, stirred for 2 h, diluted with EtOAc and washed with a saturated aqueous solution of NaHCO$_3$, H$_2$O, and brine. The organic phase is dried (Na$_2$SO$_4$), filtered and concentrated in vacuo. The residue is purified by silica gel column chromatography (CH$_2$Cl$_2$/MeOH, 94:6) to afford the title compound as a white solid: ES-MS: 397.0 [M+H]$^+$; single peak at t$_R$=3.52 min (System 1); R$_f$=0.18 (CH$_2$Cl$_2$/MeOH, 94:6).

The starting material is prepared as follows:

Step 1.1:
(4-Imidazo[4,5-c]pyridin-1-yl-phenyl)-acetic acid

A mixture of (4-imidazo[4,5-c]pyridin-1-yl-phenyl)-acetic acid methyl ester (0.349 g, 1.31 mmol) and a 6 N aqueous solution of HCl (3.5 mL) is stirred and refluxed for 3 h. The mixture is allowed to cool to rt and concentrated in vacuo to provide the hydrochloric acid salt of the title compound: ES-MS: 254.0 [M+H]$^+$; single peak at t$_R$=1.20 min (System 1).

Step 1.2:
(4-Imidazo[4,5-c]pyridin-1-yl-phenyl)-acetic acid methyl ester

A mixture of [4-(3-amino-pyridin-4-ylamino)-phenyl]-acetic acid methyl ester (0.356 g, 1.39 mmol) and triethyl orthoformate (9.2 mL, 55.4 mmol, 40 equiv) is stirred and refluxed for 2 h. The resulting mixture is allowed to cool to rt and concentrated in vacuo to provide the title compound as a beige solid: ES-MS: 268.1 [M+H]$^+$; single peak at t$_R$=2.03 min (System 1).

Step 1.3:
[4-(3-Amino-pyridin-4-ylamino)-phenyl]-acetic acid methyl ester

A mixture of 4-chloro-3-nitropyridine (0.500 g, 3.06 mmol) (LANCASTER) and (4-aminophenyl)-acetic acid (0.467 g 3.06 mmol) (Aldrich) in MeOH/dioxane (10 mL, 1/1 v/v) is stirred and refluxed for 6 h. The mixture is allowed to cool to rt and concentrated in vacuo to afford crude [4-(3-nitro-pyridin-4-ylamino)-phenyl]-acetic acid methyl ester. A suspension of the crude ester (0.569 g) and Raney Ni (~0.140 g) in MeOH (15 mL) is stirred for 21 h at rt, under a hydrogen atmosphere. The reaction mixture is filtered through a pad of Celite and concentrated. Trituration of the residue in CH$_2$Cl$_2$ affords the title compound as a beige solid: ES-MS: 258.0 [M+H]$^+$; single peak at t$_R$=2.54 min (System 1).

EXAMPLE 2

2-(4-Imidazo[4,5-c]pyridin-1-yl-phenyl)-N-[4-(4-methyl-piperazin-1-ylmethyl)-3-trifluoromethyl-phenyl]-acetamide The title compound is prepared as described in Example 1 but using 4-(4-methyl-piperazin-1-ylmethyl)-3-trifluorom-

EXAMPLE 3

N-(3'-Chloro-2-trifluoromethyl-biphen-4-yl)-2-(4-imidazo[4,5-c]pyridin-1-yl-phenyl)-acetamide The title compound is prepared as described in Example 1 but using 3'-chloro-2-trifluoromethyl-biphen-4-ylamine. Title compound: ES-MS: 507.2 [M]$^+$; single peak at $t_R$=4.39 min (System 1); $R_f$=0.10 (CH$_2$Cl$_2$/MeOH, 95:5).

The starting material is prepared as follows:

Step 3.1:
3'-Chloro-2-trifluoromethyl-biphenyl-4-amine

A mixture of 5-amino-2-bromobenzotrifluoride (Dakwood Products, Inc.) (500 mg, 2.1 mMol), 3-chlorophenylboronic acid (970 mg, 6.2 mMol, 3 equiv) (Aldrich), Pd(PPh$_3$)$_4$ (70 mg, 0.018 mMol, 0.03 equiv), Na$_2$CO$_3$ (2 M solution in H$_2$O, 5 mL, 10 mMol, 4.76 equiv), and toluene (14 mL) is stirred at reflux for 1 h. The reaction mixture is allowed to cool to rt and filtered through a pad of celite, washing the filter cake with CH$_2$Cl$_2$ and H$_2$O. The layers are separated and the aqueous phase is extracted with CH$_2$Cl$_2$ (2×60 mL). The combined organic phase is washed with brine, dried (Na$_2$SO$_4$), filtered and concentrated in vacuo. MPLC (CH$_3$CN/H$_2$O/TFA) purification of the crude material affords the title compound: MS: 270.0 [M-2]$^-$; HPLC $^{D}t_{Ret}$=4.9.

EXAMPLE 4

N-(3'-Bromo-2-trifluoromethyl-biphen-4-yl)-2-(4-imidazo[4,5-c]pyridin-1-yl-phenyl)-acetamide The title compound is prepared as described in Example 1 but using 3'-bromo-2-trifluoromethyl-biphen-4-ylamine (see step 3.1). Title compound: ES-MS: 552.8 [M+H]$^+$; single peak at $t_R$=4.50 min (System 1); $R_f$=0.10 (CH$_2$Cl$_2$/MeOH, 94:6).

EXAMPLE 5

N-{4-[(3-Dimethylamino-Propyl)methyl-amino]-3-trifluoromethyl-phenyl}-2-(4-imidazo[4,5-c]pyridin-1-yl-phenyl)-acetamide The title compound is prepared as described in Example 1 but using 4-[(3-dimethylamino-propyl)-methyl-amino]-3-trifluoromethyl-phenylamine. Title compound: ES-MS: 511.0 [M+H]$^+$; single peak at t_2.72 min (System 1); $R_f$=0.12 (CH$_2$Cl$_2$/MeOH+1% NH$_3^{aq}$, 9:1).

The starting material is prepared as follows:

Step 5.1: 4-[(3-Dimethylamino-propyl)-methyl-amino]-3-trifluoromethyl-phenylamine A suspension of N,N,N'-trimethyl-N'-(4-nitro-2-trifluoromethyl-phenyl)-propane-1,3-diamine (1 g, 3.28 mmol) and Raney Ni (~0.300 g) in MeOH (20 mL) is stirred for 2 h 40 min at rt, under a hydrogen atmosphere. The reaction mixture is filtered through a pad of Celite and concentrated to afford the title compound as a brown oil: ES-MS: 276.2 [M+H]$^+$; single peak at $t_R$=1.30 min (System 1).

Step 5.2: N,N,N'-Trimethyl-N'-(4-nitro-2-trifluoromethyl-phenyl)-propane-1,3-diamine A mixture of 2-bromo-5-nitrobenzotrifluoride (ALFA ACSAR) (1 g, 3.70 mmol) and N,N,N'-trimethylpropylene diamine (ALDRICH) (0.65 mL, 4.40 mmol, 1.2 equiv) is stirred in a sealed tube at 130° C. for 18 h. The reaction mixture is allowed to cool to rt, triturated with Et$_2$O and filtered. The filtrate is concentrated to give the title compound as a yellow oil. The residue in the filter is purified by silica column chromatography (CH$_2$Cl$_2$/MeOH+1% NH$_3^{aq}$, 97:3) to afford an additional quantity of the title compound for a combined yield: ES-MS: 306.1 [M+H]$^+$; $R_f$=0.30 (CH$_2$Cl$_2$/MeOH+1% NH$_3^{aq}$, 97:3).

EXAMPLE 6

N-{4-[(2-Dimethylamino-ethyl)-methyl-amino]-3-trifluoromethyl-phenyl}-2-(4-imidazo[4,5-c]pyridin-1-yl-phenyl)-acetamide The title compound is prepared as described in Example 1 but using 4-[(2-dimethylamino-ethyl)-methyl-amino]-3-trifluoromethyl-phenylamine. Title compound: ES-MS: 497.0 [M+H]$^+$; single peak at $t_R$=2.53 min (System 1); $R_f$=0.12 (CH$_2$Cl$_2$/MeOH+1% NH$_3^{aq}$, 9:1).

The starting material is prepared as follows:

Step 6.1: 4-[(2-Dimethylamino-ethyl)-methyl-amino]-3-trifluoromethyl-phenylamine The title compound is prepared as described in Step 5.1 but starting with 4-[(2-dimethylamino-ethyl)-methyl-amino]-3-trifluoromethyl-aniline. Title compound: ES-MS: 262.3 [M+H]$^+$; single peak at $t_R$=1.20 min (System 1).

Step 6.2: N,N,N'-Trimethyl-N'-(4-nitro-2-trifluoromethyl-phenyl)-ethane-1,2-diamine The title compound is prepared as described in Step 5.2 but using N,N,N'-trimethylethylene diamine (Fluka). Title compound: ES-MS: 292.1 [M+H]$^+$; $t_R$=3.19 min (System 1); $R_f$=0.19 (CH$_2$Cl$_2$/MeOH, 95:5).

EXAMPLE 7

N-(3'-Bromo-2-trifluoromethyl-biphen-4-yl)-2-(4-imidazo[4,5-b]pyridin-3-yl-phenyl)-acetamide The title compound is prepared as described in Example 1 but using 3'-bromo-2-trifluoromethyl-biphen-4-ylamine and (4-imidazo[4,5-b]pyridin-3-yl-phenyl)-acetic acid. Title compound: ES-MS: 552.8 [M+H]$^+$; $t_R$=5.24 min (System 1); $R_f$=0.20 (CH$_2$Cl$_2$/MeOH, 96:4).

The starting material is prepared as follows:

Step 7.1:
(4-Imidazo[4,5-b]pyridin-3-yl-phenyl)-acetic acid

Procedure A

The title compound is prepared as described in Step 1.1 but using (4-imidazo[4,5-b]pyridin-3-yl-phenyl)-acetic acid methyl ester. Title compound: ES-MS: 254.0 [M+H]$^+$; $t_R$=2.35 min (System 1).

Procedure B

A mixture of 4-iodophenylacetic acid (400 mg, 1.53 mmol), 4-azabenzimidazole (273 mg, 2.29 mmol, 1.5 equiv), trans,trans-dibenzylideneacetone (17.9 mg, 0.0763 mmol, 0.05 equiv) 1,10-phenanthroline (303 mg, 1.53 mmol), copper (I) trifluoromethanesulfonate benzene complex (19.2 mg, 0.0763 mmol, 0.05 equiv), and $Cs_2CO_3$ (547 mg, 1.68 mmol) in xylene (1.5 mL) is stirred for 80 h at 125° C. The reaction mixture is allowed to cool to rt and concentrated in vacuo. The residue is dissolved in a 1N NaOH aqueous solution and extracted with EtOAc. The aqueous layer is made acidic by addition of a 1N HCl aqueous solution and extracted with $CH_2Cl_2$. The organic phase is dried ($Na_2SO_4$), filtered and concentrated. The residue is purified by reversed phase MPLC($CH_3CN/H_2OTFA$) to provide the title compound.

Step 7.2:
(4-Imidazo[4,5-b]pyridin-3-yl-phenyl)-acetic acid methyl ester

The title compound is prepared as described in Step 1.2 but using (4-imidazo[4,5-b]pyridin-3-yl-phenyl)-acetic acid methyl ester. Title compound: ES-MS: 268.0 [M+H]$^+$; $t_R$=3.20 min (System 1).

Step 7.3:
[4-(3-Amino-pyridin-2-ylamino)-phenyl]-acetic acid methyl ester

A suspension of [4-(3-nitro-pyridin-2-ylamino)-phenyl]-acetic acid methyl ester (2 g, 9.50 mmol) and Raney Ni (~0.600 g) in MeOH (40 mL) is stirred for 4 h at rt, under a hydrogen atmosphere. The reaction mixture is filtered through a pad of Celite and concentrated to afford the title compound as a grey solid: ES-MS: 258.0 [M+H]$^+$; $t_R$=2.30 min (System 1); $R_f$=0.15 (Hexane/EtOAc, 1:1).

Step 7.4:
[4-(3-Nitro-pyridin-2-ylamino)-phenyl]-acetic acid methyl ester

A mixture of 2-chloro-3-nitro-pyridine (5.0 g, 31.4 mmol), (4-amino-phenyl)-acetic acid (4.75 g 31.4 mmol), and a 4 N solution of HCl in dioxane (7.85 mL, 31.4 mmol) in MeOH/dioxane (100 mL; 1:1, v/v) is stirred and refluxed for 30 h. (4-Amino-phenyl)-acetic acid (4.75 g 31.4 mmol) is added and the reaction mixture is stirred and refluxed for additional 18 h. The reaction mixture is allowed to cool to rt and concentrated in vacuo. The residue is dissolved in EtOAc, washed with a saturated aqueous solution of $NaHCO_3$, dried ($Na_2SO_4$), filtered and concentrated. Purification of the crude product by silica gel column chromatography (Hexane/EtOAc, 85:15→60:40) provides the title compound as a red solid: ES-MS: 288.0 [M+H]$^+$; $t_R$=4.71 min (System 1); $R_f$=0.20 (Hexane/EtOAc, 4:1).

Step 7.5:
3'-Bromo-2-trifluoromethyl-biphenyl-4-amine

The title compound is prepared as described in Ex. 3 (Step 3.1) for 1-(3'-chloro-2-trifluoromethyl-biphenyl-4-yl)-3-{4-[2-(4-dimethylamino-butylamino)-pyrimidin-4-yloxy]-2-methyl-phenyl}-urea but using 3-bromophenylboronic acid (Aldrich). The title compound: MS: 315.9 [M-1]$^-$; HPLC $^{Dt}R_{et}$=4.9; $R_f$=0.16 (Hexane/EtOAc, 4:1).

EXAMPLE 8

2-(4-Imidazo[4,5-b]pyridin-3-yl-phenyl)-N-[4-(4-methyl-piperazin-1-ylmethyl)-3-trifluoromethyl-phenyl]-acetamide The title compound is prepared as described in Example 1 but using (4-imidazo[4,5-b]pyridin-3-yl-phenyl)-acetic acid (Step 7.1) and 4-(4-methyl-piperazin-1-ylmethyl)-3-trifluoromethyl-phenylamine (see WO 03/099771). Title compound: ES-MS: 509.0 [M+H]$^+$; $t_R$=3.07 min (System 1); $R_f$=0.10 ($CH_2Cl_2$/MeOH, 9:1).

EXAMPLE 9

N-[4-(4-Ethyl-piperazin-1-ylmethyl)-3-trifluoromethyl-phenyl]-2-(4-imidazo[4,5-b]pyridin-3-yl-phenyl)acetamide The title compound is prepared as described in Example 1 but using (4-imidazo[4,5-b]pyridin-3-yl-phenyl)-acetic acid (Step 7.1) and 4-(4-ethyl-piperazin-1-ylmethyl)-3-trifluoromethyl-phenylamine (see WO 03/099771). Title compound: ES-MS: 523.0 [M+H]$^+$; single peak at $t_R$=3.00 min (System 1); $R_f$=0.12 ($CH_2Cl_2$/MeOH+1% $NH_3^{aq}$, 95:5).

EXAMPLE 10

2-(4-Imidazo[4,5-b]pyridin-3-yl-phenyl)-N-[4-(4-isopropyl-piperazin-1-ylmethyl)-3-trifluoromethyl-phenyl]-acetamide The title compound is prepared as described in Example 1 but using (4-imidazo[4,5-b]pyridin-3-yl-phenyl)-acetic acid (Step 7.1) and 4-(4-isopropyl-piperazin-1-ylmethyl)-3-trifluoromethyl-phenylamine (see WO 03/099771). Title compound: ES-MS: 537.0 [M+H]$^+$; single peak at $t_R$=3.08 min (System 1); $R_f$=0.12 ($CH_2Cl_2$/MeOH+1% $NH_3^{aq}$, 95:5).

EXAMPLE 11

N-{4-[(3-Dimethylamino-propyl)methyl-amino]-3-trifluoromethyl-phenyl}-2-(4-imidazo[4,5-b]pyridin-3-yl-phenyl)-acetamide The title compound is prepared as described in Example 1 but using (4-imidazo[4,5-b]pyridin-3-yl-phenyl)-acetic acid (Step 7.1) and 4-[(3-dimethylamino-propyl)-methyl-amino]-3-trifluoromethyl-phenylamine (Step 5.1). Title compound: ES-MS: 511.0 [M+H]$^+$; single peak at $t_R$=3.33 min (System 1).

EXAMPLE 12

2-(4-imidazo[4,5-b]pyridin-3-yl-phenyl)-N-(4-iodo-3-trifluoromethyl-phenyl)-acetamide The title compound is prepared as described in Example 1 but using (4-imidazo[4,5-b]pyridin-3-yl-phenyl)-acetic acid (Step 7.1) and 4-iodo-3-trifluoromethyl-phenylamine. Title compound: ES-MS: 522.7 [M+H]$^+$; single peak at $t_R$=4.72 min (System 1); $R_f$=0.25 ($CH_2Cl_2$/MeOH, 95:5).

The starting material is prepared as follows:

Step 12.1: 4-Iodo-3-trifluoromethyl-phenylamine

A suspension of 1-iodo-4-nitro-2-trifluoromethyl-benzene (see WO 00/09495) (0.500 g, 1.58 mmol) and Raney Ni (~0.100 g) in MeOH (10 mL) is stirred for 2 h at rt under a hydrogen atmosphere. The reaction mixture is filtered through a pad of Celite and concentrated to afford the title compound as a brown solid: ES-MS: 285.8 []$^-$; single peak at $t_R$=4.49 min (System 1); $R_f$=0.33 (Hexane/$CH_2Cl_2$, 2:3).

EXAMPLE 13

N-(4'-Cyano-2-trifluoromethyl-biphen-4-yl)-2-(4-imidazo[4,5-b]pyridin-3-yl-phenyl)-acetamide A mixture of 4-cyanophenylboronic acid (62 mg, 0.42 mmol, 2 equiv) in EtOH (0.2 mL) is added dropwise to a mixture of 2-(4-imidazo[4,5-b]pyridin-3-yl-phenyl)-N-(4-iodo-3-trifluoromethyl-phenyl)-acetamide (Example 12) (110 mg, 0.21 mmol), $PdCl_2(dppf)_2$ (5 mg, 0.01 mmol, 0.03 equiv), $Na_2CO_3$ (2 M solution in $H_2O$, 0.42 mL, 0.84 mmol, 4 equiv) in toluene (1 mL) at reflux. The reaction mixture is stirred at reflux for 1 h, allowed to cool to rt and diluted with EtOAc and $H_2O$. The aqueous layer is separated and extracted twice with EtOAc. The combined organic phase is washed with brine, dried ($Na_2SO_4$), filtered and concentrated in vacuo. Silica gel column chromatography purification ($CH_2Cl_2$/MeOH, 96:4) provides the title compound as a white solid: ES-MS: 495.9 [M−H]$^-$; single peak at $t_R$=4.68 min (System 1); $R_f$=0.15 ($CH_2Cl_2$/MeOH, 96:4).

EXAMPLE 14

2-(4-imidazo[4,5-b]pyridin-3-yl-phenyl)-N-(4'-methoxy-5-trifluoromethyl-biphen-3-yl)-acetamide The title compound is prepared as described in Example 1 but using (4-imidazo[4,5-b]pyridin-3-yl-phenyl)acetic acid (Step 7.1) and 4'-methoxy-5-trifluoromethyl-biphen-3-ylamine. Title compound: ES-MS: 502.9 [M+H]$^+$; $t_R$=5.00 min (System 1); $R_f$=0.21 (Hexane/EtOAc, 1:4).

The starting material is prepared as follows:

Step 14.1: 4'-Methoxy-5-trifluoromethyl-biphen-3-ylamine

The title compound is prepared as described in Example 13 but using 3-amino-5-bromobenzotrifluoride (RYAN SCIENTIFIC) and 4-methoxyphenylboronic acid (Aldrich). Title compound: ES-MS: 266.0 [M−H]$^-$; single peak at $t_R$=4.61 min (System 1); $R_f$=0.20 (Hexane/EtOAc, 3:1).

EXAMPLE 15

2-(4-Imidazo[4,5-b]pyridin-3-yl-phenyl)-N-{4-[methyl-(1-methyl-piperidin-4-yl)-amino]-3-trifluoromethyl-phenyl}-acetamide The title compound is prepared as described in Example 1 but using (4-imidazo[4,5-b]pyridin-3-yl-phenyl)-acetic acid (Step 7.1) and 4-[methyl-(1-methyl-piperidin-4-yl)-amino]-3-trifluoromethyl-phenylamine. Title compound: ES-MS: 523.0 [M+H]$^+$; single peak at $t_R$=3.33 min (System 1); $R_f$=0.18 ($CH_2Cl_2$/MeOH+1% $NH_3^{aq}$, 9:1).

The starting material is prepared as follows:

Step 15.1: 4-[Methyl-(1-methyl-piperidin-4-yl)-amino]-3-trifluoromethyl-phenylamine A suspension of methyl-(1-methyl-piperidin-4-yl)-(4-nitro-2-trifluoromethyl-phenyl)amine (0.812 g, 2.56 mmol) and Pd/C (10%) (0.200 g) in EtOH (20 mL) is stirred for 1 h 25 min at rt, under a hydrogen atmosphere. The reaction mixture is filtered through a pad of Celite and concentrated to afford the title compound as a yellow oil: ES-MS: 288.1 [M+H]$^+$; single peak at $t_R$=1.50 min (System 1).

Step 15.2: Methyl-(1-methyl-piperidin-4-yl)-(4-nitro-2-trifluoromethyl-phenyl)amine The title compound is prepared as described in Step 5.2 but using 1-methyl-4-(methylamino)-piperidine (Aldrich). Title compound: ES-MS: 318.0 [M+H]$^+$; single peak at $t_R$=3.44 min (System 1); $R_f$=0.42 ($CH_2Cl_2$/MeOH+1% $NH_3^{aq}$, 95:5).

EXAMPLE 16

2-(2-Chloro-4-imidazo[4,5-b]pyridin-3-yl-phenyl)-N-[4-(4-isopropyl-piperazin-1-ylmethyl)-3-trifluoromethyl-phenyl]-acetamide The title compound is prepared as described in Example 1 but using (2-chloro-4-imidazo[4,5-b]pyridin-3-yl-phenyl)-acetic acid and 4-(4-isopropyl-piperazin-1-ylmethyl)-3-trifluoromethyl-phenylamine (see WO 03/099771). Title compound: ES-MS: 570.9 [M+H]$^+$; single peak at $t_R$=3.46 min (System 1); $R_f$=0.26 ($CH_2Cl_2$/MeOH+1% $NH_3^{aq}$, 9:1).

The starting material is prepared as follows:

Step 16.1: (2-Chloro-4-imidazo[4,5-b]pyridin-3-yl-phenyl)-acetic acid

A mixture of (2-chloro-4-imidazo[4,5-b]pyridin-3-yl-phenyl)-acetic acid ethyl ester (0.325 g, 1.03 mmol), 0.5 N aqueous solution of LiOH (2 mL), and THF (2 mL) is stirred for 1 h at 40° C. The reaction mixture is allowed to cool to rt and then acidified by addition of 0.5 N HCl aqueous solution. The resulting precipitate is collected by vacuum filtration to provide the title compound as a white solid: ES-MS: 288.0 [M+H]$^+$; single peak at $t_R$=3.00 min (System 1).

Step 16.2: (2-Chloro-4-imidazo[4,5-b]pyridin-3-yl-phenyl)-acetic acid ethyl ester The title compound is prepared as described in Step 1.2 but using [4-(3-amino-pyridin-2-ylamino)-2-chloro-phenyl]-acetic acid ethyl ester. Title compound: ES-MS: 316.1 [M+H]$^+$; single peak at $t_R$=4.24 min (System 1); $R_f$=0.16 (Hexane/EtOAc, 1:1).

Step 16.3: [4-(3-Amino-pyridin-2-ylamino)-2-chloro-Phenyl]-acetic acid ethyl ester The title compound is prepared as described in Step 7.3 but using [2-chloro-4-(3-nitropyridin-2-ylamino)-phenyl]-acetic acid ethyl ester and EtOH as the solvent. The reaction mixture is stirred for 22 h at rt. Title compound: ES-MS: 306.1 [M+H]$^+$; single peak at $t_R$=3.06 min (System 1); $R_f$=0.16 (Hexane/EtOAc, 1:1).

Step 16.4: [2-Chloro-4-(3-nitro-pyridin-2-ylamino)-phenyl]-acetic acid ethyl ester A mixture of 2-chloro-3-nitro-pyridine (0.600 g, 3.80 mmol) (Aldrich) and (4-amino-2-chloro-phenyl)-acetic acid ethyl ester (see WO 97/21665) (0.800 g 3.80 mmol) in EtOH/dioxane (20 mL; 1:1, v/v) is stirred and refluxed for 72 h. The mixture is allowed to cool to rt and concentrated in vacuo. The crude material is purified by silica gel column chromatography (Hexane/EtOAc, 7:3) to afford a red solid, which upon trituration with $Et_2O$ provides the title compound as an orange solid: ES-MS: 336.0 [M+H]$^+$; single peak at $t_R$=5.59 min (System 1); $R_f$=0.39 (Hexane/EtOAc, 7:3).

EXAMPLE 17

2-(2-Chloro-4-imidazo[4,5-b]pyridin-3-yl-phenyl)-
N-[4-(4-methyl-piperazin-1-ylmethyl)-3-trifluorom-
ethyl-phenyl]-acetamide The title compound is prepared as described in Example 1 but using (2-chloro-4-imidazo[4,5-b]pyridin-3-yl-phenyl)-acetic acid (Step 16.1) and 4-(4-methyl-piperazin-1-ylmethyl)-3-trifluoromethyl-phenylamine (see WO 03/099771). Title compound: ES-MS: 542.9 [M+H]$^+$; single peak at $t_R$=3.31 min (System 1); $R_f$=0.16 (CH$_2$Cl$_2$/MeOH+1% NH$_3^{aq}$, 9:1).

EXAMPLE 18

2-(2-Chloro-4-imidazo[4,5-b]pyridin-3-yl-phenyl)-
N-[4-(4-ethyl-piperazin-1-ylmethyl)-3-trifluorom-
ethyl-phenyl]-acetamide The title compound is prepared as described in Example 1 but using (2-chloro-4-imidazo[4,5-b]pyridin-3-yl-phenyl)-acetic acid (Step 16.1) and 4-(4-ethyl-piperazin-1-ylmethyl)-3-trifluoromethyl-phenylamine (see WO 03/099771). Title compound: ES-MS: 556.9 [M+H]$^+$; single peak at $t_R$=3.36 min (System 1); $R_f$=0.13 (CH$_2$Cl$_2$/MeOH+1% NH$_{33}^{aq}$, 9:1).

EXAMPLE 19

2-(2-Chloro-4-imidazo[4,5-b]pyridin-3-yl-phenyl)-
N-{4-[(3-dimethylamino-propyl)-methyl-amino]-3-
trifluoromethyl-phenyl}-acetamide The title compound is prepared as described in Example 1 but using (2-chloro-4-imidazo[4,5-b]pyridin-3-yl-phenyl)-acetic acid (Step 16.1) and 4-[(3-dimethylamino-propyl)-methyl-amino]-3-trifluoromethyl-phenylamine (Step 5.1). Title compound: ES-MS: 544.9 [M+H]$^+$; single peak at $t_R$=3.66 min (System 1); $R_f$=0.28 (CH$_2$Cl$_2$/MeOH+1% NH$_3^{aq}$, 9:1).

EXAMPLE 20

2-(4-Benzoimidazol-1-yl-phenyl)-N-[4-(4-methyl-
piperazin-1-ylmethyl)-3-trifluoromethyl-phenyl]-
acetamide The title compound is prepared as described in Example 1 but using (4-benzoimidazol-1-yl-phenyl)-acetic acid and 4-(4-methyl-piperazin-1-ylmethyl)-3-trifluoromethyl-phenylamine (see WO 03/099771). Title compound: ES-MS: 508.0 [M+H]$^+$; single peak at $t_R$=2.84 min (System 1); $R_f$=0.10 (CH$_2$Cl$_2$/MeOH+1% NH$_3^{aq}$, 9:1).
The starting material is prepared as follows:

Step 20.1: (4-Benzoimidazol-1-yl-phenyl)-acetic acid

Procedure A
The title compound is prepared as described in Step 1.1 but using (4-benzoimidazol-1-yl-phenyl)-acetic acid methyl ester. The title compound: ES-MS: 253.1 [M+H]$^+$; single peak at $t_R$=2.36 min (System 1).
Procedure B
A mixture of (4-benzoimidazol-1-yl-phenyl)-acetic acid methyl ester (0.535 g, 2.01 mmol), an aqueous solution of LiOH (1 N, 2 mL, 2.00 mmol), and THF (2 mL) is stirred for 3 h at 45° C. The reaction mixture is allowed to cool to rt and acidified to pH 5 by addition of 0.5 N aqueous HCl. The resulting white precipitate is collected by vacuum filtration to provide the title compound: ES-MS: 253.1 [M+H]$^+$; single peak at $t_R$=2.36 min (System 1).
Procedure C
A mixture of 4-iodophenylacetic acid (4.4 g, 16.8 mmol), benzoimidazole (2.98 g, 25.2 mmol, 1.5 equiv), trans,trans-dibenzylideneacetone (197 mg, 0.840 mmol, 0.05 equiv) 1,10-phenanthroline (3.33 g, 16.8 mmol), copper (I) trifluoromethanesulfonate benzene complex (211 mg, 0.840 mmol, 0.05 equiv), and Cs$_2$CO$_3$ (6 g, 18.5 mmol) in xylene (12 mL) is stirred for 88 h at 125° C. The reaction mixture is allowed to cool to rt and concentrated in vacuo. The residue is dissolved in a 1N NaOH aqueous solution and extracted with EtOAc. The aqueous layer is made acidic by addition of a 1N HCl aqueous solution. The resulting precipitate (batch 1) is collected by vacuum filtration. The aqueous phase is extracted with CH$_2$Cl$_2$. The organic phase is dried (Na$_2$SO$_4$), filtered and concentrated. The residue (batch 2) is combined with batch 1 and triturated in Et$_2$O to afford 3.58 g of the title compound.

Step 20.2: (4-Benzoimidazol-1-yl-phenyl)-acetic acid methyl ester

The title compound is prepared as described in Step 1.2 but using [4-(2-amino-phenylamino)-phenyl]-acetic acid methyl ester. The title compound: ES-MS: 267.1 [M+H]$^+$; single peak at $t_R$=3.00 min (System 1).

Step 20.3: [4-(2-Amino-phenylamino)-phenyl]-acetic acid methyl ester

A suspension of [4-(2-nitro-phenylamino)-phenyl]-acetic acid methyl ester (0.700 g, 2.45 mmol) and Pd/C (10%) (0.240 g) in MeOH (20 mL) is stirred for 3 h at rt, under a hydrogen atmosphere. The reaction mixture is filtered through a pad of Celite and concentrated to afford the title compound as a black oil: ES-MS: 257.1 [M+H]$^+$; single peak at $t_R$=3.04 min (System 1).

Step 20.4: [4-(2-Nitro-phenylamino)-phenyl]-acetic acid methyl ester

A mixture of [4-(2-nitro-phenylamino)-phenyl]-acetic acid (1.0 g, 3.68 mmol) and HCl conc. (0.4 mL) in MeOH (20 mL) is stirred and refluxed for 1 h, allowed to cool to rt, and concentrated in vacuo. The residue is diluted with CH$_2$Cl$_2$, washed with an aqueous saturated solution of NaHCO$_3$, H$_2$O, and brine, then dried (Na$_2$SO$_4$), filtered and concentrated. Silica gel column chromatography purification (Hexane/EtOAc, 4:1) of the crude product affords the title compound as a red oil: ES-MS: 287.0 [M+H]$^+$; single peak at $t_R$=5.01 min (System 1); $R_f$=0.20 (Hexane/EtOAc, 4:1).

Step 20.5: [4-(2-Nitro-phenylamino)-phenyl]-acetic acid

A mixture of 2-nitrofluorobenzene (1.5 mL, 14.2 mmol, 1.5 equiv) (Aldrich), 4-aminophenyl acetic acid (1.44 g, 9.5 mmol), and KF (0.550 g, 9.5 mmol) is stirred at 170° C. for 16 h in a sealed tube. The reaction mixture is then allowed to cool to rt, triturated in CH$_2$Cl$_2$/MeOH (95:5) and filtered, and the filtrate is concentrated. The residue is purified by silica gel column chromatography (CH$_2$Cl$_2$/MeOH, 97:3→95:5) to

EXAMPLE 21

2-(4-Benzoimidazol-1-yl-phenyl)-N-{4-[methyl-(1-methyl-piperidin-4-yl)-amino]-3-trifluoromethyl-phenyl}-acetamide The title compound is prepared as described in Example 1 but using (4-benzoimidazol-1-yl-phenyl)-acetic acid (Step 20.1) and 4-[methyl-(1-methyl-piperidin-4-yl)-amino]-3-trifluoromethyl-phenylamine (Step 15.1). Title compound: ES-MS: 522.0 $[M+H]^+$; single peak at $t_R$=3.15 min (System 1); $R_f$=0.19 ($CH_2Cl_2$/MeOH+1% $NH_3^{aq}$, 9:1).

EXAMPLE 22

2-(4-Benzoimidazol-1-yl-phenyl)-N-{4-[(3-dimethylamino-propyl)-methyl-amino]-3-trifluoromethyl-phenyl}-acetamide The title compound is prepared as described in Example 1 but using (4-benzoimidazol-1-yl-phenyl)-acetic acid (Step 20.1) and 4-[(3-dimethylamino-propyl)-methyl-amino]-3-trifluoro-methyl-phenylamine (Step 5.1). Title compound: ES-MS: 510.0 $[M+H]^+$; single peak at $t_R$=3.12 min (System 1); $R_f$=0.14 ($CH_2Cl_2$/MeOH+1% $NH_3$ q, 9:1).

EXAMPLE 23

2-(4-Benzoimidazol-1-yl-phenyl)-N-{4-[(2-dimethylamino-ethyl)-methyl-amino]-3-trifluoromethyl-phenyl}-acetamide The title compound is prepared as described in Example 1 but using (4-benzoimidazol-1-yl-phenyl)-acetic acid (Step 20.1) and 4-[(2-dimethylamino-ethyl)-methyl-amino]-3-trifluoromethyl-phenylamine (Step 6.1). Title compound: ES-MS: 496.0 $[M+H]^+$; single peak at $t_R$=3.00 min (System 1); $R_f$=0.14 ($CH_2Cl_2$/MeOH+1% $NH_3^{aq}$, 9:1).

EXAMPLE 24

2-(4-Benzoimidazol-1-yl-phenyl)-N-(4'-cyano-2-trifluoromethyl-biphen-4-yl)-acetamide The title compound is prepared as described in Example 1 but using (4-benzoimidazol-1-yl-phenyl)-acetic acid (Step 20.1) and 4'-amino-2'-trifluoromethyl-biphenyl-4-carbonitrile. Title compound: ES-MS: 496.9 $[M+H]^+$; single peak at $t_R$=4.37 min (System 1); $R_f$=0.12 ($CH_2Cl_2$/MeOH, 96:4).

The starting material is prepared as follows:

Step 24.1: 4'-Amino-2'-trifluoromethyl-biphenyl-4-carbonitrile

The title compound is prepared as described in Example 13 but using 5-amino-3-bromobenzotrifluoride (OAKWOOD PRODUCTS; Inc.) and 1.5 equiv of 4-cyanophenylboronic acid (MATRIX SCIENTIFIC). Silica gel column chromatography purification (Hexane/EtOAc, 4:1) provides the title compound as a white solid: ES-MS: 262.0 $[M-H]^-$; single peak at $t_R$=4.37 min (System 1); $R_f$=0.09 (Hexane/EtOAc, 4:1).

EXAMPLE 25

2-{4-[5-(4-Methoxy-phenyl)-benzoimidazol-1-yl]-phenyl}-N-[4-(4-methyl-piperazin-1-ylmethyl)-3-trifluoromethyl-phenyl]-acetamide The title compound is prepared as described in Example 1 but using {4-[5-(4-methoxy-phenyl)-benzoimidazol-1-yl]-phenyl}-acetic acid and 4-(4-methyl-piperazin-1-ylmethyl)-3-trifluoromethyl-phenylamine (WO 03/099771). Title compound: ES-MS: 613.9 $[M+H]^+$; single peak at $t_R$=3.56 min (System 1); $R_f$=0.10 ($CH_2Cl_2$/MeOH+1% $NH_3^{aq}$, 9:1).

The starting material is prepared as follows:

Step 25.1: {4-[5-(4-Methoxy-phenyl)-benzoimidazol-1-yl]-phenyl}-acetic acid

The title compound is prepared as described in Step 20.1 (Procedure B) but using {4-[5-(4-methoxy-phenyl)-benzoimidazol-1-yl]-phenyl}-acetic acid ethyl ester. The title compound: ES-MS: 359.3 $[M+H]^+$; single peak at $t_R$=3.60 min (System 1); $R_f$=0.26 ($CH_2Cl_2$/MeOH+1% $NH_3^{aq}$, 9:1).

Step 25.2: {4-[5-(4-Methoxy-phenyl)-benzoimidazol-1-yl]-phenyl}-acetic acid ethyl ester A mixture of [4-(5-bromo-benzoimidazol-1-yl)-phenyl]-acetic acid ethyl ester (0.300 g, 0.84 mmol), 4-methoxyphenylboronic acid (0.152 g, 1.00 mmol, 1.2 equiv), $PdCl_2$(dppf) (18 mg, 0.025 mmol, 0.03 equiv), $Na_2CO_3$ (2 M solution in $H_2O$, 1.7 mL, 3.34 mmol, 4 equiv) in toluene/EtOH (12 mL; 5:1, v/v) is stirred and refluxed for 2 h. After further addition of boronic acid (0.100 g, 0.66 mmol) in EtOH (1 mL), the reaction mixture is stirred and refluxed for 30 min, allowed to cool to rt, diluted with EtOAc and $H_2O$, and filtered through a pad of Celite. The layers are separated and the aqueous phase is extracted with EtOAc. The combined organic phase is washed with brine, dried ($Na_2SO_4$), filtered and concentrated in vacuo. Silica gel column chromatography purification (Hexane/EtOAc, 3:1) provides the title compound as a yellow solid: ES-MS: 387.1 $[M+H]^+$; single peak at $t_R$=4.27 min (System 1); $R_f$=0.24 (Hexane/EtOAc, 3:1).

Step 25.3: [4-(5-Bromo-benzoimidazol-1-yl)-phenyl]-acetic acid ethyl ester

The title compound is prepared as described in Step 1.2 but using [4-(2-amino-4-bromo-phenylamino)-phenyl]-acetic acid ethyl ester. The title compound: ES-MS: 361.0 $[M+2]^+$; single peak at $t_R$=4.16 min (System 1).

Step 25.4: [4-(2-Amino-4-bromo-phenylamino)-phenyl]-acetic acid ethyl ester

A suspension of [4-(4-bromo-2-nitro-phenylamino)-phenyl]-acetic acid ethyl ester (1.0 g, 2.64 mmol) and Raney Ni (~0.300 g) in EtOH (20 mL) is stirred for 2.5 h at rt, under a hydrogen atmosphere. The reaction mixture is filtered through a pad of Celite and concentrated. Silica gel column chromatography purification (Hexane/EtOAc, 7:3) of the crude product affords the title compound as a pale pink solid: ES-MS: 351.0 $[M+2]^+$; single peak at $t_R$=4.82 min (System 1); $R_f$=0.16 (Hexane/EtOAc, 7:3).

Step 25.5: [4-(4-Bromo-2-nitro-phenylamino)-phenyl]-acetic acid ethyl ester

A mixture of 1-bromo-4-fluoro-3-nitrobenzene (MATRIX SCIENTIFIC) (10.7 g, 48.7 mmol) and 4-aminophenylacetic acid ethyl ester (8.7 g, 48.7 mmol) in NMP (50 mL) is stirred for 48 h at 110° C. The reaction mixture is allowed to cool at rt, diluted with EtOAc and $H_2O$. The layers are separated and the aqueous phase is extracted with EtOAc. The combined organic phase is washed brine, dried ($Na_2SO_4$), filtered and concentrated. Silica gel column chromatography purification (Hexane/EtOAc, 4:1) of the crude product affords the title compound as an orange oil: ES-MS: 380.9 [M+2]$^+$; single peak at $t_R$=5.75 min (System 1); $R_f$=0.27 (Hexane/EtOAc, 4:1).

EXAMPLE 26

N-[4-(3-Dimethylamino-prop-1-ynyl)-3-trifluoromethyl-phenyl]-2-(4-imidazo[4,5-b]pyridin-3-yl-phenyl)-acetamide Propylphosphonic anhydride (50% in DMF, 0.69 mL, 1.19 mmol, 2 equiv) is added to a solution of (4-imidazo[4,5-b]pyridin-3-yl-phenyl)acetic acid (Step 7.1) (0.150 g, 0.59 mmol), 4-(3-dimethylamino-prop-1-ynyl)-3-trifluoromethyl-phenylamine (0.138 g, 0.57 mmol, 0.95 equiv), DMAP (10 mg), and $Et_3N$ (0.82 mL, 5.93 mmol, 10 equiv) in DMF (2.0 mL), at rt and under an argon atmosphere. The reaction mixture is stirred at rt for 18 h, diluted with EtOAc and washed with $H_2O$. The aqueous layer is extracted with EtOAc. The combined organic phase is washed with brine, dried ($Na_2SO_4$), filtered and concentrated. The residue is purified by reversed phase MPLC ($CH_3CN/H_2O/TFA$) to provide the title compound as a white solid: ES-MS: 477.9 [M+H]$^+$; single peak at $t_R$=3.20 min (System 1); $R_f$=0.06 ($CH_2Cl_2/NH_3$ (2 N in MeOH), 95:5).

The starting material is prepared as follows:

Step 26.1: 4-(3-Dimethylamino-prop-1-ynyl)-3-trifluoromethyl-phenylamine

A mixture of dimethyl-[3-(4-nitro-2-trifluoromethyl-phenyl)-prop-2-ynyl]-amine (2.0 g, 7.4 mmol), iron powder (1.65 g, 29.4 mmol, 4 equiv), AcOH (5 mL), $H_2O$ (10 mL), and EtOH (40 mL) is stirred for 30 min at 80° C. The reaction mixture is allowed to cool to rt, basified by addition of a 1 M aqueous solution of $NH_3$, and filtered through Celite. The filtrate is partially concentrated and extracted with EtOAc. The organic phase is washed with brine, dried ($Na_2SO_4$), filtered and concentrated. The residue is purified by silica gel column chromatography ($CH_2Cl_2/NH_3$ (2 N in MeOH), 95:5) to provide the title compound as a brown oil: ES-MS: 243.0 [M+H]$^+$; single peak at $t_R$=2.49 min (System 1); $R_f$=0.10 ($CH_2Cl_2/NH_3$ (2 N in MeOH), 95:5).

Step 26.2: Dimethyl-[3-(4-nitro-2-trifluoromethyl-phenyl)-prop-2-ynyl]-amine t-$Bu_3P$ (0.25 M in dioxane, 8.9 mL, 2.2 mmol, 0.2 equiv), 3-dimethylamino-1-propyne (FLUKA) (1.65 mL, 15.6 mmol, 1.4 equiv), and i-$Pr_2NH$ (2.0 mL, 14.4 mmol, 1.3 equiv) are added sequentially to a mixture of 5-nitro-2-bromobenzotrifluoride (ALDRICH) (3 g, 11.1 mmol), CuI (0.148 g, 0.78 mmol, 0.07 equiv), and Pd(PhCN)$_2$Cl$_2$ (0.427 g, 1.1 mmol, 0.1 equiv) in dioxane (10 mL). The reaction mixture is stirred for 48 h at rt. Then, Pd(PhCN)$_2$Cl$_2$ (0.100 g) is added. After stirring for additional 24 h, the reaction mixture is diluted with EtOAc and $H_2O$ and filtered through a pad of Celite. The filtrate is extracted with EtOAc. The organic phase is washed with brine, dried ($Na_2SO_4$), filtered and concentrated. Purification of the crude material by silica gel column chromatography ($CH_2Cl_2/NH_3$ (2 N in MeOH), 95:5) affords the title compound as a brown oil: ES-MS: 273.0 [M+H]$^+$; single peak at $t_R$=3.06 min (System 1); $R_f$=0.13 ($CH_2Cl_2/NH_3$ (2 N in MeOH), 95:5).

EXAMPLE 27

N-(5-tert-Butyl-2-p-tolyl-2H-pyrazol-3-yl)-2-(4-imidazo[4,5-b]pyridine-3-yl-phenyl)-acetamide The title compound is prepared as described in Example 1 but using (4-imidazo[4,5-b]pyridin-3-yl-phenyl)-acetic acid (Step 7.1) and 5-tert-butyl-2-p-tolyl-2H-pyrazol-3-ylamine (see J. Med. Chem. 45, 2994-3008 (2002)). Title compound: ES-MS: 465.5 [M+H]$^+$; 1H NMR (CDCl$_3$) 8.55 (d, J=3.9 Hz, 1H), 8.38 (s, 1H), 8.24 (d, J=8.2 Hz), 7.83 (d, J=8.2 Hz, 2H), 7.52-7.48 (m, 1H), 7.45 (d, J=8.2 Hz, 2H), 7.42-7.40 (m, 1H), 7.39 (s, 1H, NH), 7.16 (d, J=8.2 Hz, 2H), 7.13 (d, J=8.2 Hz, 2H), 6.66 (s, 1H), 3.81 (s, 2H), 2.13 (s, 3H), 1.36 (s, 9H).

EXAMPLE 28

N-(5-tert-Butyl-2-phenyl-2H-pyrazol-3-yl)-2-(4-imidazo[4,5-b]pyridine-3-yl-phenyl)-propionamide A solution of (R/S-2-(4-Imidazo[4,5-b]pyridine-3-yl-phenyl)-propionic acid (step 28.1) in 0.5 ml of DMF is added to a solution HATU (42 mg, 0.11 mmol, 1.1 eq) and $Et_3N$ (50 μL, 0.36 mmol, 3 equiv) in 1 mL of DMF and shaken at rt for 5 min. A solution of 5-tert-Butyl-2-phenyl-2H-pyrazol-3-ylamine (0.1 mmol) in DMF (1 mL) is then added. The mixture is shaken at rt for 24 h then heated at 60° C. for 3 h. An additional portion of HATU (42 mg, 0.11 mmol, 1.1 equiv) and $Et_3N$ (50 μL, 0.36 mmol, 3 equiv) in 1 mL of DMF and the mixture was shaken for 18 h at 35° C. The reaction mixture is then filtered through a SPE cartridge of basic alumina and purified by preparative HPLC. The title compound: ES-MS: 465.01 [M+H]$^+$; $t_R$=4.6 min (System 3)

Step 28.1

R/S-2-(4-Imidazo[4,5-b]pyridine-3-yl-phenyl)-propionic acid methyl ester is dissolved in MeOH (2 mL) and 1M LiOH (1 mL) is added. The mixture is stirred at 60° C. for 30 min. The solvent is evaporated and the residue is acidified to pH 4 and extracted twice with EtOAc. The organic layer is washed with brine and dried with MgSO$_4$, filtered and concentrated. The crude product is purified by reverse phase MPLC using ACN/water. (R/S-2-(4-Imidazo[4,5-b]pyridine-3-yl-phenyl)-propionic acid is obtained as a colourless solid. Title compound: ES-MS: 268.24: [M+H]$^+$; $t_R$=1.3 min (System 2).

Step 28.2: R/S-2-(4-Imidazo[4,5-b]pyridine-3-yl-phenyl)-propionic acid methyl ester and 2-(4-imidazo[4,5-b]pyridine-3-yl-phenyl)-2-methyl-propionic acid methyl ester A solution of (4-imidazo[4,5-b]pyridin-3-yl-phenyl)acetic acid (Step 7.1) (1 g, 3.95 mmol), powdered KOH (900 mg, 13.8 mmol) and iodomethane (743 μL, 11.8 mmol) in DMSO (30 mL) is stirred at rt for 16 hours. An additional portion of iodomethane (743 µL, 11.8 mmol) is added and stirred for 2 h. The reaction is concentrated in vacuo, taken up in ethyl acetate, washed with water then dried, filtered and concentrated. The crude products are purified by MPLC using EtOAc/Hexane (1/1) to give R/S-2-(4-imidazo[4,5-b]pyridine-3-yl-phenyl)-propionic acid methyl ester and 2-(4-imidazo[4,5-b]pyridine-3-yl-phenyl)-2-methyl-propionic acid methyl ester.

R/S-2-(4-Imidazo[4,5-b]pyridine-3-yl-phenyl)-propionic acid methyl ester: ES-MS: 282.32 [M-H]$^+$; $t_R$=1.3 min (System 2).

2-(4-Imidazo[4,5-b]pyridine-3-yl-phenyl)-2-methyl-propionic acid methyl ester: ES-MS: 296.28 [M+H]$^+$; $t_R$=1.5 min (System 2).

EXAMPLE 29

N-(5-tert-Butyl-2-phenyl-2H-pyrazol-3-yl)-2-(4-imidazo[4,5-b]pyridine-3-yl-phenyl)isobutyramide The title compound is prepared as described in Example 28 but using 2-(4-imidazo[4,5-b]pyridine-3-yl-phenyl)-2-methyl-propionic acid. Title compound: ES-MS: 479.05 [M+H]$^+$; $t_R$=4.9 min (System 3).

Step 29.1: 2-(4-Imidazo[4,5-b]pyridine-3-yl-phenyl)-2-methyl-propionic acid

The title compound is prepared as in Step 28.1 but using 2-(4-imidazo[4,5-b]pyridine-3-yl-phenyl)-2-methyl-propionic acid methyl ester. Title compound: ES-MS: 282.38 [M+H]$^+$; $t_R$=1.5 min (System 2).

EXAMPLE 30

(S/R)—N-(5-tert-Butyl-2-p-tolyl-2H-pyrazol-3-yl)-2-hydroxy-2-(4-imidazo[4,5-b]pyridin-3-yl-phenyl)-acetamide N-(5-tert-Butyl-2-p-tolyl-2H-pyrazol-3-yl)-2-(4-imidazo[4,5-b]pyridin-3-yl-phenyl)-2-oxo-acetamide (Example 31) (28 mg, 0.059 mmol) is dissolved in MeOH (5 mL) and a solution of NaBH$_4$ (9.2 mg, 0.23 mmol) in water (0.5 mL) is added. The reaction mixture is stirred at rt under N$_2$ for 1 h. The reaction is then cooled to 0° C. and 1N HCl (0.25 mL) added. The crude is taken up with EtOAc and washed with 1M LiOH and brine. The organic layer is dried with MgSO$_4$, filtered and concentrated to afford (S/R)—N-(5-tert-butyl-2-p-tolyl-2H-pyrazol-3-yl)-2-hydroxy-2-(4-imidazo[4,5-b]pyridin-3-yl-phenyl)-acetamide as a colourless solid. Title compound: ES-MS: 481.07 [M+H]$^+$; $t_R$=1.6 min (System 2).

EXAMPLE 31

N-(5-tert-Butyl-2-p-tolyl-2H-pyrazol-3-yl)-2-(4-imidazo[4,5-b]pyridin-3-yl-phenyl)-2-oxo-acetamide A solution of (4-imidazo[4,5-b]pyridine-3-yl-phenyl)-oxo-acetic acid, HATU (104 mg, 0.27 mmol, 1.1 equiv) and triethylamine (0.102 mL, 0.73 mmol) in DMF (4 mL) is stirred for 5 minutes under N$_2$. 5-tert-Butyl-2-p-tolyl-2H-pyrazol-3-ylamine is then added and after 2 h, a further 1.2 equiv of HATU is added and after a further 2 h an additional 1.2 equiv of HATU is added. After 4 h, DMF is removed and the residue taken up in EtOAc and washed with 1N HCl, 1N NaOH and finally with brine. The organic layer is dried with MgSO$_4$, filtered and concentrated. The residue is purified by MPLC on reverse phase with ACN/water to give N-(5-tert-butyl-2-p-tolyl-2H-pyrazol-3-yl)-2-(4-imidazo[4,5-b]pyridin-3-yl-phenyl)-2-oxo-acetamide as a yellow oil. Title compound: 479.05 [M+H]$^+$; $t_R$=1.9 min (System 2).

Step 31.1: (4-Imidazo[4,5-b]pyridine-3-yl-phenyl)-oxo-acetic acid

A mixture of (4-imidazo[4,5-b]pyridine-3-yl-phenyl)-oxo-acetic acid ethyl ester (123 mg, 0.417 mmol) and 1N LiOH (0.5 mL, 0.5 mmol) in THF (4 mL) is stirred at rt for 5 min. 1M HCl (500 µL) is then added and the resulting precipitate filtered off. (4-Imidazo[4,5-b]pyridine-3-yl-phenyl)-oxo-acetic acid is obtained as a grey solid. Title compound: ES-MS=268.05 [M+H]$^+$; $t_R$=0.8 min (System 2).

Step 31.2: (4-Imidazo[4,5-b]pyridine-3-yl-phenyl)-oxo-acetic acid ethyl ester

A solution of [4-(3-amino-pyridin-2-ylamino)-phenyl]oxo-acetic acid ethyl ester (195 mg, 0.547 mmol) in triethyl orthoformate (5 mL) is heated at 144° C. for 5 h. The reaction mixture is left in the fridge over night and then refluxed for additional 5 h. The solvent is removed and the product is purified by reverse phase MPLC with ACN/water to afford (4-imidazo[4,5-b]pyridine-3-yl-phenyl)-oxo-acetic acid ethyl ester. ES-MS: 296.10 [M+H]$^+$; $t_R$=1.4 min (System 2).

Step 31.3: [4-(3-Amino-pyridin-2-ylamino)-phenyl]-oxo-acetic acid ethyl ester

10% Pd/C (9 mg) is added to a solution of [4-(3-nitro-pyridin-2-ylamino)-phenyl]oxo-acetic acid ethyl ester (26 7 mg, 0.847 mmol) in ethanol (2 mL). The mixture is stirred at rt for 1.5 h under H$_2$. The reaction mixture is filtered through celite and the solvent removed under vacuum to afford [4-(3-amino-pyridin-2-ylamino)-phenyl]oxo-acetic acid ethyl ester as a yellow solid. Title compound: ES-MS: 286.10 [M+H]$^+$; $t_R$=0.9 min (System 2).

Step 31.4: [4-(3-Nitro-pyridin-2-ylamino)-phenyl]-oxo-acetic acid ethyl ester

A mixture of (4-amino-phenyl)-oxo-acetic acid ethyl ester (347 mg, 1.8 mmol), 2-chloro-3-nitropyridine (294 mg, 1.8 mmol) and 4M HCl in dioxane (0.45 mL, 1.8 mmol) in ethanol (4 mL) is refluxed for 14 h. An additional 0.45 mL of 4M HCl in dioxane is added and the mixture refluxed for 5 h. The reaction mixture is cooled down to room temperature and the resulting precipitate is filtered off. [4-(3-Nitro-pyridin-2-ylamino)-phenyl]oxo-acetic acid ethyl ester is obtained as an orange solid. Title compound: ES-MS: 315.99 [M+H]$^+$; $t_R$=1.7 min (System 2).

Step 31.5: (4-Amino-phenyl)-oxo-acetic acid ethyl ester

A mixture of (4-nitro-phenyl)-oxo-acetic acid ethyl ester (500 mg, 2.2 mmol) and 10% Pd/C (233 mg) in ethanol (2 mL) is stirred for 11 h under hydrogen. The reaction mixture is filtered through celite and concentrated. The yellow solid (4-amino-phenyl)-oxo-acetic acid ethyl ester is obtained. Title compound: $t_R$=1.1 min (System 2).

EXAMPLE 32

(R/S)-5-Imidazo[4,5-b]pyridine-3-yl-3-oxo-indan-1-carboxylic acid (5-tert-butyl-2-phenyl-2H-pyrazol-3-yl)-amide HATU (46.7 mg, 0.12 mmol) and triethylamine (29.5 µL, 0.21 mmol) are added to a solution of (R/S)-5-imidazo[4,5-b]pyridine-3-yl-3-oxo-indan-1-carboxylic acid (30 mg, 0.1 mmol) in DMF (2.5 mL). The reaction is stirred at rt for 2 min then 5-tert-butyl-2-phenyl-2H-pyrazol-3-ylamine (21.5 mg, 0.1 mmol) is added. After stirring at rt for 8 h, DMF is removed in vacuo. The residue is purified by reversed phase MPLC using ACN/Water as eluant and 5-imidazo[4,5-b]pyridine-3-yl-3-oxo-indan-1-carboxylic acid (5-tert-butyl-2-phenyl-2H-pyrazol-3-yl)-amide is obtained as a white solid. Title compound: ES-MS: 491.00 [M+H]$^+$, $t_R$=1.6 min (System 2).

Step 32.1: 5-Imidazo[4,5-b]pyridine-3-yl-3-oxo-indan-1-carboxylic acid

A solution of 5-imidazo[4,5-b]pyridine-3-yl-3-oxo-indan-1-carboxylic acid ethyl ester (297 mg, 0.924 mmol) and 1N LiOH (1 mL, 1 mmol) in THF (1.7 mL) is stirred at rt for 15 min. THF is removed in vacuo, the residue taken up in EtOAC and washed with 1N LiOH. The aqueous layer was acidified with 1M HCl and extracted with EtOAc. The organic layer was washed with brine, dried with MgSO$_4$, filtered and concentrated. (R/S)-5-Imidazo[4,5-b]pyridine-3-yl-3-oxo-indan-1-carboxylic acid is obtained as a brown solid. Title compound: $^1$H NMR (DMSO-d6): 9.0 (s, 1H), 8.5 (d, 1H), 8.4 (d, 1H), 8.3 (s, 1H), 8.2 (d, 1H) 7.9 (d, 1H), 7.4 (dd, 1H) 4.4 (m, 1H), 3.0 (m, 2H); $t_R$=0.9 min (System 2).

Step 32.2: (R/S)-5-Imidazo[4,5-b]pyridine-3-yl-3-oxo-indan-1-carboxylic acid ethyl ester A solution of (R/S)-5-(3-Amino-pyridin-2-ylamino)-3-oxo-indan-1-carboxylic acid ethyl ester (754 mg, 2.42 mmol) in triethyl orthoformate (25 mL) is heated at 145° C. for 30 min. The solvent is evaporated and the residue purified by flash chromatography eluting with Hexane/EtOAc. (R/S)-5-Imidazo[4,5-b]pyridine-3-yl-3-oxo-indan-1-carboxylic acid ethyl ester is obtained as a colourless solid. Title compound: $^1$H NMR: (DMSO-d6): 9.0 (s, 1H), 8.5 (d, 1H), 8.4 (d, 1H), 8.3 (s, 1H), 8.2 (d, 1H) 7.9 (d, 1H), 7.4 (dd, 1H) 4.5 (m, 1H), 4.2 (m, 2H), 3.0 (m, 2H), 1.2 (t, 3H); $t_R$=1.2 min (System 2).

Step 32.3: (R/S)-5-(3-Amino-pyridin-2-ylamino)-3-oxo-indan-1-carboxylic acid ethyl ester 10% Pd/C (298 mg) is added to a solution of (R/S)-5-(3-nitro-pyridin-2-ylamino)-3-oxo-indan-1-carboxylic acid ethyl ester (956 mg, 2.8 mmol) in ethanol (25 mL). The mixture is stirred at rt for 2 h under H$_2$ then filtered through celite. The solvent is removed under vacuum to afford (R/S-5-(3-amino-pyridin-2-ylamino)-3-oxo-indan-1-carboxylic acid ethyl ester as a yellow solid. Title compound: $t_R$=0.9 min (System 2).

Step 32.4: (R/S-5-(3-Nitro-pyridin-2-ylamino)-3-oxo-indan-1-carboxylic acid ethyl ester A mixture of 2-chloro-3-nitropyridine (1.48 g, 9.03 mmol), (R/S)-5-Amino-3-oxo-indan-1-carboxylic acid ethyl ester (1.98 g, 9.03 mmol) and 4M HCl in dioxane (2.3 mL, 9.0 mmol) in ethanol (15 mL) is refluxed for 9 h. The reaction mixture is left at rt overnight then a further equivalent of 4M HCl in dioxan is added. After 4 h refluxing, the solvent is evaporated and the crude mixture purified by MPLC eluting with EtOAc/Hexane to give (R/S)-5-(3-Nitro-pyridin-2-ylamino)-3-oxo-indan-1-carboxylic acid ethyl ester as a red solid. Title compound: ES-MS: 342.19 [M+H]$^+$, $t_R$=1.6 min (System 2)

Step 32.5: (R/S)-5-Amino-3-oxo-indan-1-carboxylic acid ethyl ester (R/S)-5-Nitro-3-oxo-indan-1-carboxylic acid ethyl ester (3 g, 12 mmol) (Gadient, Fulvio; Suess, Rudolf. Indane carboxylic acids, DE 2505447) is added portionwise over 5 minutes to a stirred suspension of tin (II) chloride (13.9 g, 60.2 mmol) in ethanol (50 mL) at rt under nitrogen. The reaction is then refluxed for 30 min, cooled to rt, poured into ice water and the pH adjusted to 9 with 1M sodium hydroxide. The mixture is extracted with diethyl ether and then washed with brine, dried and concentrated in vacuo to give (R/S)-5-amino-3-oxo-indan-1-carboxylic acid ethyl ester as a light yellow solid. Title compound: ES-MS: 219.96 [M+H]$^+$; $t_R$=0.8 min (System 2).

EXAMPLE 33

(R/S)-5-Imidazo[4,5-b]pyridine-3-yl-indan-1-carboxylic acid (5-tert-butyl-2-p-tolyl-2H-pyrazol-3-yl)-amide The title compound is prepared as described in Example 31 but using 5-imidazo[4,5-b]pyridine-3-yl-indan-1-carboxylic acid. Title compound: ES-MS: 491.38 [M+H]$^+$; $t_R$=1.7 min (System 2).

Step 33.1: 5-Imidazo[4,5-b]pyridine-3-yl-indan-1-carboxylic acid

1M LiOH (1.8 mL, 1.8 mmol) is added to a solution of (R/S)-5-imidazo[4,5-b]pyridine-3-yl-indan-1-carboxylic acid ethyl ester (550 mg, 1.8 mmol) in THF (2 mL). EtOH (2 mL) is added and after 10 min, 1N NaOH (2.5 mL) is added. The mixture is stirred at rt for 1.5 h and then acidified with 1M HCl. Water is added to the reaction mixture and the compound extracted with EtOAc. The organic layers are combined and washed with brine, dried with MgSO$_4$, filtered and concentrated to give (R/S)-5-imidazo[4,5-b]pyridine-3-yl-indan-1-carboxylic acid as a white solid. Title compound: ES-MS: 280.09 [M+H]$^+$; $t_R$=1.0 min (System 2).

Step 33.2: (R/S)-5-Imidazo[4,5-b]pyridine-3-yl-indan-1-carboxylic acid ethyl ester The title compound is prepared as described in Example 32.2 but using (R/S)-(3-amino-pyridin-2-ylamino)-indan-1-carboxylic acid ethyl ester. Title compound: ES-MS: 308.12 [M+H]$^+$; $t_R$=1.3 min (System 2).

Step 33.3: (R/S)-(3-Amino-pyridin-2-ylamino)-indan-1-carboxylic acid ethyl ester The title compound is prepared as described in Example 32.3 but using (R/S)-(3-nitro-pyridin-2-ylamino)-indan-1-carboxylic acid ethyl ester. ES-MS: 298.17 [M+H]$^+$; $t_R$=1.0 min (System 2).

Step 33.4: (R/S)-(3-Nitro-pyridin-2-ylamino)-indan-1-carboxylic acid ethyl ester The title compound is prepared as described in Example 32.4 but using (R/S)-5-amino-indan-1-carboxylic acid ethyl ester. Title compound: ES-MS: 328.14 [M+H]$^+$; $t_R$=1.9 min (System 2).

Step 33.5: (R/S)-5-Amino-indan-1-carboxylic acid ethyl ester (R/S)-5-Nitro-3-oxo-indan-1-carboxylic acid ethyl (10 g, 40.1 mmol) (Gadient, Fulvio; Suess, Rudolf. Indane carboxylic acids, DE 2505447) is dissolved in acetic acid (120 mL) and perchloric acid (6 mL). 10% Pd/C (500 mg) is added and the mixture is stirred under 4 bars of hydrogen for 8 h. After filtration through celite, the solution is concentrated and the residue is basified with ammonium hydroxide at 0° C. The aqueous phase is washed with diethyl ether (2×) and acidified to pH 4 with 6N HCl. Water is removed under reduced pressure. The residue is taken up in EtOH and the precipitate is filtered off then the filtrate is concentrated. The residue is taken up in 120 mL of EtOH and 5 mL of sulfuric acid is added. The mixture is heated at 80° C. for 4 h. The reaction mixture is taken up with EtOAc and washed 1M NaOH (2×) and brine (1×). The organic layer is dried with MgSO$_4$, filtered and concentrated. The residue is purified by silica gel column chromatography with DCM (100%) to DCM/MeOH (97.5:2.5). The title compound is obtained as a brown oil. Title compound: ES-MS 206.08 [M+H]$^+$; $t_R$=0.9 min (System 2).

EXAMPLE 34

N-(5-tert-Butyl-2-o-tolyl-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-o-tolyl-2H-pyrazol-3-ylamine. Title compound: ES-MS: 465.07 [M+H]$^+$; $t_R$=3.1 min (System 3).

Step 34.1: 5-tert-Butyl-2-o-tolyl-2H-pyrazol-3-ylamine

A solution of o-tolyl-hydrazine hydrochloride (0.3 mmol) in 0.5 mL of toluene with 4,4-dimethyl-3-oxopentanenitrile (375 mg, 3 mmol, 10 equiv) and Et$_3$N (84 μL, 0.6 mmol, 2 equiv) is stirred at 110° C. overnight. The solvent is evaporated and the residue taken up in EtOAC and washed with saturated NaHCO$_3$ and brine. The organic layer is then concentrated and the residue diluted in 1 mL of ethanol and 1 mL of 1M HCl. The mixture was left at rt for 15 min and then it was concentrated. 5-tert-Butyl-2-o-tolyl-2H-pyrazol-3-ylamine is used crude in the preparation of Example 34.

EXAMPLE 35

N-(5-tert-Butyl-2-(2-ethyl-phenyl)-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(2-ethyl-phenyl)-2H-pyrazol-3-ylamine. Title compound: ES-MS: 479.10 [M+H]$^+$; $t_R$=3.3 min (System 3).

Step 35.1: 5-tert-Butyl-2-(2-ethyl-phenyl)-2H-pyrazol-3-ylamine

The title compound is prepared as described in Step 34.1 but using 2-ethyl-phenylhydrazine hydrochloride.

EXAMPLE 36

N-(5-tert-Butyl-2-(2-fluoro-phenyl)-2H-pyrazol-3-yl)-2-(4-imidazo[4,5-b]pyridine-3-yl-phenylacetamide The title compound is prepared as described in Example 28 but using 2-(4-imidazo[4,5-b]pyridine-3-yl-phenyl)-acetic acid and 5-tert-butyl-2-(2-fluoro-phenyl)-2H-pyrazol-3-ylamine. Title compound: ES-MS: 469.04 [M+H]$^+$; $t_R$=3.0 min (System 3).

Step 36.1: 5-tert-Butyl-2-(2-fluoro-phenyl)-2H-pyrazol-3-ylamine

The title compound is prepared as described in Step 34.1 but using 2-fluoro-phenylhydrazine hydrochloride.

EXAMPLE 37

N-(5-tert-Butyl-2-(2-chloro-phenyl)-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(2-chloro-phenyl)-2H-pyrazol-3-ylamine. Title compound: ES-MS: 485.03 [M+H]$^+$; $t_R$=3.08 min (System 3).

Step 37.1: 5-tert-Butyl-2-(2-chloro-phenyl)-2H-pyrazol-3-ylamine

The title compound is prepared as described in Step 34.1 but using 2-chloro-phenylhydrazine hydrochloride.

EXAMPLE 38

N-(5-tert-Butyl-2-(2-trifluoromethyl-phenyl)-2H-pyrazol-3-yl)-2-(4-imidazo[4,5-b]pyridine-3-yl-phenyl)acetamide The title compound is prepared as described in Example 28 but using 2-(4-imidazo[4,5-b]pyridine-3-yl-phenyl)-acetic acid and 5-tert-butyl-2-(2-trifluoromethyl-phenyl)-2H-pyrazol-3-ylamine. Title compound: ES-MS: 519.05 [M+H]$^+$; $t_R$=3.08 min (System 3).

Step 38.1: 5-tert-Butyl-2-(2-trifluoromethyl-phenyl)-2H-pyrazol-3-ylamine

The title compound is prepared as described in Step 34.1 but using 2-trifluoromethyl-phenylhydrazine hydrochloride.

EXAMPLE 39

N-(5-tert-Butyl-2-(2-methoxy-phenyl)-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(2-methoxy-phenyl)-2H-pyrazol-3-ylamine. Title compound: ES-MS: 481.07 [M+H]$^+$; $t_R$=3.02 min (System 3).

Step 39.1: 5-tert-Butyl-2-(2-methoxy-phenyl)-2H-pyrazol-3-ylamine

The title compound is prepared as described in Step 34.1 but using 2-methoxy-phenylhydrazine hydrochloride.

EXAMPLE 40

N-(5-tert-Butyl-2-(2,4-dimethyl-phenyl)-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(2,4-dimethyl-phenyl)-2H-pyrazol-3-ylamine. Title compound: ES-MS: 479.11 [M+H]$^+$; $t_R$=3.24 min (System 3).

Step 40.1: 5-tert-Butyl-2-(2,4-dimethyl-phenyl)-2H-pyrazol-3-ylamine

The title compound is prepared as described in Step 34.1 but using 2,4-dimethyl-phenylhydrazine hydrochloride.

EXAMPLE 41

N-(5-tert-Butyl-2-(2,5-difluoro-phenyl)-2H-pyrazol-3-yl)-2-(4-Imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(2,5-difluoro-phenyl)-2H-pyrazol-3-ylamine. Title compound: ES-MS: 487.01 [M+H]$^+$; $t_R$=3.10 min (System 3).

Step 41.1: 5-tert-Butyl-2-(2,5-difluoro-phenyl)-2H-pyrazol-3-ylamine

The title compound is prepared as described in Step 34.1 but using 2,5-difluoro-phenylhydrazine hydrochloride.

EXAMPLE 42

N-(5-methyl-2-phenyl-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-methyl-2-phenyl-2H-pyrazol-3-ylamine. Title compound: ES-MS: 409.50 [M+H]$^+$; $t_R$=1.21 min (System 3).

EXAMPLE 43

N-(5-cyclopropyl-2-phenyl-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-cyclopropyl-2-phenyl-2H-pyrazol-3-ylamine. Title compound: ES-MS: 435.50 [M+H]$^+$; $t_R$=1.34 min (System 3).

EXAMPLE 44

N-(5-tert-butyl-2-phenyl-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-phenyl-2H-pyrazol-3-ylamine. Title compound: ES-MS: 451.55 [M+H]$^+$; $t_R$=1.55 min (System 3).

EXAMPLE 45

N-(5-tert-Butyl-2-(4-morpholin-4-ylmethyl-phenyl)-2H-pyrazol-3-yl)-2-(4-Imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(4-morpholin-4-ylmethyl-phenyl)-2H-pyrazol-3-ylamine. Title compound: ES-MS: 550.09 [M-H]$^+$; $RT_T$=2.69 min (HPLC System 3).

Step 45.1: 4-(5-Amino-3-tert-butyl-pyrazol-1-yl)-benzoic acid

To a suspension of 2.4 g (16 mmol) 4-hydrazino-benzoic acid in 12 mL toluene, 2.0 g of pivaloyl acetonitrile are added at rt. The suspension is heated to and kept under reflux for 12 h. After completion, the resulting reaction mixture is allowed to cool to rt. The precipitated product is isolated by filtration, washed with cold toluene and dried under high vacuum. [M+1]$^+$=260.

Step 45.2: 5-[4-(5-Amino-3-tert-butyl-pyrazol-1-yl)-phenyl]-morpholin-4-yl-methanone To a solution of 515 mg (1.98 mmol) 4-(5-amino-3-tert-butyl-pyrazol-1-yl)-benzoic acid and 259 μL (2.98 mMol) morpholine in 8 mL THF, 495 mg (2.58 mmol) of EDC are added at rt. The reaction is stirred at rt for 2 h. After completion, the resulting reaction mixture is concentrated and the residue is taken up in CH$_2$Cl$_2$, washed with brine (2×), dried and concentrated. The residual crude product is purified by flash chromatography (SiO$_2$, CH$_2$Cl$_2$/MeOH; gradient 0-5% MeOH) to give the title compound as an off white powder. MS: [M+1]$^+$=329.

Step 45.3: 5-tert-Butyl-2-(4-morpholin-4-ylmethyl-phenyl)-2H-pyrazol-3-ylamine

To a solution of 490 mg 5-[4-(5-amino-3-tert-butyl-pyrazol-1-yl)-phenyl]-morpholin-4-yl-methanone (1.49 mmol) in 13 mL THF, 3 mL (2.98 mmol) of borane (1M solution in THF) are added at rt. The reaction is stirred at rt for 12 h, concentrated, taken up in MeOH and concentrated again (3×). The residual crude product is purified by flash chromatography (SiO$_2$, CH$_2$Cl$_2$/MeOH, gradient 0-5% MeOH) to give the title compound as a yellow solid. $^1$H-NMR (CDCl$_3$): 7.50 (d, J=7.2 Hz, 2H), 7.40 (d, J=7.2 Hz, 2H), 5.52 (s, 1H), 3.73-3.70 (m, 5H), 3.51 (s, 2H), 2.47-2.44 (m, 3H), 1.32 (s, 9H).

EXAMPLE 46

N-(5-tert-Butyl-2-(4-dimethylaminomethyl-phenyl)-2H-pyrazol-3-yl)-2-(4-Imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-(4-dimethylaminomethyl-phenyl)2H-pyrazol-3-ylamine. Title compound: ES-MS: 506.49 [M-H]+; RT$_T$=1.30 min (HPLC System 3).

Step 46.1: 5-tert-Butyl-2-(4-dimethylaminomethyl-phenyl)-2H-pyrazol-3-ylamine

The title compound is prepared according to example 45 (steps 1-3) by replacement of morpholine with dimethyl amine (33% wt solution in EtOH) in step 2.
ES-MS: 273.2 [M+H]+. $^1$H-NMR (CDCl$_3$): 7.50 (d, 2H), 7.38 (d, 2H), 5.51 (s, 1H), 3.72 (bs, 2H, NH), 3.44 (s, 2H), 2.25 (s, 6H), 1.32 (s, 9H).

EXAMPLE 47

N-[5-tert-Butyl-2-(3-morpholin-4-ylmethyl-phenyl)-2H-pyrazol-3-yl]-2-(4-imidazo[4,5-b]pyridin-3-yl-phenyl)acetamide The title compound is prepared as described in Example 28 but using 2-(4-imidazo[4,5-b]pyridine-3-yl-phenyl)-acetic acid and 5-tert-butyl-2-(3-morpholin-4-ylmethyl-phenyl)-2H-pyrazol-3-ylamine. Title compound: ES-MS: 550.41 [M-H]+; RT=1.40 min (HPLC System 3).

Step 47.1: 5-tert-Butyl-2-(3-morpholin-4-ylmethyl-phenyl)-2H-pyrazol-3-ylamine

The title compound is prepared according to example 45 (steps 1-3) by replacement of 4-hydrazino-benzoic acid with 3-hydrazino-benzoic acid in step 1. ES-MS: 215.2 [M+H]+; $^1$H-NMR (CDCl$_3$): 7.39 (s, 1H), 7.21-7.17 (m, 2H), 7.21 (d, 1H), 5.57 (s, 1H), 3.78-3.74 (m, 6H), 3.54 (s, 2H), 2.31-2.25 (m, 4H), 1.32 (s, 9H).

EXAMPLE 48

N-(5-tert-Butyl-2-[4-(4-methyl-piperazin-1-ylmethyl)-phenyl)-2H-pyrazol-3-yl)-2-(4-imidazo[4,5-b]pyridine-3-yl-phenyl)-acetamide The title compound is prepared as described in Example 28 but using 2-(4-imidazo[4,5-b]pyridine-3-yl-phenyl)-acetic acid and 5-tert-butyl-2-[4-(4-methyl-piperazin-1-ylmethyl)-phenyl)-2H-pyrazol-3-ylamine. Title compound: ES-MS: 563.10 [M+H]+; t$_R$=2.66 min (System 3).

Step 48.1: 5-tert-Butyl-2-[4-(4-methyl-piperazin-1-ylmethyl)-phenyl)-2H-pyrazol-3-ylamine The title compound is prepared according to Example 45 (steps 1-3) by replacement of morpholine with n-methyl piperazine in step 2.
ES-MS: 238.2 [M+H]+; $^1$H-NMR (DMSO-d6): 7.59 (d, 2H), 7.38 (d, 2H), 5.40 (s, 1H), 5.18 (bs, 2H, NH), 3.42 (s, 2H), 2.42-2.22 (m, 8H), 2.15 (s, 3H), 1.32 (s, 9H).

EXAMPLE 49

N-(5-tert-Butyl-2-[3-(4-methyl-piperazin-1-ylmethyl)-phenyl)-2H-pyrazol-3-yl)-2-(4-imidazo[4,5-b]pyridine-3-yl-phenyl)-acetamide The title compound is prepared as described in Example 28 but using 2-(4-Imidazo[4,5-b]pyridine-3-yl-phenyl)-acetic acid and 5-tert-butyl-2-[3-(4-methyl-piperazin-1-ylmethyl)-phenyl)-2H-pyrazol-3-ylamine. Title compound: ES-MS: 563.12 [M+H]+; t$_R$=2.67 min (System 3).

Step 49.1: 5-tert-Butyl-2-[4-(4-methyl-piperazin-1-ylmethyl)-phenyl)-2H-pyrazol-3-ylamine The title compound is prepared according to Example 45 (steps 1-3) by replacement of 4-hydrazino-benzoic acid with 3-hydrazino-benzoic acid in step 1 and morpholine with N-methylpiperazine in step 2.
ES-MS: 238.2 [M+H]+; $^1$H-NMR (CDCl$_3$): 7.45 (s, 1H), 7.42 (dd, 1H), 7.00 (d, 1H), 6.78 (d, 1H), 5.25 (s, 1H), 3.58 (s, 2H), 2.62-2.58 (m, 4H), 2.57-2.39 (m, 4H), 2.24 (s, 3H), 1.32 (s, 9H).

EXAMPLE 50

N-[4-(4-Ethyl-piperazin-1-yl)-phenyl]-2-(4-imidazo[4,5-b]pyridin-3-yl-phenyl)-acetamide The title compound is prepared as described in Example 7 but using 4-(4-ethyl-piperazin-1-yl)-aniline. Title compound: ES-MS: 441.1 [M+H]+; t$_R$=2.57 min (System 1).

Step 50.1: 4-(4-Ethylpiperazin-1-yl)-aniline

A suspension of 1-ethyl-4-(4-nitro-phenyl)-piperazine (6.2 g, 26.35 mmol) and Raney Nickel (2 g) in MeOH (120 mL) is stirred for 7 h at rt, under a hydrogen atmosphere. The reaction mixture is filtered through a pad of celite and concentrated to afford the title compound as a violet solid: ESI-MS: 206.1 [MH]+; TLC: R$_f$=0.15 (CH$_2$Cl$_2$/MeOH+1% NH$_3$$^{aq}$, 9:1).

Step 50.2: 1-Ethyl-4-(4-nitro-phenyl)-piperazine

A mixture of 1-bromo-4-nitrobenzene (6 g, 29.7 mmol) and 1-ethylpiperazine (7.6 mL, 59.4 mmol, 2 equiv) is heated to 80° C. for 15 h. After cooling to rt, the reaction mixture is diluted with water and DCM/MeOH, 9:1. The aqueous layer is separated and extracted with CH$_2$Cl$_2$/MeOH, 9:1. The organic phase is washed with brine, dried (sodium sulfate), filtered and concentrated. Purification of the residue by silica gel column chromatography (CH$_2$Cl$_2$/MeOH+1% NH$_3$$^{aq}$, 9:1) affords the title compound as a yellow solid: ESI-MS: 236.0 [MH]+; t$_R$=2.35 min (System 1); TLC: R$_f$=0.50 (CH$_2$Cl$_2$/MeOH+1% NH$_3$$^{aq}$, 9:1).

EXAMPLE 51

2-(4-Imidazo[4,5-b]pyridin-3-yl-phenyl)-N-[4-(4-isopropyl-piperazin-1-ylmethyl)-phenyl]-acetamide The title compound is prepared as described in Example 7 but using 4-(4-isopropyl-piperazin-1-ylmethyl)-phenylamine. Title compound: ES-MS: 469.1 [M+H]+; t$_R$=2.27 min (System 1).

Step 51.1: 4-(4-Isopropyl-piperazin-1-ylmethyl)-phenylamine

A suspension of 1-isopropyl-4-(4-nitro-benzyl)-piperazine (5.7 g, 21.65 mmol) and Raney Nickel (2 g) in MeOH (100 mL) is stirred for 6 h at rt, under a hydrogen atmosphere. The reaction mixture is filtered through a pad of celite and concentrated to afford 6.3 g of the title compound as a white solid: ESI-MS: 234.1 [M+H]$^+$; $t_R$=0.95 min (System 1).

Step 51.2: 1-isopropyl-4-(4-nitro-benzyl)-piperazine

A mixture of 4-nitrobenylchloride (4.1 g, 23.90 mmol), N-isopropylpiperazine (3.6 g, 28.67 mmol, 1.2 eq.), potassium carbonate (6.5 g, 47.79, 2 equiv), and acetone (82 mL) is stirred for 16 h at reflux. The reaction mixture is allowed to cool to rt, filtered and concentrated. Purification of the residue by silica gel column chromatography (CH$_2$Cl$_2$/MeOH+1% NH$_3$$^{aq}$, 9:1) affords 6.2 g of the title compound as a yellow solid: to afford the title compound as a yellow solid: ESI-MS: 264.1 [M+H]$^+$; $t_R$=1.73 min (System 1); TLC: R$_f$=0.34 (CH$_2$Cl$_2$/MeOH+1% NH$_3$$^{aq}$, 9:1).

EXAMPLE 52

N-[3-(4-Ethyl-piperazin-1-ylmethyl)-phenyl]-2-(4-imidazo[4,5-b]pyridin-3-yl-phenyl)-acetamide The title compound is prepared as described in Example 7 but using 4-(4-ethyl-piperazin-1-ylmethyl)-phenylamine (described in WO 03/099771). Title compound: ES-MS: 469.1 [M+H]$^+$; $t_R$=2.31 min (System 1).

Step 52.1: 3-(4-Ethyl-piperazin-1-ylmethyl)-phenylamine

The title compound is prepared as described in Step 51.1 but using 1-ethyl-4-(3-nitro-benzyl)-piperazine. Title compound: ES-MS: 220.1 [M+H]$^+$; $t_R$=0.98 min (System 1).

Step 52.2: 1-Ethyl-4-(3-nitro-benzyl)-piperazine

The title compound is prepared as described in Step 51.2 but using N-ethyl-piperazine. Title compound: ES-MS: 250.1 [M+H]$^+$; $t_R$=1.49 min (System 1); TLC: R$_f$=0.34 (CH$_2$Cl$_2$/MeOH+1% NH$_3$$^{aq}$, 9:1).

EXAMPLE 53

N-(4-Fluoro-3-trifluoromethyl-phenyl)-2-(4-imidazo[4,5-b]pyridin-3-yl-phenyl)-acetamide The title compound is prepared as described in Example 7 but using 4-fluoro-3-(trifluoromethyl)aniline. Title compound: ES-MS: 415.0 [M+H]$^+$; $t_R$=4.26 min (System 1).

EXAMPLE 54

2-(4-imidazo[4,5-b]pyridin-3-yl-phenyl)-N-(3-trifluoromethyl-phenyl)-acetamide

The title compound is prepared as described in Example 7 but using 3-(trifluoromethyl)aniline. Title compound: ES-MS: 397.0 [M+H]$^+$; $t_R$=4.19 min (System 1).

EXAMPLE 55

N-(4-Dimethylaminomethyl-3-trifluoromethyl-phenyl)-2-(4-imidazo[4,5-b]pyridin-3-yl-phenyl)-acetamide The title compound is prepared as described in Example 7 but using 4-dimethylaminomethyl-3-trifluoromethyl-phenylamine (disclosed in WO2005/051366). The crude product is purified by silica gel column chromatography (CH$_2$Cl$_2$/MeOH+1% NH$_3$$^{aq}$, 95:5). Title compound: ES-MS: 454.0 [M+H]$^+$; $t_R$=2.91 min (System 1); TLC: R$_f$=0.20 (CH$_2$Cl$_2$/MeOH+1% NH$_3$$^{aq}$, 97:3).

EXAMPLE 56

2-(2,6-Dichloro-4-imidazo[4,5-b]pyridin-3-yl-phenyl)-N-[4-(4-isopropyl-piperazin-1-ylmethyl)-3-trifluoromethyl-phenyl]-acetamide The title compound is prepared as described in Example 7 but using (2,6-dichloro-4-imidazo[4,5-b]pyridin-3-yl-phenyl)acetic acid and 4-(4-isopropyl-piperazin-1-ylmethyl)-3-trifluoromethyl-phenylamine (WO 03/099771). Title compound: ES-MS: 604.9/606.9 [M+H]$^+$; $t_R$=3.89 min (System 1); R$_f$=0.23 (CH$_2$Cl$_2$/(2N NH$_3$ in MeOH), 95:5).

Step 56.1: (2,6-Dichloro-4-imidazo[4,5-b]pyridin-3-yl-phenyl)-acetic acid

The title compound is prepared as described in Step 20.1 (Procedure B) but using (2,6-dichloro-4-imidazo[4,5-b]pyridin-3-yl-phenyl)-acetic acid methyl ester. Title compound: ES-MS: 322.0/324.0 [M+H]$^+$; $t_R$=3.61 min (System 1).

Step 56.2: (2,6-Dichloro-4-imidazo[4,5-b]pyridin-3-yl-phenyl)-acetic acid methyl ester A mixture of [4-(3-amino-pyridin-2-ylamino)-2,6-dichloro-phenyl]-acetic acid methyl ester (4.5 g, 13.8 mmol) and triethyl orthoformate (60 mL, 361 mmol, 26 equiv) is stirred for 13.5 h at reflux. The resulting mixture is allowed to cool to rt and concentrated in vacuo to provide the title compound as a dark solid: ES-MS: 336.0/338.0 [M+H]$^+$; $t_R$=4.58 min (System 1); R$_f$=0.28 (Hexane/EtOAc, 1:1).

Step 56.3: [4-(3-Amino-pyridin-2-ylamino)-2,6-dichloro-phenyl]-acetic acid methyl ester A suspension of [2,6-dichloro-4-(3-nitro-pyridin-2-ylamino)-phenyl]-acetic acid methyl ester (5 g, 14.0 mmol) and Raney Ni (~1 g) in MeOH (100 mL) is stirred for 20 h at rt, under a hydrogen atmosphere. The reaction mixture is filtered through a pad of celite and concentrated to afford the title compound as a grey solid: ES-MS: 326.0/328.0 [M+H]$^+$; $t_R$=3.09 min (System 1); TLC: R$_f$=0.42 (CH$_2$Cl$_2$/MeOH, 95:5).

Step 56.4: [2,6-Dichloro-4-(3-nitro-pyridin-2-ylamino)-phenyl]-acetic acid methyl ester A mixture of 2-chloro-3-nitro-pyridine (5.0 g, 31.4 mmol), (4-amino-2,6-dichloro-phenyl)-acetic acid methyl ester (7.8 g 33.3 mmol), and a 4 N solution of HCl in dioxane (12 mL, 48.0 mmol, 2.9 equiv) in MeOH/dioxane (60 mL; 1:1, v/v) is stirred for 46.5 h at 100° C. The reaction mixture is allowed to cool to rt and concentrated in vacuo. The residue is dissolved in EtOAc, washed with a saturated aqueous solution of NaHCO$_3$, dried (Na$_2$SO$_4$), filtered and concentrated. Purification of the crude product by silica gel column chromatography (Hexane/EtOAc, 4:1), followed by trituration in diethyl ether, provides the title compound: ES-MS: 355.9/357.9 [M+H]$^+$; $t_R$=5.33 min (System 1); R$_f$=0.25 (Hexane/EtOAc, 4:1).

Step 56.5: (4-Amino-2,6-dichloro-phenyl)-acetic acid methyl ester

A suspension of (2,6-dichloro-4-nitro-phenyl)-acetic acid methyl ester (12.7 g, 47.13 mmol) and Raney Nickel (3 g) in MeOH (500 mL) is stirred for 3.5 h at rt, under a hydrogen atmosphere. The reaction mixture is filtered through a pad of celite and concentrated to afford the title compound as a yellow solid: ESI-MS: 232.0/234.0 $[M-H]^-$; $t_R$=3.11 min (System 2).

Step 56.6: (2,6-Dichloro-4-nitro-phenyl)-acetic acid methyl ester

Concentrated sulfuric acid (2 mL, 37.33 mmol, 0.73 equiv) is added dropwise to a solution of (2,6-dichloro-4-nitro-phenyl)-acetic acid (EP 87218) (14.2 g, 51.1 mmol) in MeOH (500 mL). The resulting brown solution is stirred for 6 h at reflux. The reaction mixture is allowed to cool to rt and concentrated in vacuo. The residue is dissolved in EtOAc (400 mL) and a bit of water, washed with a saturated aqueous solution of $NaHCO_3$, dried ($Na_2SO_4$), filtered and concentrated. Purification of the crude product by silica gel column chromatography (Hexane/EtOAc, 2:1→1:1) provides the title compound as a yellow solid: ES-MS: 262.1/264.1 $[M+H]^+$; $t_R$=3.78 min (System 2); $R_f$=0.40 (Hexane/EtOAc, 2:1).

EXAMPLE 57

2-(2,6-Dichloro-4-imidazo[4,5-b]pyridin-3-yl-phenyl)-N-[4-(4-methyl-piperazin-1-ylmethyl)-3-trifluoromethyl-phenyl]-acetamide The title compound is prepared as described in Example 7 but using (2,6-dichloro-4-imidazo[4,5-b]pyridin-3-yl-phenyl)-acetic acid (Step 56.1) and 4-(4-methyl-piperazin-1-ylmethyl)-3-trifluoromethyl-phenylamine (WO 03/099771). Title compound: ES-MS: 576.8/578.9 $[M+H]^+$; $t_R$=3.72 min (System 1); $R_f$=0.17 ($CH_2Cl_2$/(2N $NH_3$ in MeOH), 95:5).

EXAMPLE 58

2-(2,6-Dichloro-4-imidazo[4,5-b]pyridin-3-yl-phenyl)-N-(3-trifluoromethyl-phenyl)-acetamide The title compound is prepared as described in Example 7 but using (2,6-dichloro-4-imidazo[4,5-b]pyridin-3-yl-phenyl)acetic acid (Step 56.1) and 3-(trifluoromethyl)aniline. Title compound: ES-MS: 462.9/464.9 $[M-H]^-$; $t_R$=5.08 min (System 1); $R_f$=0.37 ($CH_2Cl_2$/(2N $NH_3$ in MeOH), 95:5).

EXAMPLE 59

2-(2,6-Dichloro-4-imidazo[4,5-b]pyridin-3-yl-phenyl)-N-(4-diethylaminomethyl-3-trifluoromethyl-phenyl)-acetamide The title compound is prepared as described in Example 7 but using (2,6-dichloro-4-imidazo[4,5-b]pyridin-3-yl-phenyl)-acetic acid (Step 56.1) and 4-diethylaminomethyl-3-trifluoromethyl-phenylamine (disclosed in WO2005/051366). Title compound: ES-MS: 549.9/551.9 $[M+H]^+$; $t_R$=3.93 min (System 1); $R_f$=0.28 ($CH_2Cl_2$/MeOH, 95:5+0.1% $NH_3^{aq}$).

EXAMPLE 60

N-(4-Diethylaminomethyl-3-trifluoromethyl-phenyl)-2-(4-imidazo[4,5-b]pyridin-3-yl-2-methyl-Phenyl)-acetamide The title compound is prepared as described in Example 7 but using (4-imidazo[4,5-b]pyridin-3-yl-2-methyl-phenyl)-acetic acid and 4-diethylaminomethyl-3-trifluoromethyl-phenylamine (disclosed in WO2005/051366). Title compound: ES-MS: 496.0 $[M+H]^+$; $t_R$=3.31 min (System 1); $R_f$=0.43 ($CH_2Cl_2$/MeOH, 95:5+0.1% $NH_3^{aq}$).

Step 60.1: (4-imidazo[4,5-b]pyridin-3-yl-2-methyl-phenyl)-acetic acid

The title compound is prepared as described in Step 20.1 (Procedure B) but using (4-imidazo[4,5-b]pyridin-3-yl-2-methyl-phenyl)-acetic acid methyl ester. Title compound: ES-MS: 268.1 $[M+H]^+$; $t_R$=2.59 min (System 1).

Step 60.2: (4-Imidazo[4,5-b]pyridin-3-yl-2-methyl-phenyl)-acetic acid methyl ester A mixture of [4-(3-amino-pyridin-2-ylamino)-2-methyl-phenyl]-acetic acid methyl ester (1.92 g, 7.08 mmol) and triethyl orthoformate (30 mL, 181 mmol, 26 equiv) is stirred for 3 h at 150° C. The resulting mixture is allowed to cool to rt and concentrated in vacuo to provide the title compound: ES-MS: 282.1 $[M+H]^+$; $t_R$=3.39 min (System 1).

Step 60.3: [4-(3-Amino-pyridin-2-ylamino)-2-methyl-Phenyl]-acetic acid methyl ester A suspension of [2-methyl-4-(3-nitro-pyridin-2-ylamino)-phenyl]-acetic acid methyl ester (2.2 g, 7.30 mmol) and Raney Ni (~220 mg) in MeOH (50 mL) is stirred for 6.5 h at rt, under a hydrogen atmosphere. The reaction mixture is filtered through a pad of celite and concentrated to afford the title compound: ES-MS: 272.1 $[M+H]^+$; $t_R$=2.53 min (System 1).

Step 60.4: [2-Methyl-4-(3-nitro-pyridin-2-ylamino)-phenyl]-acetic acid methyl ester A mixture of 2-chloro-3-nitro-pyridine (1.5 g, 9.46 mmol), (4-amino-2-methyl-phenyl)-acetic acid methyl ester (3.39 g 18.9 mmol, 2 equiv), and a 4 N solution of HCl in dioxane (6.9 mL, 28.0 mmol, 2.9 equiv) in MeOH/dioxane (30 mL; 1:1, v/v) is stirred for 54 h at 100° C. The reaction mixture is allowed to cool to rt and concentrated in vacuo. The residue is dissolved in EtOAc, washed with a saturated aqueous solution of $NaHCO_3$, dried ($Na_2SO_4$), filtered and concentrated. Purification of the crude product by silica gel column chromatography ($CH_2Cl_2$/MeOH, 1:0→98:2) provides the title compound: ES-MS: 302.1 $[M+H]^+$; $t_R$=4.79 min (System 1); $R_f$=0.43 ($CH_2Cl_2$).

EXAMPLE 61

2-(4-Imidazo[4,5-b]pyridin-3-yl-2-methyl-phenyl)-N-[4-(4-methyl-piperazin-1-ylmethyl)-3-trifluoromethyl-phenyl]-acetamide The title compound is prepared as described in Example 7 but using (4-imidazo[4,5-b]pyridin-3-yl-2-methyl-phenyl)- acetic acid (Step 60.1) and 4-(4-methyl-piperazin-1-ylmethyl)-3-trifluoromethyl-phenylamine (disclosed in WO 03/099771). Title compound: ES-MS: 523.0 [M+H]$^+$; $t_R$=3.11 min (System 1); $R_f$=0.18 (CH$_2$Cl$_2$/MeOH, 95:5+0.1% NH$_3$$^{aq}$).

EXAMPLE 62

2-(4-Imidazo[4,5-b]pyridin-3-yl-2-methyl-phenyl)-N-[4-(4-ethyl-piperazin-1-ylmethyl)-3-trifluoromethyl-phenyl]-acetamide The title compound is prepared as described in Example 7 but using (4-imidazo[4,5-b]pyridin-3-yl-2-methyl-phenyl)-acetic acid (Step 60.1) and 4-(4-ethyl-piperazin-1-ylmethyl)-3-trifluoromethyl-phenylamine (disclosed in WO 03/099771). Title compound: ES-MS: 537.0 [M+H]$^+$; $t_R$=3.18 min (System 1); $R_f$=0.16 (CH$_2$Cl$_2$/MeOH, 95:5+0.1% NH$_3$$^{aq}$).

EXAMPLE 63

2-(4-Imidazo[4,5-b]pyridin-3-yl-2-methyl-phenyl)-N-(4-pyrrolidin-1-ylmethyl-3-trifluoromethyl-phenyl)-acetamide The title compound is prepared as described in Example 7 but using (4-imidazo[4,5-b]pyridin-3-yl-2-methyl-phenyl)-acetic acid (Step 60.1) and 4-pyrrolidin-1-ylmethyl-3-trifluoromethyl-phenylamine (disclosed in WO2005/051366). Title compound: ES-MS: 494.2 [M+H]$^+$; $t_R$=3.23 min (System 1); $R_f$=0.15 (CH$_2$Cl$_2$/MeOH, 95:5+0.1% NH$_3$$^{aq}$).

EXAMPLE 64

2-(4-Imidazo[4,5-b]pyridin-3-yl-2-methyl-phenyl)-N-(3-trifluoromethyl-phenyl)-acetamide The title compound is prepared as described in Example 7 but using (4-imidazo[4,5-b]pyridin-3-yl-2-methyl-phenyl)-acetic acid (Step 60.1) and 3-(trifluoromethyl)aniline. Title compound: ES-MS: 411.1 [M+H]$^+$; $t_R$=4.19 min (System 1); $R_f$=0.28 (CH$_2$Cl$_2$/MeOH, 95:5+0.1% NH$_3$$^{aq}$).

EXAMPLE 65

N-(4-Dimethylaminomethyl-3-trifluoromethyl-phenyl)-2-(4-imidazo[4,5-b]pyridin 3-yl-2-methyl-phenyl)-acetamide The title compound is prepared as described in Example 7 but using (4-imidazo[4,5-b]pyridin-3-yl-2-methyl-phenyl)-acetic acid (Step 60.1) and 4-dimethylaminomethyl-3-trifluoromethyl-phenylamine (disclosed in WO2005/051366). Title compound: ES-MS: 468.2 [M+H]$^+$; $t_R$=2.97 min (System 1); $R_f$=0.37 (CH$_2$Cl$_2$/MeOH, 9:1+0.1% NH$_3$$^{aq}$).

EXAMPLE 66

2-(4-Imidazo[4,5-b]pyridin-3-yl-2-methyl-phenyl)-N-[4-(4-isopropyl-piperazin-1-ylmethyl)-3-trifluoromethyl-phenyl]-acetamide The title compound is prepared as described in Example 7 but using (4-imidazo[4,5-b]pyridin-3-yl-2-methyl-phenyl)-acetic acid (Step 60.1) and 4-(4-isopropyl-piperazin-1-ylmethyl)-3-trifluoromethyl-phenylamine (disclosed in WO 03/099771). Title compound: ES-MS: 551.3 [M+H]$^+$; $t_R$=3.23 min (System 1); $R_f$=0.28 (CH$_2$Cl$_2$/MeOH, 9:1+0.1% NH$_3$$^{aq}$).

EXAMPLE 67

2-(4-Benzoimidazol-1-yl-phenyl)-N-[4-(4-ethyl-piperazin-1-ylmethyl)-3-trifluoromethyl-phenyl]-acetamide The title compound is prepared as described in Example 20 but using 4-(4-ethyl-piperazin-1-ylmethyl)-3-trifluoromethyl-phenylamine (disclosed in WO 03/099771). Title compound: ES-MS: 522.0 [M+H]$^+$; $t_R$=3.18 min (System 1); $R_f$=0.31 (CH$_2$Cl$_2$/MeOH, 9:1+0.1% NH$_3$$^{aq}$).

EXAMPLE 68

2-(4-Benzoimidazol-1-yl-phenyl)-N-(3-trifluoromethyl-phenyl)-acetamide

The title compound is prepared as described in Example 20 but using and 3-(trifluoromethyl)aniline. Title compound: ES-MS: 396.1 [M+H]$^+$; $t_R$=3.98 min (System 1); $R_f$=0.51 (CH$_2$Cl$_2$/MeOH, 9:1+0.1% NH$_3$$^{aq}$).

EXAMPLE 69

N-[4-(4-Isopropyl-piperazin-1-ylmethyl)-3-trifluoromethyl-phenyl]-2-(4-purin-9-yl-phenyl)-acetamide The title compound is prepared as described in Example 1 but using (4-purin-9-yl-phenyl)-acetic acid and 4-(4-isopropyl-piperazin-1-ylmethyl)-3-trifluoromethyl-phenylamine (disclosed in WO 03/099771). Title compound: ES-MS: 538.1 [M+H]$^+$; $t_R$=2.93 min (System 1); $R_f$=0.12 (CH$_2$Cl$_2$/MeOH/NH$_3$$^{aq}$, 94:5:1).

Step 69.1: (4-Purin-9-yl-phenyl)-acetic acid

A mixture of [4-(6-chloro-purin-9-yl)phenyl]-acetic acid ethyl ester (182 mg, 0.60 mmol) and Pd/C (10%) in MeOH containing 5% ammonia (15 mL) is stirred for 22 h at rt and under hydrogen (2 bar). The reaction mixture is filtered through a pad of celite and concentrated. The residue is purified by silica gel column chromatography (CH$_2$Cl$_2$/MeOH, 95:5), followed by trituration in Et$_2$O to afford a mixture of (4-purin-9-yl-phenyl)-acetic acid methyl and ethyl ester. This mixture is treated with a 2 N aqueous solution of LiOH (0.5 mL), and THF (1 mL) for 3 h at 50° C. The reaction mixture is allowed to cool to rt and then acidified by addition of 0.5 N HCl aqueous solution. The resulting precipitate is collected by vacuum filtration to provide the title compound as a white solid: ES-MS: 255.1 [M+H]$^+$; $t_R$=1.93 min (System 1).

Step 69.2: [4-(6-Chloro-purin-9-yl)-phenyl]-acetic acid ethyl ester

A mixture of [4-(5-amino-6-chloro-pyrimidin-4-ylamino)-phenyl]-acetic acid ethyl ester (0.178 g, 0.58 mmol) and triethyl orthoformate (4 mL, 23.3 mmol, 40 equiv) is stirred for 1 h at reflux. The resulting mixture is allowed to cool to rt and concentrated in vacuo to provide the title compound as a red solid: ES-MS: 317.0 [M+H]$^+$; $t_R$=4.06 min (System 1).

Step 69.3: [4-(5-Amino-6-chloro-pyrimidin-4-ylamino)-phenyl]-acetic acid ethyl ester A mixture of [4-(6-chloro-5-nitro-pyrimidin-4-ylamino)-phenyl]-acetic acid ethyl ester (0.400 g, 1.19 mmol) and Raney Ni (~0.100 g) in THF (10 mL) is stirred for 20.5 h at rt, under a hydrogen atmosphere. The reaction mixture is filtered through a pad of celite and concentrated. Purification of the residue by silica gel column chromatography (Hexane/EtOAc, 70:30) provides the title compound as a yellow solid:

ES-MS: 307.1 [M+H]⁺; single peak at $t_R$=3.81 min (System 1); $R_f$=0.06 (Hexane/EtOAc, 70:30).

Step 69.4: [4-(6-Chloro-5-nitro-pyrimidin-4-ylamino)-phenyl]-acetic acid ethyl ester 4-Aminophenylacetic acid ethyl ester (0.93 g, 5.2 mmol) is added to a solution of 4,6-dichloro-5-nitropyrimidine (2 g, 10.4 mmol, 2 equiv). The resulting mixture is stirred for 2 h at rt and 4-aminophenylacetic acid ethyl ester (0.47 g, 2.6 mmol, 0.5 equiv) is added. The reaction mixture is stirred for 15 min and filtered. The filtrate is concentrated. The residue is dissolved in EtOAc and a saturated aqueous solution of sodium bicarbonate. The layers are separated. The aqueous phase is extracted with EtOAc. The combined organic phase is washed with brine, dried ($Na_2SO_4$), filtered and concentrated. Purification of the residue by silica gel column chromatography (Hexane/EtOAc, 4:1) provides the title compound as a yellow solid: ES-MS: 335.0/337.0 [M-H]⁻; single peak at $t_R$=4.73 min (System 1); $R_f$=0.22 (Hexane/EtOAc, 4:1).

EXAMPLE 70

By selecting suitable starting materials and applying the processes described in Examples 1 to 69, the following compounds of formula I(A) can be prepared (R3, R9 and R10 represent hydrogen in all cases).

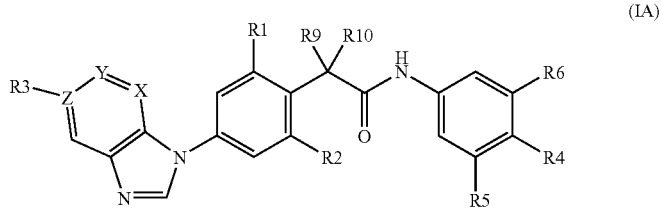

(IA)

| Ex | R1 | R2 | R4 | R5 | R6 | X | Y | Z |
|---|---|---|---|---|---|---|---|---|
| 70 a | H | H | H | 4-methyl-piperazin-1-yl | $CF_3$ | N | CH | C |
| 70 b | H | H | H | 4-ethyl-piperazin-1-yl | $CF_3$ | N | CH | C |
| 70 c | H | H | H | 4-iso-propyl-piperazin-1-yl | $CF_3$ | N | CH | C |
| 70 d | H | H | H | dimethylamino-methyl | $CF_3$ | N | CH | C |
| 70 e | H | H | H | 1-pyrrolidinyl-methyl | $CF_3$ | N | CH | C |
| 70 f | H | H | H | 2-methyl-imidazol-1-yl | $CF_3$ | N | CH | C |
| 70 g | H | H | H | 1-imidazolyl | $CF_3$ | N | CH | C |
| 70 h | H | H | H | 2,4-dimethyl-imidazol-1-yl | $CF_3$ | N | CH | C |
| 70 i | H | H | H | 4-methyl-piperazin-1-yl-methyl | $CF_3$ | N | CH | C |
| 70 j | H | H | H | N-methyl-N-(1-methyl-piperidin-4-yl)-amino | $CF_3$ | N | CH | C |
| 70 k | H | Cl | H | 4-methyl-piperazin-1-yl | $CF_3$ | N | CH | C |
| 70 l | H | Cl | H | 4-ethyl-piperazin-1-yl | $CF_3$ | N | CH | C |
| 70 m | H | Cl | H | 4-iso-propyl-piperazin-1-yl | $CF_3$ | N | CH | C |
| 70 n | H | Cl | H | dimethylamino-methyl | $CF_3$ | N | CH | C |
| 70 o | H | Cl | H | 1-pyrrolidinyl-methyl | $CF_3$ | N | CH | C |
| 70 p | H | Cl | H | 2-methyl-imidazol-1-yl | $CF_3$ | N | CH | C |
| 70 q | H | Cl | H | 1-imidazolyl | $CF_3$ | N | CH | C |
| 70 r | H | Cl | H | 2,4-dimethyl-imidazol-1-yl | $CF_3$ | N | CH | C |
| 70 s | H | Cl | H | 4-methyl-piperazin-1-yl-methyl | $CF_3$ | N | CH | C |
| 70 t | H | Cl | H | N-methyl-N-(1-methyl-piperidin-4-yl)-amino | $CF_3$ | N | CH | C |

EXAMPLE 71

By selecting suitable starting materials and applying the processes described in Examples 1 to 69, the following compounds of formula I(A) can be prepared (R3, R9 and R10 represent hydrogen in all cases).

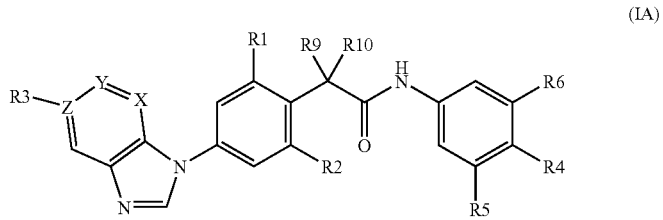

(IA)

| Ex | R1 | R2 | R4 | R5 | R6 | X | Y | Z |
|---|---|---|---|---|---|---|---|---|
| 71 a | H | Me | H | 4-methyl-piperazin-1-yl | $CF_3$ | N | CH | C |
| 71 b | H | Me | H | 4-ethyl-piperazin-1-yl | $CF_3$ | N | CH | C |

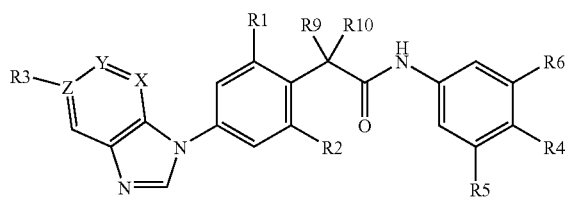

(IA)

| Ex | R1 | R2 | R4 | R5 | R6 | X | Y | Z |
|---|---|---|---|---|---|---|---|---|
| 71 c | H | Me | H | 4-iso-propyl-piperazin-1-yl | CF$_3$ | N | CH | C |
| 71 d | H | Me | H | dimethylamino-methyl | CF$_3$ | N | CH | C |
| 71 e | H | Me | H | 1-pyrrolidinyl-methyl | CF$_3$ | N | CH | C |
| 71 f | H | Me | H | 2-methyl-imidazol-1-yl | CF$_3$ | N | CH | C |
| 71 g | H | Me | H | 1-imidazolyl | CF$_3$ | N | CH | C |
| 71 h | H | Me | H | 2,4-dimethyl-imidazol-1-yl | CF$_3$ | N | CH | C |
| 71 i | H | Me | H | 4-methyl-piperazin-1-yl-methyl | CF$_3$ | N | CH | C |
| 71 j | H | Me | H | N-methyl-N-(1-methyl-piperidin-4-yl)-amino | CF$_3$ | N | CH | C |

EXAMPLE 72

By selecting suitable starting materials and applying the processes described in Examples 1 to 69, the following compounds of formula I(A) can be prepared (R3, R9 and R10 represent hydrogen in all cases).

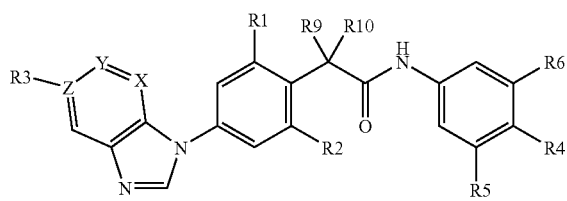

(IA)

| Ex | R1 | R2 | R4 | R5 | R6 | X | Y | Z |
|---|---|---|---|---|---|---|---|---|
| 72 a | H | H | H | 4-methyl-piperazin-1-yl | CF$_3$ | CH | CH | C |
| 72 b | H | H | H | 4-ethyl-piperazin-1-yl | CF$_3$ | CH | CH | C |
| 72 c | H | H | H | 4-iso-propyl-piperazin-1-yl | CF$_3$ | CH | CH | C |
| 72 d | H | H | H | dimethylamino-methyl | CF$_3$ | CH | CH | C |
| 72 e | H | H | H | 1-pyrrolidinyl-methyl | CF$_3$ | CH | CH | C |
| 72 f | H | H | H | 2-methyl-imidazol-1-yl | CF$_3$ | CH | CH | C |
| 72 g | H | H | H | 1-imidazolyl | CF$_3$ | CH | CH | C |
| 72 h | H | H | H | 2,4-dimethyl-imidazol-1-yl | CF$_3$ | CH | CH | C |
| 72 i | H | H | H | 4-methyl-piperazin-1-yl-methyl | CF$_3$ | CH | CH | C |
| 72 j | H | H | H | N-methyl-N-(1-methyl-piperidin-4-yl)-amino | CF$_3$ | CH | CH | C |
| 72 k | H | H | H | H | CF$_3$ | CH | CH | C |
| 72 l | H | H | dimethylamino-methyl | H | CF$_3$ | CH | CH | C |
| 72 m | H | H | 1-pyrrolidinyl-methyl | H | CF$_3$ | CH | CH | C |

EXAMPLE 73

By selecting suitable starting materials and applying the processes described in Examples 1 to 69, the following compounds of formula I(A) can be prepared (R3, R9 and R10 represent hydrogen in all cases).

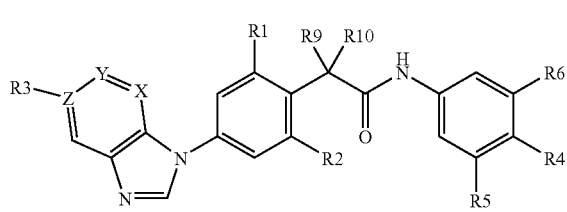

(IA)

| Ex | R1 | R2 | R4 | R5 | R6 | X | Y | Z |
|---|---|---|---|---|---|---|---|---|
| 73 a | H | Me | H | 4-methyl-piperazin-1-yl | CF$_3$ | CH | CH | C |
| 73 b | H | Me | H | 4-ethyl-piperazin-1-yl | CF$_3$ | CH | CH | C |
| 73 c | H | Me | H | 4-iso-propyl-piperazin-1-yl | CF$_3$ | CH | CH | C |
| 73 d | H | Me | H | dimethylamino-methyl | CF$_3$ | CH | CH | C |
| 73 e | H | Me | H | 1-pyrrolidinyl-methyl | CF$_3$ | CH | CH | C |
| 73 f | H | Me | H | 2-methyl-imidazol-1-yl | CF$_3$ | CH | CH | C |
| 73 g | H | Me | H | 1-imidazolyl | CF$_3$ | CH | CH | C |
| 73 h | H | Me | H | 2,4-dimethyl-imidazol-1-yl | CF$_3$ | CH | CH | C |
| 73 i | H | Me | H | 4-methyl-piperazin-1-yl-methyl | CF$_3$ | CH | CH | C |
| 73 j | H | Me | H | N-methyl-N-(1-methyl-piperidin-4-yl)-amino | CF$_3$ | CH | CH | C |
| 73 k | H | Me | H | H | CF$_3$ | CH | CH | C |
| 73 l | H | Me | dimethylamino-methyl | H | CF$_3$ | CH | CH | C |
| 73 m | H | Me | 1-pyrrolidinyl-methyl | H | CF$_3$ | CH | CH | C |
| 73 n | H | Me | 4-methyl-piperazin-1-yl-methyl | H | CF$_3$ | CH | CH | C |
| 73 o | H | Me | 4-ethyl-piperazin-1-yl-methyl | H | CF$_3$ | CH | CH | C |
| 73 p | H | Me | 4-iso-propyl-piperazin-1-yl-methyl | H | CF$_3$ | CH | CH | C |

EXAMPLE 74

Tablets Comprising a Compound of the Examples

Tablets, comprising, as active ingredient, 100 mg of any one of the compounds of Examples 1 to 70 are prepared with the following composition, following standard procedures:

Composition

| Active Ingredient | 100 mg |
|---|---|
| crystalline lactose | 240 mg |
| Avicel | 80 mg |
| PVPPXL | 20 mg |
| Aerosil | 2 mg |
| magnesium stearate | 5 mg |
| | 447 mg |

Manufacture: The active ingredient is mixed with the carrier materials and compressed by means of a tabletting machine (Korsch EKO).

Avicel is microcrystalline cellulose (FMC, Philadelphia, USA).

PVPPXL is polyvinylpolypyrrolidone, cross-linked (BASF, Germany).

Aerosil is silcium dioxide (Degussa, Germany).

EXAMPLE 75

Capsules

Capsules, comprising, as active ingredient, 100 mg of any one of the compounds of Examples 1 to 70, of the following composition are prepared according to standard procedures:

Composition

| Active Ingredient | 100 mg |
|---|---|
| Avicel | 200 mg |
| PVPPXL | 15 mg |
| Aerosil | 2 mg |
| magnesium stearate | 1.5 mg |
| | 318.5 mg |

Manufacturing is done by mixing the components and filling them into hard gelatine capsules, size 1.

What is claimed is:

1. A compound of the formula I,

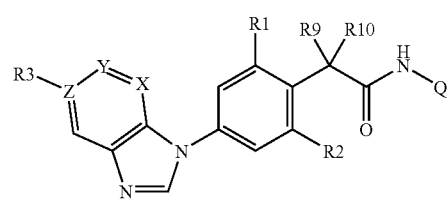

(I)

wherein each of R1 and R2, independently of the other, is selected from the group consisting of hydrogen, halo and C$_1$-C$_7$-alkyl;

R3 is absent if Z is nitrogen or, if Z is C, then R3 is hydrogen, unsubstituted or substituted aryl or unsubstituted or substituted heterocyclyl;

X is N (nitrogen) or CH (hydrogen-substituted carbon),

Y is CH or N,

Z is C or N, and
Q is a moiety of the formula (A)

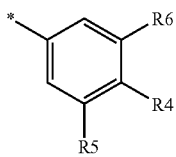

wherein
R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;
R5 is hydrogen, unsubstituted or substituted alkyl, unsubstituted or substituted amino, unsubstituted or substituted aryl or unsubstituted or substituted heterocyclyl; and
R6 is hydrogen, unsubstituted or substituted cycloalkyl or unsubstituted or substituted alkyl;
or a moiety of the formula (B)

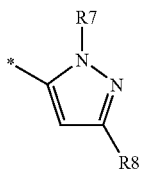

wherein
R7 is unsubstituted or substituted aryl or unsubstituted or substituted heterocyclyl and
R8 is alkyl or cycloalkyl;
where the asterisk * in formulae (A) and (B) marks the bond through which the moiety is bound to the NH of the amide group in formula I; and
(a) each of R9 and R10, independently of the other, is selected from the group consisting of hydrogen, hydroxyl and $C_1$-$C_7$-alkyl; or
(b) R9 and R10 together represent oxo; or
R1 and R9 together form a group —C(O)—CH2— or —CH2—CH2—, R2 is selected from the group consisting of hydrogen, halo and $C_1$-$C_7$-alkyl, and R10 represents hydrogen;
or a pharmaceutically acceptable salt thereof.

2. A compound of the formula I according to claim wherein each of R1 and R2, independently of the other, is selected from the group consisting of hydrogen, halo and C1-C7-alkyl;
R3 is absent if Z is nitrogen or, if Z is C, then R3 is hydrogen, unsubstituted or substituted aryl or unsubstituted or substituted heterocyclyl;
R9 and R10 both represent hydrogen; and
X is N or CH,
Y is CH or N,
Z is C or N,
and
Q is a moiety of the formula (A) wherein R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;
R5 is hydrogen, unsubstituted or substituted aryl or unsubstituted or substituted heterocyclyl; and
R6 is unsubstituted or substituted cycloalkyl or unsubstituted or substituted alkyl;
or a moiety of the formula (B) wherein
R7 is unsubstituted or substituted aryl or unsubstituted or substituted heterocyclyl and
R8 is alkyl or cycloalkyl;
where the asterisk * in formulae (A) and (B) marks the bond through which the moiety is bound to the NH of the amide group in formula I;
or a pharmaceutically acceptable salt thereof.

3. A compound of the formula I according to claim 2 wherein each of R1 and R2, independently of the other, is selected from the group consisting of hydrogen, halo and $C_1$-$C_7$-alkyl;
R3 is absent if Z is nitrogen or, if Z is C, then R3 is hydrogen or unsubstituted or substituted aryl;
R9 and R10 both represent hydrogen;
X is N or CH,
Y is CH;
Z is C or N
and
Q is a moiety of the formula (A)
wherein R4 is hydrogen, halo, unsubstituted or substituted amino, unsubstituted or substituted aryl, unsubstituted or substituted alkyl or unsubstituted or substituted alkynyl;
R5 is hydrogen or unsubstituted or substituted aryl; and
R6 is unsubstituted or substituted alkyl;
or a moiety of the formula (B)
wherein
R7 is unsubstituted or substituted aryl and
R8 is alkyl;
or a pharmaceutically acceptable salt thereof.

4. A compound of the formula I according to claim 2, wherein
R1 is hydrogen, chloro, or $C_1$-$C_7$alkyl,
R2 is hydrogen, chloro, or $C_1$-$C_7$alkyl,
R3 is absent if Z is nitrogen or, if Z is C, then R3 is hydrogen, phenyl that is unsubstituted or substituted by one or more moieties independently selected from $C_1$-$C_7$alkyl, halo, hydroxy, $C_1$-$C_7$-alkoxy and cyano,
R9 and R10 both represent hydrogen,
X is N or CH,
Y is CH,
Z is C or N,
Q is a moiety of the formula (A) wherein
R4 is hydrogen, iodo, phenyl that is unsubstituted or substituted by one or more moieties independently selected from $C_1$-$C_7$-alkyl, halo, hydroxy, $C_1$-$C_7$-alkoxy and cyano; N,N-di-($C_1$-$C_7$-alkyl)-amino-$C_1$-$C_7$alkyl, N-[(N-mono- or N,N-di-($C_1$-$C_7$-alkyl)-amino)-$C_1$-$C_7$-alkyl]-N—$C_1$-$C_7$-alkylamino, pyrrolidino, piperidino, piperazino, 4-$C_1$-$C_7$-alkylpiperazino 1-$C_1$-$C_7$-alkylpiperidin-4-yl, morpholino, thiomorpholino, pyrrolidino-$C_1$-$C_7$-alkyl, piperidino-$C_1$-$C_7$-alkyl, piperazino-$C_1$-$C_7$-alkyl, 4-$C_1$-$C_7$-alkylpiperazino-$C_1$-$C_7$-alkyl, morpholino-C1-C7-alkyl, thiomorpholino-C1-$C_7$-alkyl, N-piperidin-(2, 3 or 4)-yl-amino, N—$C_1$-$C_7$- alkyl-N-piperidin-ylamino wherein piperi-dinyl is bound via a ring carbon and is unsubstituted or substituted by lower alkyl, or N,N-di-(lower alkyl, phenyl and/or phenyl lower alkyl)-$C_3$-$C_7$-alkynyl;

R5 is hydrogen or phenyl that is unsubstituted or substituted by one or more moieties independently selected from $C_1$-$C_7$-alkyl, halo, hydroxy, $C_1$-$C_7$-alkoxy and cyano; and R6 is $C_1$-$C_7$-alkyl, $C_3$-$C_8$-cycloalkyl or halo-$C_1$-$C_7$-alkyl, trifluoromethyl, or a moiety of the formula (B) wherein R7 is phenyl that is unsubstituted or substituted by one or more moieties independently selected from $C_1$-$C_7$-alkyl, halo, hydroxy, $C_1$-$C_7$-alkoxy and cyano; and R8 is $C_3$-$C_8$cycloalkyl or $C_1$-$C_7$-alkyl;

or a pharmaceutically acceptable salt thereof.

5. A compound of the formula I according to claims 2, wherein

R1 is hydrogen,

R2 is hydrogen or chloro,

R3 is absent if Z is nitrogen or, if Z is C, then R3 is hydrogen, phenyl that is unsubstituted or substituted by $C_1$-$C_7$-alkoxy, R9 and R10 both represent hydrogen, X is N or CH, Y is CH, Z is C or N, Q is a moiety of the formula (A) wherein R4 is hydrogen, iodo, phenyl that is unsubstituted or substituted by-chloro, bromo, cyano;

N—[(N-mono- or N,N-di-($C_1$-$C_7$-alkyl)-amino)—$C_1$-$C_7$-alkyl]-N—$C_1$-$C_7$-alkylamino, N-2-[N—(N,N-dimethylamino)-ethyl-N-methyl-amino or N—(N,N-dimethylamino)-methyl-N-methyl-amino, pyrrolidino -$C_1$-$C_7$-alkyl, piperazino-$C_1$-$C_7$-alkyl, 4-$C_1$-$C_7$-alkylpiperazino-$C_1$-$C_7$-alkyl, N—$C_1$-$C_7$-alkyl-N-piperidin-ylamino wherein piperidinyl is bound via a ring carbon and is unsubstituted or substituted by lower alkyl, or N,N-di-(lower alkyl, phenyl and/ or phenyl lower alkyl)-$C_3$-$C_7$-alkynyl;

R5 is hydrogen or phenyl that is unsubstituted or substituted by $C_1$-$C_7$-alkoxy, and R6 is halo-$C_1$-$C_7$-alkyl, or a moiety of the formula (B) wherein R7 is phenyl that is unsubstituted or substituted by $C_1$-$C_7$-alkyl; and R8 is $C_1$-$C_7$-alkyl;

or a pharmaceutically acceptable salt thereof.

6. A compound of the formula I according to claim 1 wherein each of R1 and R2, independently of the other, is selected from the group consisting of hydrogen, halo and C1-C7-alkyl;

R3 is absent if Z is nitrogen or, if Z is C, then R3 is hydrogen or unsubstituted or substituted aryl;

X is N or CH,

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted cycloalkyl, unsubstituted or substituted alkyl, unsubstituted or substituted alkenyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen, unsubstituted or substituted cycloalkyl or unsubstituted or substituted alkyl;

or a moiety of the formula (B) wherein

R7 is unsubstituted or substituted aryl or unsubstituted or substituted heterocyclyl and R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2—or —CH2—CH2—, R2 is selected from the group consisting of hydrogen, halo and $C_1$-$C_7$-alkyl, and R10 represents hydrogen;

or a pharmaceutically acceptable salt thereof.

7. A compound of the formula I according to claim 1 wherein each of R1 and R2, independently of the other, is selected from the group consisting of hydrogen, halo and $C_1$-$C_7$-alkyl;

R3 is absent if Z is nitrogen or, if Z is C, the R3 is hydrogen or unsubstituted or substituted aryl;

X is N or CH,

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted alkyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen or substituted alkyl;

or a moiety of the formula (B) wherein

R7 is unsubstituted or substituted aryl and

R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$-alkyl; or (b) R9 and R10 together represent oxo; or R1 and R9 together form a group —C(O)—CH2—or —CH2—CH2—, R2 is selected from the group consisting of hydrogen, halo and $C_1$-$C_7$-alkyl, and R10 represents hydrogen;

or a pharmaceutically acceptable salt thereof.

8. A compound of the formula I according to claim 1 wherein each of R1 and R2, independently of the other, is selected from the group consisting of hydrogen, halo and $C_1$-$C_7$alkyl;

R3 is absent if Z is nitrogen or, if Z is C, then R3 is hydrogen or unsubstituted or substituted aryl;

X is N or CH,

Y is CH,

Z is C or N, and

Q is a moiety of the formula (A) wherein

R4 is hydrogen, halo, unsubstituted or substituted amino, unsubstituted or substituted aryl, unsubstituted or substituted heterocyclyl bound via a ring atom other than nitrogen, unsubstituted or substituted alkyl or unsubstituted or substituted alkynyl;

R5 is hydrogen, unsubstituted or substituted alkyl, unsubstituted or substituted amino, unsubstituted or substituted aryl or unsubstituted or substituted heterocyclyl; and R6 is hydrogen or substituted alkyl;

or a moiety of the formula (B) wherein

R7 is unsubstituted or substituted aryl and

R8 is alkyl or cycloalkyl;

where the asterisk * in formulae (A) and (B) marks the bond through which the moiety is bound to the NH of the amide group in formula I; and (a) each of R9 and R10, independently of the other, is selected from the group consisting of hydrogen, hydroxyl and $C_1$-$C_7$alkyl; or (b) R9 and R10 together represent oxo; or R1 and R9 together form a group —C(O)—CH2— or —CH2—CH2—, R2 is selected from the group consisting of hydrogen, halo and $C_1$-$C_7$-alkyl, and R10 represents hydrogen;

or a pharmaceutically acceptable salt thereof.

9. A compound of the formula I, selected from the group of compounds consisting of 2-(4-iminidazo[4,5-c]pyridin-1-yl-phenyl)-N-(3-trifluoromethyl-phenyl]-acetamide;

2-(4-imidazo[4,5-c]pyridin-1-yl-phenyl)-N-[4-(4-methyl-piperazin-1-ylmethyl)-3-trfluoromethyl-phenyl ]-acetamide;

N-(3'-chloro-2-trifluoromethyl-biphen-4-yl)-2-(4-imidazo[4,5-c]pyridin-1-yl-phenyl)-acetamide;

N-(3'-bromo-2-trffluoromethyl-biphen-4-yl)-2-(4-imidazo[4,5-c]pyridin-1-yl-phenyl)-acetamide;

N-{4-[(3-dimethylamino-propyl)-methyl-amino]-3-trffluoromethyl-phenyl}-2-(4-imidazo[4,5-c ]pyridin-1-yl-phenyl)-acetamide;

N-{4-[(2-dimethylamino-ethyl)-methyl-amino]-3-trifluoromethyl-phenyl}-2-(4-imidazo[4,5-c ]pyridin-1-yl-phenyl)-acetamide;

N-(3'-bromo-2-trfluoromethyl-biphen-4-yl)-2-(4-imidazo[4,5-b]pyridin-3-yl-phenyl)-acetamide;

2-(4-imidazo[4,5-b]pyridin-3-yl-phenyl)-N[4-(4-methyl-piperazin-1-ylmethyl)-3-trifluoromethyl-phenyl -acetamide;

N[4-(4-ethyl-piperazin-1-ylmethyl)-3-trifluoromethyl-phenyl]-2-(4-imidazo[4,5-b]pyridin-3-yl-phenyl) -acetamide;

2-(4-imidazo[4,5-b]pyridin-3-yl-phenyl)-N[4-(4-isopropyl-piperazin-1-ylmethyl)-3-trifluoromethyl-phenyl -acetamide;

N-{4-[(3-dimethylamino-propyl)-methyl-amino]-3-trfluoromethyl-phenyl}-2-(4-imidazo[4,5-b ]pyridin-3-yl-phenyl)-acetamide;

2-(4-imidazo[4,5-b]pyridin-3-yl-phenyl)-N-(4-iodo-3-trifluoromethyl-phenyl)-acetamide;

N-(4'-cyano-2-trifluoromethyl-biphen-4-yl)-2-(4-imidazo[4,5-b]pyridin-3-yl-phenyl)- acetamide;

2-(4-imidazo[4,5-b]pyridin-3-yl-phenyl)-N-(4'-methoxy-5-trifluoromethyl-biphen-3-yl)-acetamide;

2-(4-imidazo[4,5-b]pyridin-3-yl-phenyl)-N-{4-[methyl-(1-methyl-piperidin-4-yl)-amino]-3-trifluoromethyl -phenyl}-acetamide;

2-(2-chloro-4-imidazo[4,5-b]pyridin-3-yl-phenyl)-N[4-(4-isopropyl-piperazin-1-ylmethyl)-3-trifluoromethyl-phenyl-acetamide;

2-(2-chloro-4-imidazo[4,5-b]pyridin-3-yl-phenyl)-N[4-(4-methyll-piperazin-1-ylmethyl)-3-trifluoromethyl -phenyl-acetamide;

2-(2-chloro-4-imidazo[4,5-b]pyridin-3-yl-phenyl)-N-[4-(4-ethyll-piperazin-1-ylmethyl)-3-trifluoromethyl-phenyl-acetamide;

2-(2-chloro-4-imidazo[4,5-b]pyridin-3-yl-phenyl)-N-{4-[(3-dimethylamino-propyl)-methyl-amino]-3-trifluoromethyl-phenyl}-acetamide;

2-(4-benzoimidazol-1-yl-phenyl)-N-[4-(4-methyl-piperazin-1-ylmethyl)-3-trifluoromethyl-phenyl]-acetamide;

2-(4-benzoimidazol-1-yl-phenyl)-N-{4-[methyl-(1-methyl-piperidin-4-yl)-amino]-3-trifluoromethyl-phenyl }-acetamide;

2-(4-benzoimidazol-1-yl-phenyl)-N-{4-[(3-dimethylamino-propyl)-methyl-amino]-3-trifluoromethyl-phenyl }-acetamide;

2-(4-benzoimidazol-1-yl-phenyl)-N-{4-[(2-dimethylamino-ethyl)-methyl-amino]-3-trifluoromethyl-phenyl }-acetamide;

2-(4-benzoimidazol-1-yl-phenyl)-N-(4'-cyano-2-trifluoromethyl-biphen-4-yl)- acetamide;

2-{4-[5-(4-methoxy-phenyl)-benzoim idazol-1-yl]-phenyl}-N-[4-(4-methyl-piperazin-1-ylmethyl)-3-trifluoromethyl-phenyl-acetamide;

N-[4-(3-dimethylamino-prop-1-ynyl)-3-trifluoromethyl-phenyl]-2-(4-imidazo[4,5-b]pyridin-3-yl -phenyl)-acetamide and N-(5-tert-butyl-2-p-tolyl-2H-pyrazol-3-yl)-2-(4-imidazo[4,5-b]pyridine-3-yl-phenyl)-acetamide, or a pharmaceutically acceptable salt thereof 10. A pharmaceutical preparation comprising at least a compound of the formula I, or a pharmaceutically acceptable salt thereof, according to claim 1 and a pharmaceutically acceptable carrier material.

* * * * *